US012788906B2

(12) United States Patent
Ranjitsingh et al.

(10) Patent No.: US 12,788,906 B2
(45) Date of Patent: Nov. 10, 2026

(54) WOUND EDGE DIFFUSER

(71) Applicant: Fisher & Paykel Healthcare Limited, Auckland (NZ)

(72) Inventors: Michael Ranjitsingh, Auckland (NZ); Elmo Benson Stoks, Auckland (NZ); Aaron Joseph Lamont, Auckland (NZ); Callum James Thomas Spence, Auckland (NZ); Stephanie Louise Hazard, Auckland (NZ); Lydia Jane Gilmour, Auckland (NZ); David Johnathan Seymour Graham, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 947 days.

(21) Appl. No.: 17/997,193

(22) PCT Filed: May 4, 2021

(86) PCT No.: PCT/IB2021/053697
§ 371 (c)(1),
(2) Date: Oct. 26, 2022

(87) PCT Pub. No.: WO2021/224768
PCT Pub. Date: Nov. 11, 2021

(65) Prior Publication Data

US 2023/0173205 A1 Jun. 8, 2023

Related U.S. Application Data

(60) Provisional application No. 63/062,372, filed on Aug. 6, 2020, provisional application No. 63/019,945, filed on May 4, 2020.

(51) Int. Cl.

| | |
|---|---|
| ***A61M 13/00*** | (2006.01) |
| ***A61F 7/00*** | (2006.01) |
| ***A61M 11/00*** | (2006.01) |
| ***A61M 35/00*** | (2006.01) |

(52) U.S. Cl.
CPC .......... *A61M 13/003* (2013.01); *A61M 35/30* (2019.05); *A61F 2007/0052* (2013.01); *A61F 2007/006* (2013.01); *A61M 11/00* (2013.01)

(58) Field of Classification Search
CPC .... A61M 13/003; A61M 35/30; A61M 11/00; A61M 16/0066; A61M 16/1075;
(Continued)

(56) References Cited

U.S. PATENT DOCUMENTS 3,692,024 A 9/1972 Von Otto
4,205,668 A * 6/1980 Criddle .................. A61B 46/00
604/23
(Continued)

FOREIGN PATENT DOCUMENTS

CH 715525 A2 5/2020
DE 2903842 7/1980
(Continued)

OTHER PUBLICATIONS

International Search Report for International Application No. PCT/IB2021/053697 dated Jul. 14, 2021.

*Primary Examiner* — Theodore J Stigell
(74) *Attorney, Agent, or Firm* — Knobbe, Martens, Olson & Bear, LLP

(57) ABSTRACT

Disclosed herein is a patient interface for wound treatment and/or management, comprising: an interface body configurable to substantially or at least partially surround a wound, the interface body comprising a gas inlet and defining a first gas flow path having a first flow resistance, and a second gas flow path having a second flow resistance. The first gas flow path is arranged in fluid communication with the gas inlet and the second gas flow path. The interface body comprises or is configurable to provide a gas outlet at or adjacent to the wound site.

20 Claims, 34 Drawing Sheets

(58) Field of Classification Search
CPC .. A61M 16/109; A61M 16/16; A61M 16/161; A61M 2016/003; A61M 2202/0225; A61M 2205/0205; A61M 2205/332; A61M 2205/3331; A61M 2205/3334; A61M 2205/3368; A61M 2205/3653; A61M 2205/583; A61M 2205/584; A61M 2205/7536; A61M 2205/7545; A61M 2206/10; A61M 13/00; A61M 19/00; A61M 35/00; A61M 2202/0266; A61M 2205/3372; A61M 2205/36; A61M 2205/75; A61M 2207/00; A61F 2007/0052; A61F 2007/006; A61F 7/00; A61F 2007/0071; A61F 2007/0096; A61B 46/20; A61B 2046/205; A61B 90/40
See application file for complete search history.

(56) References Cited

U.S. PATENT DOCUMENTS

| | | | | |
|---|---|---|---|---|
| 5,015,243 | A | 5/1991 | Schifano | |
| 5,636,643 | A * | 6/1997 | Argenta | A61F 13/05 602/42 |
| 6,407,307 | B1 | 6/2002 | Augustine | |
| 6,494,858 | B1 | 12/2002 | van der Linden | |
| 6,942,650 | B1 | 9/2005 | Schultz et al. | |
| 2006/0200100 | A1 | 9/2006 | Rosati | |
| 2006/0206051 | A1 * | 9/2006 | Hamilton | A61B 46/23 606/228 |
| 2013/0284183 | A1 | 10/2013 | Hillis et al. | |
| 2016/0136364 | A1 | 5/2016 | Jensen et al. | |
| 2016/0184160 | A1 | 6/2016 | Self et al. | |
| 2016/0310224 | A1 | 10/2016 | Dye et al. | |
| 2018/0153637 | A1 | 6/2018 | Al-Shawi et al. | |
| 2020/0121510 | A1 | 4/2020 | Hartwell et al. | |

FOREIGN PATENT DOCUMENTS

| | | | |
|---|---|---|---|
| WO | WO 2007/047664 | A2 | 4/2007 |
| WO | WO 2013/138449 | A1 | 9/2013 |
| WO | WO 2019/055176 | A1 | 3/2019 |
| WO | WO 2019/084006 | A1 | 5/2019 |
| WO | WO 2019/139823 | A2 | 7/2019 |

* cited by examiner

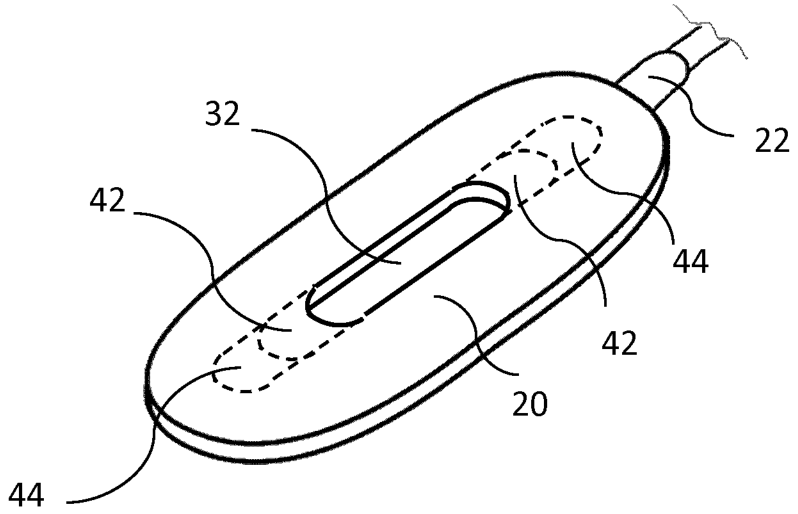
Fig. 4
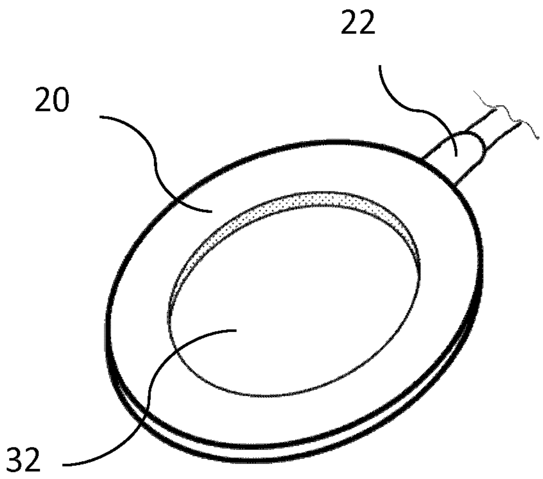
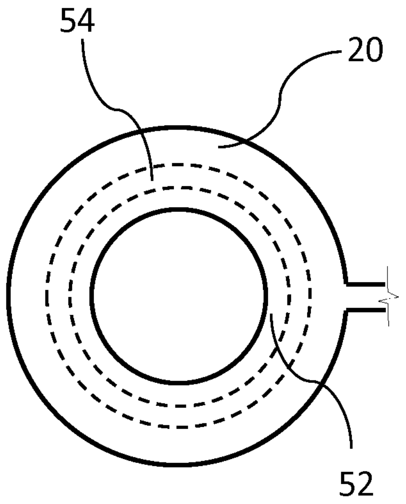
Fig. 5a
Fig. 5b

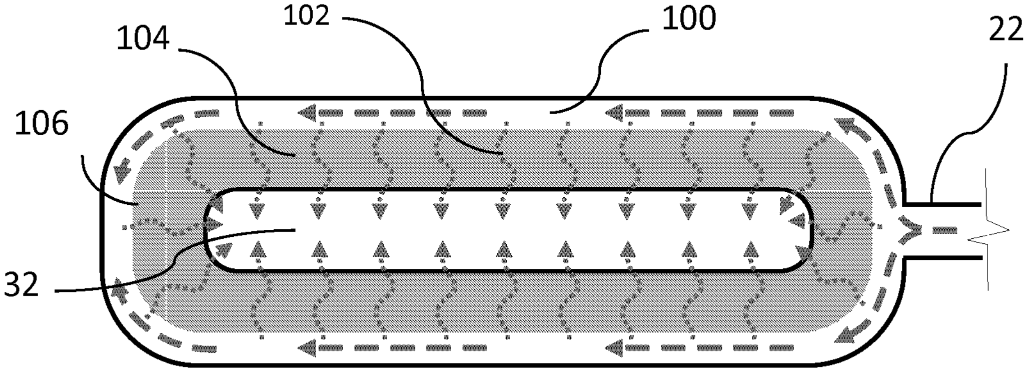
Fig. 10
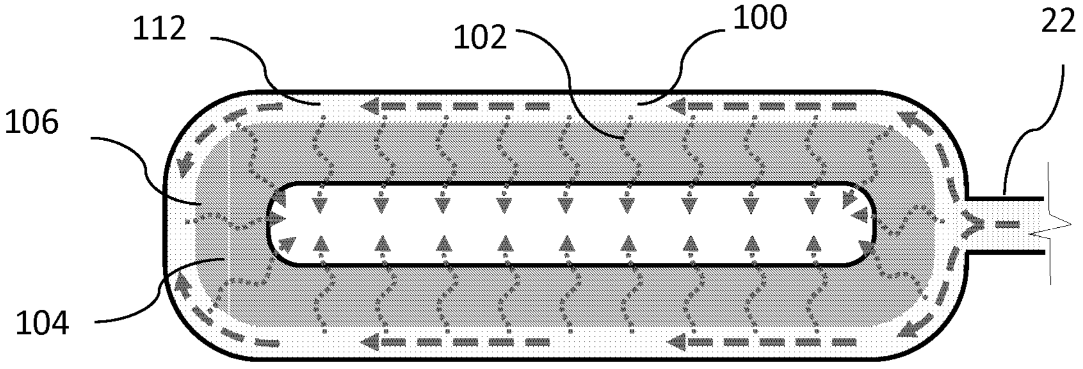
Fig. 11
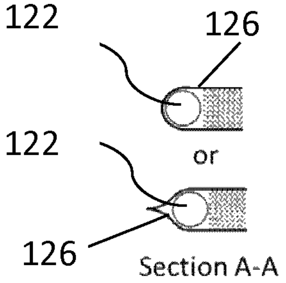
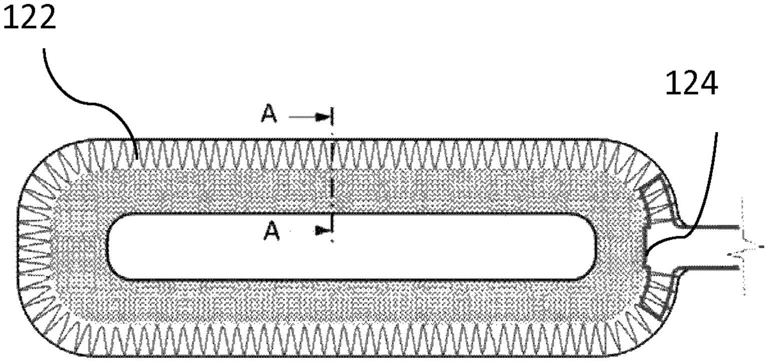
Fig. 12b
Fig. 12a (a)

(b)

(c)

(a)

(b)

(a)

(b)

WOUND EDGE DIFFUSER

CROSS-REFERENCE TO RELATED APPLICATIONS

The present application claims priority from U.S. provisional patent application 63/019,945 filed 4 May 2020 and U.S. provisional patent application 63/062,372 filed 6 Aug. 2020, the contents of which are incorporated herein by reference in their entirety.

TECHNICAL FIELD

The present disclosure relates to a patient interface for wound treatment and/or management. It further relates to a system for wound treatment and/or management, a method of managing a wound, and uses of the system in surgical operations and post-surgical operations.

BACKGROUND

Open wounds may be created intentionally during surgery to access a surgical site or they can occur acutely due to trauma or chronically due to disease. In either case, internal tissues are exposed to the atmosphere and non-physiological conditions. Exposure of delicate internal tissues causes cell damage and contamination, both of which compromise wound healing. Cell damage is caused by hypothermia, desiccation, and hypoxia of tissue. Tissue is inherently non-sterile, and pathogens are normally present. Often pathogens are within limits tolerated by the host's immune system. Open wounds, however, are exposed to an increased level of bio-burden from airborne, surgeon, and/or patient sources (such as the patient's skin and sebaceous glands). The open wound and resulting insult to tissue also compromise the body's ability to manage bio-burden. Outcomes of open wounds can be improved by preserving physiological conditions over open wounds and preventing contamination while internal tissues are exposed.

In open surgery, insufflation gases can be insufflated to a wound site, including in orthopaedic (particularly hip and knee), vascular, plastic or cardiac surgery, for example. The insufflation gas can be selected from air, carbon dioxide ($CO_2$), nitrogen, nitric oxide or any suitable gases.

The performance of insufflation gases in preserving physiological conditions over and/or in the wound site and in preventing contamination of exposed internal tissues is affected at least in part by the manner of its delivery to the wound site.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

The present disclosure describes embodiments of patient interfaces that may be used to create a gas flow microenvironment over, across, about and/or in or adjacent a surgical site which may comprise the site of proposed surgery, an open wound such as a surgical wound, and/or a closed wound, such as a post-operative surgical wound preserving physiological conditions and/or mitigating risk of contamination in the wound. Some embodiments of the patient interface are configured to deliver, as far as possible, a substantially even distribution of gas flow to an outlet of the patient interface that can surround the surgical site e.g. wound. The gas flow may be warmed and/or humidified, The gas flow may maintain the temperature of a wound site substantially at a particular temperature and/or humidity and/or prevent unwanted air from entering into the surgical wound site. When the patient interface is configured to deliver warm, humidified air, the gas flow may assist to prevent desiccation or drying of the tissue.

Aspects of the disclosure are summarised below. It will be noted that aspects and embodiments of the disclosure may be combined such that features and/or embodiments of one aspect may be used with features and/or embodiments of any other aspect where compatible.

According to an aspect, a patient interface for wound treatment and/or management comprises an interface body configurable to substantially or at least partially surround a wound. The interface body comprises a gas inlet and defines a first gas flow path having a first flow resistance, and a second gas flow path having a second flow resistance; the first gas flow path being arranged in fluid communication with the inlet and the second gas flow path, the interface body further comprising or being configurable to provide a gas outlet at or adjacent to the wound.

In some aspects and embodiments, the patient interface, in use around a wound, may be configured to produce a gas curtain or blanket around and/or in the wound, creating a protective microenvironment over and/or in the wound. The gas curtain or blanket may be formed from gas that exits the patient interface through at least one gas outlet at or adjacent the wound.

The second flow resistance may be greater than the first flow resistance.

Accordingly, gas may be relatively free to flow through the first gas flow path and then slow in its passage through the second gas flow path towards the gas outlet. The gas outlet may be provided at an inner surface of the interface body so as to partially or entirely surround the wound during use of the patient interface.

The interface body may include a diffusing material portion, the second gas flow path being defined in the diffusing material portion. The first gas flow path may substantially surround the second gas flow path and/or the diffusing material portion. The inner surface of the interface body may be an inner surface of the diffusing material portion. The diffusing material portion of the interface body may comprise a stretchable porous material. The stretchable porous material may comprise one of a foam, a fabric, a woven or a cellular structure. The stretchable porous material may be an open cell foam. The stretchable nature of the diffusing material portion may allow it to conform to the contours of the patient's body and for it to be retracted, together with the wound itself, so as to deliver gas over the wound edge.

The first gas flow path may substantially surround the diffusing material portion. Gas may therefore enter the diffusing material portion from the first gas flow path, and therefore enter the second gas flow path from the first gas flow path, around an outer periphery of the diffusing material portion.

The interface body may have an enclosing wall or outer membrane and the first gas flow path may be defined between the outer membrane and the diffusing material portion of the interface body. Throughout the specification, the terms 'wall', 'membrane', 'film' and 'skin' are used interchangably such that reference to one may include the others.

A support structure may be arranged in and/or around the first gas flow path between the outer membrane and the diffusing material portion of the interface body. In an embodiment, the support structure may be formed integrally with the first gas flow path e.g. it may be integrated with the outer membrane. Such a support structure can prevent the first gas flow path from collapsing or being crushed, for example under the force of a retractor, thus maintaining the first gas flow path open. The support structure may be a scaffold or spring, for example. The enclosing wall or outer membrane of the interface body may be translucent or transparent to allow visibility into the first gas flow path, and/or the diffusing material portion and to show any condensate building up in the patient interface 10.

The support structure may comprise a flexible structure configurable to conform to the contours of the body of the patient surrounding the wound site. It may be configured to be deformable under application of a laterally and/or vertically and/or longitudinally applied force. The support structure may have a cross-sectional shape configured to substantially resist vertical and/or laterally applied loads. The support structure may be configured to conform to the contours of the body of the patient whilst also substantially resisting vertically applied loads. It may have a cross-sectional shape configured to substantially resist torsional force. For example, the support structure may comprise a generally square or rectangular cross-sectional shape having a pair of opposing first sides and a pair of opposing second sides disposed substantially perpendicularly to the pair of opposing first sides. In this case, the support structure may comprise a connecting member at each of the pair of opposing second sides.

Alternatively, the support structure may comprise a generally C-shaped cross-sectional shape having a pair of opposing first sides and a single second side disposed substantially perpendicularly to the pair of opposing first sides, an opposing second side to the single second side remaining substantially open.

The flexible structure may comprise a plurality of interconnected elements arranged in a repeating pattern over a longitudinal axis of the support structure.

In one embodiment, the plurality of interconnected elements includes a plurality of substantially X-shaped elements extending in a repeated pattern along each of the pair of opposing first sides, and wherein adjacent X-shaped elements share a connecting member that extends substantially perpendicularly to the pair of opposing first sides to connect the adjacent X-shaped elements of one side of the pair of opposing first sides to the corresponding adjacent X-shaped elements of the other of the pair of opposing first sides. A point of intersection of each of the plurality of substantially X-shaped elements may be substantially at a mid-point of each of the pair of opposing first sides. Alternatively, the point of intersection of each of the plurality of substantially X-shaped elements may be offset from a mid-point of each of the pair of opposing first sides. This configuration may provide asymmetric conformability such that the support structure could be orientated in a direction in which greater flexibility is required The connecting member may have a shape that tapers inwardly towards a mid-point of each of the pair of opposing second sides. In one embodiment, the connecting member is substantially X-shaped.

In an embodiment, each of the pair of opposing first sides comprises a repeating square wave or rounded wave pattern, whereby each repeat of the pattern comprises a first slot extending from one of the pair of opposing second sides towards the other of the pair of opposing second sides and an adjacent second slot extending from the other of the pair of opposing second sides towards the one of the pair of opposing second sides.

A width of each of the first slot and the second slot may be less than a width of a portion of the support structure extending between the first slot and the second slot. This configuration has a greater degree of rigidity and a lesser degree of flexibility than an alternative embodiment in which a width of each of the first slot and the second slot is greater than or equal to a width of a portion of the support structure extending between the first slot and the second slot. This configuration may be used when more flexibility is required.

The support structure may further include a notch or cut-away in portions of one of the pair of opposing second sides adjacent each of the slots in the repeating square wave or repeating rounded wave pattern.

For embodiments of the support structure having a substantially C-shaped cross-section, each of the pair of opposing first sides may comprise a repeating square wave or rounded wave pattern, whereby each repeat of the pattern comprises a first slot extending from the single second side towards the substantially open side of the pair of opposing second sides and an adjacent second slot extending from the substantially open side of the pair of opposing second sides towards the single side of the pair of opposing second sides. The open side of the C-shaped support structure may pinch or encapsulate a portion of the diffusing material adjacent the first gas flow path.

A distal end portion of each of the slots in the repeating rounded wave pattern may be rounded and the or each second side is rounded with a corresponding curvature.

A height of the second side or each side of the pair of opposing second sides may taper over at least a portion of a longitudinal axis of the support structure. Furthermore, a width of each of the pair of opposing first sides may taper over at least a portion of a longitudinal axis of the support structure.

In another embodiment of the support structure, the plurality of interconnected elements includes a plurality of rectangular or square shaped bands extending in a repeated pattern over a longitudinal axis of the support structure, the plurality of rectangular or square shaped bands being interconnected by a longitudinal spine extending the length of the support structure at a mid-point of each of a pair of opposing first sides of the support structure.

In further embodiments, the support structure comprises a flexible structure having a generally circular or rhombus shaped cross-section.

The first gas flow path may have a constant cross-section. Alternatively, the first gas flow path may have a variable cross-section. The cross-section of the first gas flow path may be controlled to produce a desired gas flow characteristic through the first gas flow path. For example, the first gas flow path cross-section may be controlled to provide a spatially more even flow rate through the diffusing material. The interface body may have a distal portion opposite the gas inlet and in some embodiments, the first gas flow path may increase in cross section from the gas inlet to the distal portion. This increasing cross-section may assist in overcoming areas of higher pressure at or adjacent the gas inlet, e.g. due to viscosity and friction effects, and therefore create a more even flow pressure around an outer periphery of the diffusing material portion and therefore a spatially more even flow rate through the diffusing material. In other embodiments, the first gas flow path may decrease in cross section from the gas inlet to the distal portion. To supply an even flowrate through the second gas flow path, the flowrate diminishes in the first gas flow path away from the gas inlet. The larger cross section at the gas inlet allows for this larger flowrate to pass while minimising viscous losses and pressure loss.

Additionally or alternatively, an imbalance of flow pressure in the first gas flow path may be offset by varying a thickness of the diffusing material portion. In some embodiments, the diffusing material portion defining the second gas flow path increases in thickness from the gas inlet to the distal portion. This configuration imposes a higher resistance to the gases in the first gas flow path towards the distal portion. In other embodiments, the diffusing material portion defining the second gas flow path decreases in thickness from the inlet to the distal portion. This configuration imposes a higher resistance to the gases in the first gas flow path closer to the gas inlet.

The first gas flow path may be located above, below and/or at least partially around the second gas flow path. In an embodiment, the first gas flow path substantially surrounds a periphery of the diffusing material portion.

The outer membrane may comprise a sealed skin or film extending over at least a top surface and an outer peripheral surface of the diffusing material portion. In some embodiments, the outer membrane further extends over a bottom surface of the diffusing material portion. Accordingly, in some embodiments, the only exposed surface of the diffusing material portion to the atmosphere may be the inner surface that surrounds the wound and gas flowing through the second gas path may therefore only exit the interface body at the inner surface. Nevertheless, this control of gas flow may also be achieved, even when the outer membrane does not cover the bottom surface, by adhering the bottom surface to skin of a patient during use. The outer membrane may comprise a stretchable material, for example.

In some embodiments of the patient interface, a bottom surface of the interface body includes an adhesive material. The adhesive material may cover substantially the entire bottom surface. Alternatively it may cover one or more portions of the bottom surface. For example, the adhesive material may be arranged in a winding or wiggle pattern on the bottom surface or in discrete portions. Such arrangements of adhesive material may prevent bunching of the interface body as it conforms to the contours of a patient's body.

As an alternative to adhesive material, the patient interface may have a fixing material arranged on a bottom surface of the interface body. The fixing material may include one or more of a silicone, a gel or other non-adhesive tacky material.

A top surface of the interface body may include a visible incision guide line. The visible incision guide line may be perforated and/or printed. In addition or alternatively, the interface body may include a pre-shaped slot extending through the diffusing material portion. The pre-shaped slot may include one or more pre-defined adjustable portions. The one or more pre-defined adjustable portions may comprise one or more perforated portions.

To assist a surgeon to make the correct or desired surgical incision at the wound site, the top surface of the interface body may have surgical incision length indicators marked along at least one edge of the pre-shaped slot. The surgical incision length indicators may or may not be numbered and could be in any unit of measure, for example millimetres, centimetres or inches. In one embodiment, the support structure pattern itself may provide the indicator i.e. the repeating pattern could be designed to repeat every/have a period of 5 mm or 10 mm or another suitable distance such that by making an incision that extends over a certain number of repeating patterns of the support structure, the incision length is known.

In some embodiments, the interface body may have a height dimension of no more than about 10 mm. Accordingly, it may have a low profile that minimises visual and physical interference for the surgeon of the wound site. The interface body may have a footprint that is determined to suit a particular anticipated wound size or type of surgery. The pre-shaped slot may have a width dimension of between 5 mm to 80 mm, or between 10 to 40 mm, in an initial or resting state thereof.

The interface body of the patient interface may include a heating element or device. The heating element or device may include a heater wire in the first gas flow path and/or in the second gas flow path. Alternatively or additionally, the heating element or device may include one or more heater pads or heated fabric, and/or electrically conductive foam and/or an electrically conductive housing.

The heating element or device may be positioned on or adjacent to a bottom surface and/or top surface of the patient interface. The heating element or device may be positioned adjacent to and/or in thermal communication with one or more of the diffusing material portion, the first gas path and the second gas flow path.

The heating element or device comprises one or more heater pads or heated fabric surfaces. The one or more heating pads or heated fabric surfaces is divided up into multiple areas by at least one slit or slot. Preferably, the one or more heating pads or heated fabric surfaces is divided up into multiple areas by an alternating pattern of slots or slits.

The one or more heating pads or heated fabric surfaces may comprise polyethylene terephthalate (PET) monofilaments and conductive fibres. Alternatively, the one or more heating pads may comprise a heated wire loop.

The interface body may comprise two or more diffusing material portions of different densities and wherein the second gas path passes through the two or more diffusing material portions. Such a configuration can provide a means to control the passage of gases through the second gas flow path, by introducing a graduating change or step change in flow resistance to the gases entering the second gas flow path at different points in the second gas flow path or at different locations along the interface between the first gas flow path and the second gas flow path.

The patient interface may include one or more flow restrictions arranged between the first gas flow path and the second gas flow path. The flow restrictions may include one or more of a baffle, a series of orifices, a series of slits or a series of slots. In some embodiments, the flow restrictions are configured to be more restrictive of fluid flow at or adjacent the gas inlet of the interface body than at the distal portion thereof. This configuration allows for the slowing of gases passing through to the second gas flow path from the first gas flow path at or adjacent the inlet of the interface body, which may contribute towards providing an even flow exiting the second gas flow path at the inner surface of the diffusing material portion.

One or more flow directors and/or flow splitters may be arranged at or adjacent the gas inlet to encourage gas flow entering the first gas flow path to flow around the abrupt corners at the juncture of the gas inlet and the first gas flow path, minimising turbulence and flow separation that can impede the gas flow through the first gas flow path. Where the outer membrane is transparent or translucent, the one or more flow directors and/or flow splitters may be visible through the outer membrane.

In some embodiments, the interface body has more than one gas inlet, to encourage an even flow of gases through the first gas flow path.

The interface body at the gas outlet may be configured to influence a direction of gas flow exiting the interface body. In one embodiment, a top surface of the interface body extends beyond, e.g. radially inwardly of, the inner surface of the interface body. This configuration may encourage the gas flow exiting the interface body to flow downwards or remain close to the patient interface and over the wound to protect the wound. In another embodiment, a bottom surface of the interface body extends beyond, e.g. radially inwardly of, the inner surface of the interface body. This configuration may help deflect airborne particles away from the wound, avoiding potential contamination.

The inner surface of the interface body may be angled inwardly from a top to a bottom thereof. This configuration may also gently encourage a downward flow of gases to create a protective environment over the wound. Conversely, the inner surface of the interface body may be angled outwardly from a top to a bottom thereof, which may gently encourage the gas to flow upwardly from the inner surface.

In some embodiments, a section of a top surface of the diffusing material portion adjacent the gas outlet may be exposed to atmosphere. Alternatively or additionally, a section of a bottom surface of the diffusing material portion adjacent the gas outlet may be exposed to atmosphere. The inner surface of the interface body may have a stepped profile such that an upper portion of the inner surfaced is recessed back from a lower portion of the inner surface. Alternatively or additionally, the inner surface of the interface body may have a stepped profile such that a lower portion of the inner surface is recessed back from an upper portion of the inner surface.

According to another aspect, a patient interface for wound treatment and/or management comprises an interface body configurable to substantially or at least partially surround a wound. The interface body comprises a gas inlet and defines a first gas flow path, and a second gas flow path; the first gas flow path being arranged in fluid communication with the inlet and the second gas flow path, the interface body further comprising or being configurable to provide a gas outlet at or adjacent to the wound.

The patient interface may be configured to emit warmed and/or humidified gas from the gas outlet.

The first gas flow path may have a first flow resistance. The second gas flow path may have a second flow resistance.

The second flow resistance may be greater than the first flow resistance.

Accordingly, gas may be relatively free to flow through the first gas flow path and then slow in its passage through the second gas flow path towards the gas outlet. The gas outlet may be provided at an inner surface of the interface body so as to partially or entirely surround the wound during use of the patient interface.

The interface body may include a diffusing material portion, the second gas flow path being defined in the diffusing material portion. The first gas flow path may substantially surround the second gas flow path and/or the diffusing material portion. The inner surface of the interface body may be an inner surface of the diffusing material portion. The diffusing material portion of the interface body may comprise a stretchable porous material. The stretchable porous material may comprise one of a foam, a fabric, a woven or a cellular structure. The stretchable porous material may be an open cell foam. The stretchable nature of the diffusing material portion may allow it to conform to the contours of the patient's body and for it to be retracted, together with the wound itself, so as to deliver gas over the wound edge.

The first gas flow path may substantially surround the diffusing material portion. Gas may therefore enter the diffusing material portion from the first gas flow path, and therefore enter the second gas flow path from the first gas flow path, around an outer periphery of the diffusing material portion.

The interface body may have an enclosing wall or outer membrane and the first gas flow path may be defined between the outer membrane and the diffusing material portion of the interface body. A support structure may be arranged in and/or around the first gas flow path between the outer membrane and the diffusing material portion of the interface body. In an embodiment, the support structure may be formed integrally with the first gas flow path e.g. it may be integrated with the outer membrane. Such a support structure can prevent the first gas flow path from collapsing or being crushed, for example under the force of a retractor, thus maintaining the first gas flow path open. The support structure may be a scaffold or spring, for example. The enclosing wall or outer membrane of the interface body may be translucent or transparent to allow visibility into the first gas flow path, and/or the diffusing material portion and to show any condensate building up in the patient interface 10.

The support structure may comprise a flexible structure configurable to conform to the contours of the body of the patient surrounding the wound site. It may be configured to be deformable under application of a laterally and/or vertically and/or longitudinally applied force. The support structure may have a cross-sectional shape configured to substantially resist vertical and/or laterally applied loads. It may have a cross-sectional shape configured to substantially resist torsional force. For example, the support structure may comprise a generally square or rectangular cross-sectional shape having a pair of opposing first sides and a pair of opposing second sides disposed substantially perpendicularly to the pair of opposing first sides. In this case, the support structure may comprise a connecting member at each of the pair of opposing second sides.

Alternatively, the support structure may comprise a generally C-shaped cross-sectional shape having a pair of opposing first sides and a single second side disposed substantially perpendicularly to the pair of opposing first sides, an opposing second side to the single second side remaining substantially open.

The flexible structure may comprise a plurality of interconnected elements arranged in a repeating pattern over a longitudinal axis of the support structure.

In one embodiment, the plurality of interconnected elements includes a plurality of substantially X-shaped elements extending in a repeated pattern along each of the pair of opposing first sides, and wherein adjacent X-shaped elements share a connecting member that extends substantially perpendicularly to the pair of opposing first sides to connect the adjacent X-shaped elements of one side of the pair of opposing first sides to the corresponding adjacent X-shaped elements of the other of the pair of opposing first sides. A point of intersection of each of the plurality of substantially X-shaped elements may be substantially at a mid-point of each of the pair of opposing first sides. Alternatively, the point of intersection of each of the plurality of substantially X-shaped elements may be offset from a mid-point of each of the pair of opposing first sides. This configuration may provide asymmetric conformability such that the support structure could be orientated in a direction in which greater flexibility is required The connecting member may have a shape that tapers inwardly towards a mid-point of each of the pair of opposing second sides. In one embodiment, the connecting member is substantially X-shaped.

In an embodiment, each of the pair of opposing first sides comprises a repeating square wave or rounded wave pattern, whereby each repeat of the pattern comprises a first slot extending from one of the pair of opposing second sides towards the other of the pair of opposing second sides and an adjacent second slot extending from the other of the pair of opposing second sides towards the one of the pair of opposing second sides.

A width of each of the first slot and the second slot may be less than a width of a portion of the support structure extending between the first slot and the second slot. This configuration has a greater degree of rigidity and a lesser degree of flexibility than an alternative embodiment in which a width of each of the first slot and the second slot is greater than or equal to a width of a portion of the support structure extending between the first slot and the second slot. This configuration may be used when more flexibility is required.

The support structure may further include a notch or cut-away in portions of one of the pair of opposing second sides adjacent each of the slots in the repeating square wave or repeating rounded wave pattern.

For embodiments of the support structure having a substantially C-shaped cross-section, each of the pair of opposing first sides may comprise a repeating square wave or rounded wave pattern, whereby each repeat of the pattern comprises a first slot extending from the single second side towards the substantially open side of the pair of opposing second sides and an adjacent second slot extending from the substantially open side of the pair of opposing second sides towards the single side of the pair of opposing second sides. The open side of the C-shaped support structure may pinch or encapsulate a portion of the diffusing material adjacent the first gas flow path.

A distal end portion of each of the slots in the repeating rounded wave pattern may be rounded and the or each second side is rounded with a corresponding curvature.

A height of the second side or each side of the pair of opposing second sides may taper over at least a portion of a longitudinal axis of the support structure. Furthermore, a width of each of the pair of opposing first sides may taper over at least a portion of a longitudinal axis of the support structure.

In another embodiment of the support structure, the plurality of interconnected elements includes a plurality of rectangular or square shaped bands extending in a repeated pattern over a longitudinal axis of the support structure, the plurality of rectangular or square shaped bands being interconnected by a longitudinal spine extending the length of the support structure at a mid-point of each of a pair of opposing first sides of the support structure.

In further embodiments, the support structure comprises a flexible structure having a generally circular or rhombus shaped cross-section.

The first gas flow path may have a constant cross-section. Alternatively, the first gas flow path may have a variable cross-section. The cross-section of the first gas flow path may be controlled to produce a desired gas flow characteristic through the first gas flow path. For example, the first gas flow path cross-section may be controlled to provide a spatially more even flow rate through the diffusing material. The interface body may have a distal portion opposite the gas inlet and in some embodiments, the first gas flow path may increase in cross section from the gas inlet to the distal portion. This increasing cross-section may assist in overcoming areas of higher pressure at or adjacent the gas inlet, e.g. due to viscosity and friction effects, and therefore create a more even flow pressure around an outer periphery of the diffusing material portion and therefore a spatially more even flow rate through the diffusing material. In other embodiments, the first gas flow path may decrease in cross section from the gas inlet to the distal portion. To supply an even flowrate through the second gas flow path, the flowrate diminishes in the first gas flow path away from the gas inlet. The larger cross section at the gas inlet allows for this larger flowrate to pass while minimising viscous losses and pressure loss.

Additionally or alternatively, an imbalance of flow pressure in the first gas flow path may be offset by varying a thickness of the diffusing material portion. In some embodiments, the diffusing material portion defining the second gas flow path increases in thickness from the gas inlet to the distal portion. This configuration imposes a higher resistance to the gases in the first gas flow path towards the distal portion. In other embodiments, the diffusing material portion defining the second gas flow path decreases in thickness from the inlet to the distal portion. This configuration imposes a higher resistance to the gases in the first gas flow path closer to the gas inlet.

The first gas flow path may be located above, below and/or at least partially around the second gas flow path. In an embodiment, the first gas flow path substantially surrounds a periphery of the diffusing material portion.

The outer membrane may comprise a sealed skin or film extending over at least a top surface and an outer peripheral surface of the diffusing material portion. In some embodiments, the outer membrane further extends over a bottom surface of the diffusing material portion. Accordingly, in some embodiments, the only exposed surface of the diffusing material portion to the atmosphere may be the inner surface that surrounds the wound and gas flowing through the second gas path may therefore only exit the interface body at the inner surface. Nevertheless, this control of gas flow may also be achieved, even when the outer membrane does not cover the bottom surface, by adhering the bottom surface to skin of a patient during use. The outer membrane may comprise a stretchable material, for example.

In some embodiments of the patient interface, a bottom surface of the interface body includes an adhesive material. The adhesive material may cover substantially the entire bottom surface. Alternatively it may cover one or more portions of the bottom surface. For example, the adhesive material may be arranged in a winding or wiggle pattern on the bottom surface or in discrete portions. Such arrangements of adhesive material may prevent bunching of the interface body as it conforms to the contours of a patient's body.

As an alternative to adhesive material, the patient interface may have a fixing material arranged on a bottom surface of the interface body. The fixing material may include one or more of a silicone, a gel or other non-adhesive tacky material.

A top surface of the interface body may include a visible incision guide line. The visible incision guide line may be perforated and/or printed. In addition or alternatively, the interface body may include a pre-shaped slot extending through the diffusing material portion. The pre-shaped slot may include one or more pre-defined adjustable portions. The one or more pre-defined adjustable portions may comprise one or more perforated portions.

To assist a surgeon to make the correct or desired surgical incision at the wound site, the top surface of the interface body may have surgical incision length indicators marked along at least one edge of the pre-shaped slot. The surgical incision length indicators may or may not be numbered and could be in any unit of measure, for example millimetres, centimetres or inches. In one embodiment, the support structure pattern itself may provide the indicator i.e. the repeating pattern could be designed to repeat every/have a period of 5 mm or 10 mm or another suitable distance such that by making an incision that extends over a certain number of repeating patterns of the support structure, the incision length is known.

In some embodiments, the interface body may have a height dimension of no more than about 10 mm. Accordingly, it may have a low profile that minimises visual and physical interference for the surgeon of the wound site. The interface body may have a footprint that is determined to suit a particular anticipated wound size or type of surgery. The pre-shaped slot may have a width dimension of between 5 mm to 80 mm, or between 10 to 40 mm, in an initial or resting state thereof.

The interface body of the patient interface may include a heating element or device. The heating element or device may include a heater wire in the first gas flow path and/or in the second gas flow path. Alternatively or additionally, the heating element or device may include one or more heater pads or heated fabric, and/or electrically conductive foam and/or an electrically conductive housing.

The heating element or device may be positioned on or adjacent to a bottom surface and/or top surface of the patient interface. The heating element or device may be positioned adjacent to and/or in thermal communication with one or more of the diffusing material portion, the first gas path and the second gas flow path.

The heating element or device comprises one or more heater pads or heated fabric surfaces. The one or more heating pads or heated fabric surfaces is divided up into multiple areas by at least one slit or slot. Preferably, the one or more heating pads or heated fabric surfaces is divided up into multiple areas by an alternating pattern of slots or slits.

The one or more heating pads or heated fabric surfaces may comprise polyethylene terephthalate (PET) monofilaments and conductive fibres. Alternatively, the one or more heating pads may comprise a heated wire loop.

The interface body may comprise two or more diffusing material portions of different densities and wherein the second gas path passes through the two or more diffusing material portions. Such a configuration can provide a means to control the passage of gases through the second gas flow path, by introducing a graduating change or step change in flow resistance to the gases entering the second gas flow path at different points in the second gas flow path or at different locations along the interface between the first gas flow path and the second gas flow path.

The patient interface may include one or more flow restrictions arranged between the first gas flow path and the second gas flow path. The flow restrictions may include one or more of a baffle, a series of orifices, a series of slits or a series of slots. In some embodiments, the flow restrictions are configured to be more restrictive of fluid flow at or adjacent the gas inlet of the interface body than at the distal portion thereof. This configuration allows for the slowing of gases passing through to the second gas flow path from the first gas flow path at or adjacent the inlet of the interface body, which may contribute towards providing an even flow exiting the second gas flow path at the inner surface of the diffusing material portion.

One or more flow directors and/or flow splitters may be arranged at or adjacent the gas inlet to encourage gas flow entering the first gas flow path to flow around the abrupt corners at the juncture of the gas inlet and the first gas flow path, minimising turbulence and flow separation that can impede the gas flow through the first gas flow path. Where the outer membrane is transparent or translucent, the one or more flow directors and/or flow splitters may be visible through the outer membrane.

In some embodiments, the interface body has more than one gas inlet, to encourage an even flow of gases through the first gas flow path.

The interface body at the gas outlet may be configured to influence a direction of gas flow exiting the interface body. In one embodiment, a top surface of the interface body extends beyond, e.g. radially inwardly of, the inner surface of the interface body. This configuration may encourage the gas flow exiting the interface body to flow downwards or remain close to the patient interface and over the wound to protect the wound. In another embodiment, a bottom surface of the interface body extends beyond, e.g. radially inwardly of, the inner surface of the interface body. This configuration may help deflect airborne particles away from the wound, avoiding potential contamination.

The inner surface of the interface body may be angled inwardly from a top to a bottom thereof. This configuration may also gently encourage a downward flow of gases to create a protective environment over the wound. Conversely, the inner surface of the interface body may be angled outwardly from a top to a bottom thereof, which may gently encourage the gas to flow upwardly from the inner surface.

In some embodiments, a section of a top surface of the diffusing material portion adjacent the gas outlet may be exposed to atmosphere. Alternatively or additionally, a section of a bottom surface of the diffusing material portion adjacent the gas outlet may be exposed to atmosphere. The inner surface of the interface body may have a stepped profile such that an upper portion of the inner surfaced is recessed back from a lower portion of the inner surface. Alternatively or additionally, the inner surface of the interface body may have a stepped profile such that a lower portion of the inner surface is recessed back from an upper portion of the inner surface.

According to another aspect, a patient interface for wound treatment and/or management comprises an interface body configurable to substantially or at least partially surround a wound, the interface body comprising a gas inlet and defining a gas flow path; the gas flow path being arranged in fluid communication with the gas inlet, the interface body further comprising or being configurable to provide a gas outlet at or adjacent to the wound, and further comprising a function indicator configured to provide an indication of when a gas is flowing through the patient interface.

The function indicator may be configured to provide a visual indication of when a gas is flowing through the patient interface. The function indicator may be further configured to provide an indication of when a gas flowing through the patient interface is warmed and/or humidified and/or a particular gas type.

The function indicator may comprise a thermochromic and/or a hydrochromic material, and may be adapted for changing colour in the presence of a particular gas.

The interface body may define a first gas flow path having a first flow resistance, and a second gas flow path having a second flow resistance; the first gas flow path being arranged in fluid communication with the gas inlet and the second gas flow path, and wherein the function indicator is a support structure positioned in the first gas flow path of the interface body. The interface body may comprise an outer membrane around the first gas flow path, wherein the outer membrane is transparent or translucent to allow visualisation of the support structure.

The function indicator may be in communication with the first gas flow path. It may be in one or more of direct communication, indirect communication or thermal communication with the first gas flow path. The function indicator may be a flow director and/or flow splitter arranged at or adjacent the gas inlet.

According to an aspect, a system for wound management and/or treatment comprises a patient interface having a function indicator, and a gas source; wherein the patient interface is arranged in fluid communication with the gas source and wherein the function indicator of the patient interface is an inline flow indicator arranged in fluid communication with the gas source and the patient interface.

According to a further aspect, a patient interface for wound treatment and/or management, comprises an interface body configurable to substantially or at least partially surround a wound, the interface body comprising a gas inlet and defining a gas flow path; the gas flow path being arranged in fluid communication with the gas inlet, the interface body further comprising or being configurable to provide a gas outlet at or adjacent to the wound, and wherein the interface body includes a heating element or device.

The interface body may define a first gas flow path having a first flow resistance, and a second gas flow path having a second flow resistance; the first gas flow path being arranged in fluid communication with the gas inlet and the second gas flow path, wherein the interface body includes a diffusing material portion, and wherein the second gas flow path is defined in the diffusing material portion.

The heating element or device may be positioned on or adjacent to a bottom surface and/or top surface of the patient interface. The heating element or device may be positioned adjacent to and/or in thermal communication with one or more of the diffusing material portion, the first gas path and the second gas flow path. The heating element or device may comprise one or more heater pads or heated fabric surfaces. The one or more heating pads or heated fabric surfaces may be divided up into multiple areas by at least one slit or slot. The one or more heating pads or heated fabric surfaces is divided up into multiple areas by an alternating pattern of slots or slits.

The one or more heating pads or heated fabric surfaces may comprise polyethylene terephthalate (PET) monofilaments and conductive fibres. Alternatively, the one or more heating pads may comprise a heated wire loop.

According to a further aspect, a patient interface for wound treatment and/or management comprises an interface body configured or configurable to substantially or at least partially surround a surgical site e.g. a wound. The interface body comprises a gas inlet and defines a gas flow path, the gas flow path being arranged in fluid communication with the gas outlet. The interface body is configured to emit a gas flow out of the gas outlet which is one or more of omnidirectional, uniformly distributed across the gas outlet, non-turbulent, and of uniform velocity.

Gas may be relatively free to flow through the first gas flow path and then slow in its passage through the second gas flow path towards the gas outlet. The gas outlet may be provided at an inner surface of the interface body so as to partially or entirely surround the wound during use of the patient interface.

The gas flow path may comprise a first gas flow path and/or a second gas flow path.

The interface body may include a diffusing material portion, the second gas flow path being defined in the diffusing material portion. The first gas flow path may substantially surround the second gas flow path and/or the diffusing material portion. The inner surface of the interface body may be an inner surface of the diffusing material portion. The diffusing material portion of the interface body may comprise a stretchable porous material. The stretchable porous material may comprise one of a foam, a fabric, a woven or a cellular structure. The stretchable porous material may be an open cell foam. The stretchable nature of the diffusing material portion may allow it to conform to the contours of the patient's body and for it to be retracted, together with the wound itself, so as to deliver gas over the wound edge.

The first gas flow path may substantially surround the diffusing material portion. Gas may therefore enter the diffusing material portion from the first gas flow path, and therefore enter the second gas flow path from the first gas flow path, around an outer periphery of the diffusing material portion.

The interface body may have an enclosing wall or outer membrane and the first gas flow path may be defined between the outer membrane and the diffusing material portion of the interface body. A support structure may be arranged in the first gas flow path between the outer membrane and the diffusing material portion of the interface body. Such a support structure can prevent the first gas flow path from collapsing or being crushed, for example under the force of a retractor, thus maintaining the first gas flow path open. The support structure may be as described in any of the aspects of the present disclosure and may be a scaffold or spring, for example. The outer membrane of the interface body may be translucent or transparent to allow visibility into the first gas flow path, and/or the diffusing material portion and to show any condensate building up in the patient interface 10.

The first gas flow path may have a constant cross-section. Alternatively, the first gas flow path may have a variable cross-section. The cross-section of the first gas flow path may be controlled to produce a desired gas flow characteristic through the first gas flow path. For example, the first gas flow path cross-section may be controlled to provide a spatially more even flow rate through the diffusing material. The interface body may have a distal portion opposite the gas inlet and in some embodiments, the first gas flow path may increase in cross section from the gas inlet to the distal portion. This increasing cross-section may assist in overcoming areas of higher pressure at or adjacent the gas inlet, e.g. due to viscosity and friction effects, and therefore create a more even flow pressure around an outer periphery of the diffusing material portion and therefore a spatially more even flow rate through the diffusing material. In other embodiments, the first gas flow path may decrease in cross section from the gas inlet to the distal portion. To supply an even flowrate through the second gas flow path, the flowrate diminishes in the first gas flow path away from the gas inlet. The larger cross section at the gas inlet allows for this larger flowrate to pass while minimising viscous losses and pressure loss.

Additionally or alternatively, an imbalance of flow pressure in the first gas flow path may be offset by varying a thickness of the diffusing material portion. In some embodiments, the diffusing material portion defining the second gas flow path increases in thickness from the gas inlet to the distal portion. This configuration imposes a higher resistance to the gases in the first gas flow path towards the distal portion. In other embodiments, the diffusing material portion defining the second gas flow path decreases in thickness from the inlet to the distal portion. This configuration imposes a higher resistance to the gases in the first gas flow path closer to the gas inlet.

The first gas flow path may be located above, below and/or at least partially around the second gas flow path. In an embodiment, the first gas flow path substantially surrounds a periphery of the diffusing material portion.

The outer membrane may comprise a sealed skin or film extending over at least a top surface and an outer peripheral surface of the diffusing material portion. In some embodiments, the outer membrane further extends over a bottom surface of the diffusing material portion. Accordingly, in some embodiments, the only exposed surface of the diffusing material portion to the atmosphere may be the inner surface that surrounds the wound and gas flowing through the second gas path may therefore only exit the interface body at the inner surface. Nevertheless, this control of gas flow may also be achieved, even when the outer membrane does not cover the bottom surface, by adhering the bottom surface to skin of a patient during use. The outer membrane may comprise a stretchable material, for example.

In some embodiments of the patient interface, a bottom surface of the interface body includes an adhesive material. The adhesive material may cover substantially the entire bottom surface. Alternatively it may cover one or more portions of the bottom surface. For example, the adhesive material may be arranged in a winding or wiggle pattern on the bottom surface or in discrete portions. Such arrangements of adhesive material may prevent bunching of the interface body as it conforms to the contours of a patient's body.

As an alternative to adhesive material, the patient interface may have a fixing material arranged on a bottom surface of the interface body. The fixing material may include one or more of a silicone, a gel or other non-adhesive tacky material.

A top surface of the interface body may include a visible incision guide line. The visible incision guide line may be perforated and/or printed. In addition or alternatively, the interface body may include a pre-shaped slot extending through the diffusing material portion. The pre-shaped slot may include one or more pre-defined adjustable portions. The one or more pre-defined adjustable portions may comprise one or more perforated portions.

To assist a surgeon to make the correct or desired surgical incision at the wound site, the top surface of the interface body may have surgical incision length indicators marked along at least one edge of the pre-shaped slot. The surgical incision length indicators may or may not be numbered and could be in any unit of measure, for example millimetres, centimetres or inches.

In some embodiments, the interface body may have a height dimension of no more than about 10 mm. Accordingly, it may have a low profile that minimises visual and physical interference for the surgeon of the wound site. The interface body may have a footprint that is determined to suit a particular anticipated wound size or type of surgery. The pre-shaped slot may have a width dimension of between 5 mm to 80 mm, or between 10 to 40 mm, in an initial or resting state thereof.

The interface body may comprise two or more diffusing material portions of different densities and wherein the second gas path passes through the two or more diffusing material portions. Such a configuration can provide a means to control the passage of gases through the second gas flow path, by introducing a graduating change or step change in flow resistance to the gases entering the second gas flow path at different points in the second gas flow path or at different locations along the interface between the first gas flow path and the second gas flow path.

The patient interface may include one or more flow restrictions arranged between the first gas flow path and the second gas flow path. The flow restrictions may include one or more of a baffle, a series of orifices, a series of slits or a series of slots. In some embodiments, the flow restrictions are configured to be more restrictive of fluid flow at or adjacent the gas inlet of the interface body than at the distal portion thereof. This configuration allows for the slowing of gases passing through to the second gas flow path from the first gas flow path at or adjacent the inlet of the interface body, which may contribute towards providing an even flow exiting the second gas flow path at the inner surface of the diffusing material portion.

One or more flow directors and/or flow splitters may be arranged at or adjacent the gas inlet to encourage gas flow entering the first gas flow path to flow around the abrupt corners at the juncture of the gas inlet and the first gas flow path, minimising turbulence and flow separation that can impede the gas flow through the first gas flow path. Where the outer membrane is transparent or translucent, the one or more flow directors and/or flow splitters may be visible through the outer membrane.

In some embodiments, the interface body has more than one gas inlet, to encourage an even flow of gases through the first gas flow path.

The interface body at the gas outlet may be configured to influence a direction of gas flow exiting the interface body. In one embodiment, a top surface of the interface body extends beyond, e.g. radially inwardly of, the inner surface of the interface body. This configuration may encourage the gas flow exiting the interface body to flow downwards or remain close to the patient interface and over the wound to protect the wound. In another embodiment, a bottom surface of the interface body extends beyond, e.g. radially inwardly of, the inner surface of the interface body. This configuration may help deflect airborne particles away from the wound, avoiding potential contamination.

The inner surface of the interface body may be angled inwardly from a top to a bottom thereof. This configuration may also gently encourage a downward flow of gases to create a protective environment over the wound. Conversely, the inner surface of the interface body may be angled outwardly from a top to a bottom thereof, which may gently encourage the gas to flow upwardly from the inner surface.

In some embodiments, a section of a top surface of the diffusing material portion adjacent the gas outlet may be exposed to atmosphere. Alternatively or additionally, a section of a bottom surface of the diffusing material portion adjacent the gas outlet may be exposed to atmosphere. The inner surface of the interface body may have a stepped profile such that an upper portion of the inner surfaced is recessed back from a lower portion of the inner surface. Alternatively or additionally, the inner surface of the interface body may have a stepped profile such that a lower portion of the inner surface is recessed back from an upper portion of the inner surface.

According to a further aspect, a patient interface for wound treatment and/or management comprises an interface body configured or configurable to substantially or at least partially surround a surgical site e.g. a wound. The interface body comprises a first gas flow path and a second gas flow path. The first gas flow path may have a constant cross-section. The second gas flow path may have a varying cross section.

An imbalance of flow pressure in the first gas flow path may be offset by varying a thickness of the diffusing material portion. In some embodiments, the diffusing material portion defining the second gas flow path increases in thickness from the gas inlet to the distal portion. This configuration imposes a higher resistance to the gases in the first gas flow path towards the distal portion. In other embodiments, the diffusing material portion defining the second gas flow path decreases in thickness from the inlet to the distal portion. This configuration imposes a higher resistance to the gases in the first gas flow path closer to the gas inlet.

According to a yet further aspect, a patient interface for wound treatment and/or management comprises an interface body configured or configurable to substantially or at least partially surround a wound. The interface body comprises a gas inlet, a first gas flow path and a second gas flow path. The first gas flow path may have a varying cross section. The second gas flow path may have a substantially constant cross section.

The interface body may have a distal portion opposite the gas inlet and in some embodiments, the first gas flow path may increase in cross section from the gas inlet to the distal portion. This increasing cross-section may assist in overcoming areas of higher pressure at or adjacent the gas inlet, e.g. due to viscosity and friction effects, and therefore create a more even flow pressure around an outer periphery of the diffusing material portion and therefore a spatially more even flow rate through the diffusing material. In other embodiments, the first gas flow path may decrease in cross section from the gas inlet to the distal portion. To supply an even flowrate through the second gas flow path, the flowrate diminishes in the first gas flow path away from the gas inlet. The larger cross section at the gas inlet allows for this larger flowrate to pass while minimising viscous losses and pressure loss.

According to a still further aspect, a patient interface for wound treatment and/or management comprises an interface body configured or configurable to substantially or at least partially surround a surgical site e.g. a wound. The interface body comprises a gas inlet, a first gas flow path and a second gas flow path. The first gas flow path is maintained in an open position by a support structure. The support structure may be as described in any aspect of the present disclosure.

The support structure may be arranged in and/or around the first gas flow path. The interface body may have an outer membrane and the first gas flow path may be defined between the outer membrane and a diffusing material portion of the interface body. In an embodiment, the support structure may be formed integrally with the first gas flow path e.g. it may be integrated with the outer membrane.

The support structure may be a scaffold or spring. The support structure may comprise an elongate flexible structure having a longitudinal axis, and configured to be elastically deformable under application of a laterally and/or vertically and/or longitudinally applied force.

The support structure may be configured to be bendable in a lateral direction relative to the longitudinal axis. The support structure may be configured to be bendable to conform to contours of a body of a patient surrounding the wound.

The support structure may have a cross-sectional shape configured to substantially resist compressive force. It may be configured to permit torsional movement.

The support structure may comprise a generally square or rectangular cross-sectional shape having a pair of opposing first sides and a pair of opposing second sides disposed substantially perpendicularly to the pair of opposing first sides. Each of the pair of opposing first sides may comprise a repeating square wave or rounded wave pattern, whereby each repeat of the pattern defines a first slot extending from one of the pair of opposing second sides towards the other of the pair of opposing second sides and an adjacent second slot extending from the other of the pair of opposing second sides towards the one of the pair of opposing second sides. Each of the first slot and the second slot may comprise a squared or rounded wall at the respective opposing second side, forming a structural portion between the opposing first sides. A width of each of the first slot and the second slot may be less than a width of a portion of the support structure extending between the first slot and the second slot when in the first position thereof. Alternatively, a width of each of the first slot and the second slot is greater than or equal to a width of a portion of the support structure extending between the first slot and the second slot when in the first position thereof.

According to a further aspect, a support structure for providing structural support to a patient interface comprises an elongate flexible structure having a longitudinal axis, and configured to be elastically deformable under application of a laterally and/or vertically and/or longitudinally applied force. The support structure may be used in a patient interface of any other aspect of the present disclosure.

The support structure may be a scaffold or spring. The support structure may comprise an elongate flexible structure having a longitudinal axis, and configured to be elastically deformable under application of a laterally and/or vertically and/or longitudinally applied force.

The support structure may be configured to be bendable in a lateral direction relative to the longitudinal axis. The support structure may be configured to be bendable to conform to contours of a body of a patient surrounding the wound.

The support structure may have a cross-sectional shape configured to substantially resist compressive force. It may be configured to permit torsional movement.

The support structure may comprise a generally square or rectangular cross-sectional shape having a pair of opposing first sides and a pair of opposing second sides disposed substantially perpendicularly to the pair of opposing first sides. Each of the pair of opposing first sides may comprise a repeating square wave or rounded wave pattern, whereby each repeat of the pattern defines a first slot extending from one of the pair of opposing second sides towards the other of the pair of opposing second sides and an adjacent second slot extending from the other of the pair of opposing second sides towards the one of the pair of opposing second sides. Each of the first slot and the second slot may comprise a squared or rounded wall at the respective opposing second side, forming a structural portion between the opposing first sides. A width of each of the first slot and the second slot may be less than a width of a portion of the support structure extending between the first slot and the second slot when in the first position thereof. Alternatively, a width of each of the first slot and the second slot is greater than or equal to a width of a portion of the support structure extending between the first slot and the second slot when in the first position thereof.

The enclosing wall or outer membrane of the interface body may be translucent or transparent to allow visibility into the first gas flow path, and/or the diffusing material portion and to show any condensate building up in the patient interface 10.

The support structure may be configurable to conform to the contours of the body of the patient surrounding the wound site. It may be configured to be deformable under application of a laterally and/or vertically and/or longitudinally applied force. It may have a cross-sectional shape configured to substantially resist torsional force. For example, the support structure may comprise a generally square or rectangular cross-sectional shape having a pair of opposing first sides and a pair of opposing second sides disposed substantially perpendicularly to the pair of opposing first sides. In this case, the support structure may comprise a connecting member at each of the pair of opposing second sides.

Alternatively, the support structure may comprise a generally C-shaped cross-sectional shape having a pair of opposing first sides and a single second side disposed substantially perpendicularly to the pair of opposing first sides, an opposing second side to the single second side remaining substantially open.

The flexible structure may comprise a plurality of interconnected elements arranged in a repeating pattern over a longitudinal axis of the support structure.

In one embodiment, the plurality of interconnected elements includes a plurality of substantially X-shaped elements extending in a repeated pattern along each of the pair of opposing first sides, and wherein adjacent X-shaped elements share a connecting member that extends substantially perpendicularly to the pair of opposing first sides to connect the adjacent X-shaped elements of one side of the pair of opposing first sides to the corresponding adjacent X-shaped elements of the other of the pair of opposing first sides. A point of intersection of each of the plurality of substantially X-shaped elements may be substantially at a mid-point of each of the pair of opposing first sides. Alternatively, the point of intersection of each of the plurality of substantially X-shaped elements may be offset from a mid-point of each of the pair of opposing first sides.

The connecting member may have a shape that tapers inwardly towards a mid-point of each of the pair of opposing second sides. In one embodiment, the connecting member is substantially X-shaped.

In an embodiment, each of the pair of opposing first sides comprises a repeating square wave or rounded wave pattern, whereby each repeat of the pattern comprises a first slot extending from one of the pair of opposing second sides towards the other of the pair of opposing second sides and an adjacent second slot extending from the other of the pair of opposing second sides towards the one of the pair of opposing second sides.

A width of each of the first slot and the second slot may be less than a width of a portion of the support structure extending between the first slot and the second slot. This configuration has a greater degree of rigidity and a lesser degree of flexibility than an alternative embodiment in which a width of each of the first slot and the second slot is greater than or equal to a width of a portion of the support structure extending between the first slot and the second slot. This configuration may be used when more flexibility is required.

The support structure may further include a notch or cut-away in portions of one of the pair of opposing second sides adjacent each of the slots in the repeating square wave or repeating rounded wave pattern.

For embodiments of the support structure having a substantially C-shaped cross-section, each of the pair of opposing first sides may comprise a repeating square wave or rounded wave pattern, whereby each repeat of the pattern comprises a first slot extending from the single second side towards the substantially open side of the pair of opposing second sides and an adjacent second slot extending from the substantially open side of the pair of opposing second sides towards the single side of the pair of opposing second sides. The open side of the C-shaped support structure may pinch or encapsulate a portion of the diffusing material adjacent the first gas flow path.

A distal end portion of each of the slots in the repeating rounded wave pattern may be rounded and the or each second side is rounded with a corresponding curvature.

A height of the second side or each side of the pair of opposing second sides may taper over at least a portion of a longitudinal axis of the support structure. Furthermore, a width of each of the pair of opposing first sides may taper over at least a portion of a longitudinal axis of the support structure.

In another embodiment of the support structure, the plurality of interconnected elements includes a plurality of rectangular or square shaped bands extending in a repeated pattern over a longitudinal axis of the support structure, the plurality of rectangular or square shaped bands being interconnected by a longitudinal spine extending the length of the support structure at a mid-point of each of a pair of opposing first sides of the support structure.

In further embodiments, the support structure comprises a flexible structure having a generally circular or rhombus shaped cross-section.

The support structure may be provided in the first gas flow path as a continuous single structure. Alternatively, it may include at least two or more separate repeating lengths. The separate lengths may be positioned end to end to create the support structure and/or may be connected or assembled together.

According to a further aspect, a patient interface for wound treatment and/or management comprises an interface body comprising a gas inlet and a gas flow path; the gas flow path being arranged in fluid communication with the gas inlet, the interface body further comprising or being configurable to provide a gas outlet; and an enclosing wall or outer membrane defining at least part of the gas flow path, at least a region of said enclosing wall or outer membrane being of a material that allows the passage of water vapour. The material may allow the passage of water vapour to reduce or eliminate condensation and/or build-up of liquid moisture in the first gas flow path.

Throughout the description, a material that allows the passage of water molecules through a wall of the material, without allowing the bulk passage of liquid water or bulk flow of gases all the way through the wall is described as a 'breathable' material. Passage of water molecules through such a wall, such as a monolithic wall, may be via the solution-diffusion mechanism. It may be appreciated by one of skill in the art that the water molecules in the wall are molecularly dispersed in the media and are therefore without a state (solid, liquid or gas), sometimes referred to in the art as vapour. The rate of transfer is often referred to as a water vapour transmission rate or the like.

A 'breathable' material may be breathable due to its composition, physical structure or a combination thereof. Examples of breathable materials include block copolymers, hydrophilic polyester block copolymers, thermoplastic elastomers, styrene block polymers, copolyester elastomers, thermoplastic polyolefin elastomers, thermoplastic polyurethane elastomers, non-porous monolithic polymers, polyurethanes, hydrophilic thermoplastics, hydrophilic polyesters, perfluorinated polymers, polyamides, and woven treated fabrics exhibiting breathable characteristics.

The outer membrane over or defining at least part of the first gas flow path may be made of the breathable material. A variety of designs of the patient interface utilizing the breathable material are possible: for example, the entire enclosing wall/outer membrane of the interface body may be formed of a breathable material; a portion of the enclosing wall/outer membrane over the first gas flow path may be formed of a breathable material; a portion of the enclosing wall/outer membrane over a top of the first gas flow path may be formed of a breathable material. A region or regions e.g. portions of the entire enclosing wall/outer membrane or of the first gas flow path may be formed of the breathable material. The breathable material may be placed over the support structure of the first gas flow path; and/or may be bonded or otherwise attached to the support structure. The breathable material may be located in 'gaps' of the support structure. The interface body may comprise one or more layers of breathable material. The breathable material can provide a water vapour flow path from the interface body to ambient air.

The breathable material may comprise of a film such as a thin film. Throughout the specification, the terms film, thin film and membrane can be understood to be interchangeable. Furthermore, the breathable material may be transparent and/or translucent.

Breathable regions of the interface body allow diffusion of water vapour from the interface to eliminate or mitigate the build up of condensation within the interface body, in particular the first gas flow path. The breathable regions therefore may reduce the risk of condensation accumulation and possible saturation of the diffuser material.

A monolithic wall is a wall that does not contain open channels or through holes from one major surface to another.

Alternatively, the interface body may have an enclosing wall or outer membrane defining at least part of the gas flow path, at least a region of said enclosing wall or outer membrane being of a microporous or porous material that allows transmission of water vapour. For example, the region(s) of enclosing wall or outer membrane may comprise a microporous polymer film. The small size of the pores in such films may prevent the penetration of liquid water, but allow for transmission of water vapour.

A porous or microporous material may be porous due to composition, physical structure or a combination thereof. Examples of porous or microporous materials include thermoplastic elastomers, thermoplastic polyurethane elastomers, polyurethanes, hydrophilic thermoplastics, polyolefins. The porous or microporous material may be a film or membrane. For example, the porous or microporous material may be a stretched polytet-rafluoroethylene (PTFE) or precipitation-cast polyurethane.

According to a further aspect, a patient interface for wound treatment and/or management, comprises: an interface body configurable to substantially or at least partially surround a wound, the interface body comprising a gas inlet and defining a first gas flow path, and a second gas flow path; the first gas flow path being arranged in fluid communication with the gas inlet and the second gas flow path, the interface body further comprising or being configurable to provide a gas outlet at or adjacent to the wound, wherein the interface body is configured to be retractable from a first position to a second retracted position whilst substantially maintaining the first gas flow path and the second gas flow path.

The gas outlet may be provided at an inner surface of the interface body. The interface body may include a diffusing material portion. The second gas flow path may be defined in the diffusing material portion. The diffusing material portion may comprise a stretchable porous material, for example it may comprise one of a foam, a fabric, a woven or cellular structure. In an embodiment, the stretchable porous material is an open cell foam.

The interface body may have an enclosing wall or outer membrane, wherein the first gas flow path is defined between the enclosing wall or outer membrane and the diffusing material portion.

A support structure is arranged in the first gas flow path between the outer membrane and the diffusing material portion of the interface body.

The support structure may be a scaffold or spring. The support structure may comprise an elongate flexible structure having a longitudinal axis, and configured to be elastically deformable under application of a laterally and/or vertically and/or longitudinally applied force.

The support structure may be configured to be bendable in a lateral direction relative to the longitudinal axis. The support structure may be configured to be bendable to conform to contours of a body of a patient surrounding the wound.

The support structure may have a cross-sectional shape configured to substantially resist compressive force. It may be configured to permit torsional movement.

The support structure may comprise a generally square or rectangular cross-sectional shape having a pair of opposing first sides and a pair of opposing second sides disposed substantially perpendicularly to the pair of opposing first sides. Each of the pair of opposing first sides may comprise a repeating square wave or rounded wave pattern, whereby each repeat of the pattern defines a first slot extending from one of the pair of opposing second sides towards the other of the pair of opposing second sides and an adjacent second slot extending from the other of the pair of opposing second sides towards the one of the pair of opposing second sides. Each of the first slot and the second slot may comprise a squared or rounded wall at the respective opposing second side, forming a structural portion between the opposing first sides. A width of each of the first slot and the second slot may be less than a width of a portion of the support structure extending between the first slot and the second slot when in the first position thereof. Alternatively, a width of each of the first slot and the second slot is greater than or equal to a width of a portion of the support structure extending between the first slot and the second slot when in the first position thereof.

According to a further aspect, a support structure for providing structural support to a patient interface comprises an elongate flexible structure having a longitudinal axis, and configured to be elastically deformable under application of a laterally and/or vertically and/or longitudinally applied force. The support structure may be used in a patient interface of any other aspect of the present disclosure.

The support structure may be a scaffold or spring. The support structure may comprise an elongate flexible structure having a longitudinal axis, and configured to be elastically deformable under application of a laterally and/or vertically and/or longitudinally applied force.

The support structure may be configured to be bendable in a lateral direction relative to the longitudinal axis. The support structure may be configured to be bendable to conform to contours of a body of a patient surrounding the wound.

The support structure may have a cross-sectional shape configured to substantially resist compressive force. It may be configured to permit torsional movement.

The support structure may comprise a generally square or rectangular cross-sectional shape having a pair of opposing first sides and a pair of opposing second sides disposed substantially perpendicularly to the pair of opposing first sides. Each of the pair of opposing first sides may comprise a repeating square wave or rounded wave pattern, whereby each repeat of the pattern defines a first slot extending from one of the pair of opposing second sides towards the other of the pair of opposing second sides and an adjacent second slot extending from the other of the pair of opposing second sides towards the one of the pair of opposing second sides. Each of the first slot and the second slot may comprise a squared or rounded wall at the respective opposing second side, forming a structural portion between the opposing first sides. A width of each of the first slot and the second slot may be less than a width of a portion of the support structure extending between the first slot and the second slot when in the first position thereof. Alternatively, a width of each of the first slot and the second slot is greater than or equal to a width of a portion of the support structure extending between the first slot and the second slot when in the first position thereof.

The enclosing wall or outer membrane of the interface body may be translucent or transparent to allow visibility into the first gas flow path, and/or the diffusing material portion and to show any condensate building up in the patient interface 10.

The support structure may be configurable to conform to the contours of the body of the patient surrounding the wound site. It may be configured to be deformable under application of a laterally and/or vertically and/or longitudinally applied force. It may have a cross-sectional shape configured to substantially resist torsional force. For example, the support structure may comprise a generally square or rectangular cross-sectional shape having a pair of opposing first sides and a pair of opposing second sides disposed substantially perpendicularly to the pair of opposing first sides. In this case, the support structure may comprise a connecting member at each of the pair of opposing second sides.

Alternatively, the support structure may comprise a generally C-shaped cross-sectional shape having a pair of opposing first sides and a single second side disposed substantially perpendicularly to the pair of opposing first sides, an opposing second side to the single second side remaining substantially open.

The flexible structure may comprise a plurality of interconnected elements arranged in a repeating pattern over a longitudinal axis of the support structure.

In one embodiment, the plurality of interconnected elements includes a plurality of substantially X-shaped elements extending in a repeated pattern along each of the pair of opposing first sides, and wherein adjacent X-shaped elements share a connecting member that extends substantially perpendicularly to the pair of opposing first sides to connect the adjacent X-shaped elements of one side of the pair of opposing first sides to the corresponding adjacent X-shaped elements of the other of the pair of opposing first sides. A point of intersection of each of the plurality of substantially X-shaped elements may be substantially at a mid-point of each of the pair of opposing first sides. Alternatively, the point of intersection of each of the plurality of substantially X-shaped elements may be offset from a mid-point of each of the pair of opposing first sides.

The connecting member may have a shape that tapers inwardly towards a mid-point of each of the pair of opposing second sides. In one embodiment, the connecting member is substantially X-shaped.

In an embodiment, each of the pair of opposing first sides comprises a repeating square wave or rounded wave pattern, whereby each repeat of the pattern comprises a first slot extending from one of the pair of opposing second sides towards the other of the pair of opposing second sides and an adjacent second slot extending from the other of the pair of opposing second sides towards the one of the pair of opposing second sides.

A width of each of the first slot and the second slot may be less than a width of a portion of the support structure extending between the first slot and the second slot. This configuration has a greater degree of rigidity and a lesser degree of flexibility than an alternative embodiment in which a width of each of the first slot and the second slot is greater than or equal to a width of a portion of the support structure extending between the first slot and the second slot. This configuration may be used when more flexibility is required.

The support structure may further include a notch or cut-away in portions of one of the pair of opposing second sides adjacent each of the slots in the repeating square wave or repeating rounded wave pattern.

For embodiments of the support structure having a substantially C-shaped cross-section, each of the pair of opposing first sides may comprise a repeating square wave or rounded wave pattern, whereby each repeat of the pattern comprises a first slot extending from the single second side towards the substantially open side of the pair of opposing second sides and an adjacent second slot extending from the substantially open side of the pair of opposing second sides towards the single side of the pair of opposing second sides. The open side of the C-shaped support structure may pinch or encapsulate a portion of the diffusing material adjacent the first gas flow path.

A distal end portion of each of the slots in the repeating rounded wave pattern may be rounded and the or each second side is rounded with a corresponding curvature.

A height of the second side or each side of the pair of opposing second sides may taper over at least a portion of a longitudinal axis of the support structure. Furthermore, a width of each of the pair of opposing first sides may taper over at least a portion of a longitudinal axis of the support structure.

In another embodiment of the support structure, the plurality of interconnected elements includes a plurality of rectangular or square shaped bands extending in a repeated pattern over a longitudinal axis of the support structure, the plurality of rectangular or square shaped bands being interconnected by a longitudinal spine extending the length of the support structure at a mid-point of each of a pair of opposing first sides of the support structure.

In further embodiments, the support structure comprises a flexible structure having a generally circular or rhombus shaped cross-section.

According to a further aspect, a system for wound management and/or treatment comprises a patient interface in accordance with any aspect of the present disclosure and a gas source. The patient interface, e.g. the gas inlet thereof, is arranged in fluid communication with the gas source.

The system may further comprise a gas controller for controlling one or more functions including, but not limited to, the gas flow rate, pressure, mixing of gases, delivery of drugs or medicaments to gas mixtures (for example, some gas types such as $CO_2$, nitric oxide may be considered to be drugs), delivery of liquid drugs. The system may further comprise a gas conditioner for heating and/or humidifying gas supplied from the gas source prior to its entry to the patient interface.

According to a further aspect, a method of treatment of a wound using the patient interface or system of any aspect of the present disclosure comprises, prior to an incision being made at the wound site or intended wound site: applying the patient interface to a wound site or intended wound site; and turning on a flow of gas from a/the gas source to the patient interface. Applying the patient interface to a wound site or intended wound site may comprise applying multiple patient interfaces to the wound site or intended wound site in order to adequately surround the wound site or intended wound site.

The method may further comprise conditioning the gas prior to its entry into the patient interface. Conditioning the gas may comprise one or more of conditioning the temperature, humidity level, carbon dioxide level or composition of the gas.

According to a still further aspect, a method of protecting a patient from one or more of: surgical site infection, loss of moisture and/or loss of heat using the patient interface or support structure or system of any aspect of the present disclosure, comprises applying the patient interface adjacent a wound site or intended wound site; and turning on a flow of gas from a/the gas source to the patient interface.

Applying the patient interface adjacent a wound site or intended wound site may comprise applying multiple patient interfaces adjacent the wound site or intended wound site in order to adequately surround the wound site or intended wound site.

The method may further comprise conditioning the gas prior to its entry into the patient interface. Conditioning the gas may comprise one or more of conditioning the temperature, humidity level or oxygen level of the gas.

According to a still further aspect, there is provided the use of the patient interface and/or the support structure and/or the system of any aspect of the present disclosure in a surgical operation.

According to a still further aspect, there is provided the use of the patient interface and/or the support structure and/or the system of any aspect of the present disclosure in managing a post-operative wound site.

For purposes of summarizing the disclosed apparatus, systems and methods, certain aspects, advantages and novel features of the disclosed apparatus, systems and methods have been described herein. It is to be understood that not necessarily all advantages may be achieved in accordance with any particular embodiment of the disclosed apparatus, systems and methods. Thus, the disclosed apparatus, systems and methods may be embodied or carried out in a manner that achieves or optimizes one advantage or group of advantages as taught herein without necessarily achieving other advantages as may be taught or suggested herein.

BRIEF DESCRIPTION OF DRAWINGS

One or more embodiments of the present disclosure will now be described by way of specific example(s) with reference to the accompanying drawings, in which:

FIG. 4 is a perspective view of a further embodiment of a patient interface;

FIG. 5*a* is a perspective view of a still further embodiment of a patient interface;

FIG. 5*b* is a schematic plan view of a yet further embodiment of a patient interface;

FIG. 10 is a schematic cross-sectional view of an embodiment of a patient interface having peripheral first gas flow path;

FIG. 11 is a schematic cross-sectional view of the patient interface of FIG. 10 including a scaffold or support structure;

FIG. 12*a* is a schematic cross-sectional view of the patient interface of FIG. 10 including a spring;

FIG. 12*b* is two possible options of a cross-sectional view of the patient interface of FIG. 12*a* at A-A;

FIGS. 46-46*c* are cross-sectional schematic views of a patient interface with one or more pairs of semi-impermeable or substantially gas permeable portions;

DESCRIPTION OF EMBODIMENTS

Figure 1A:
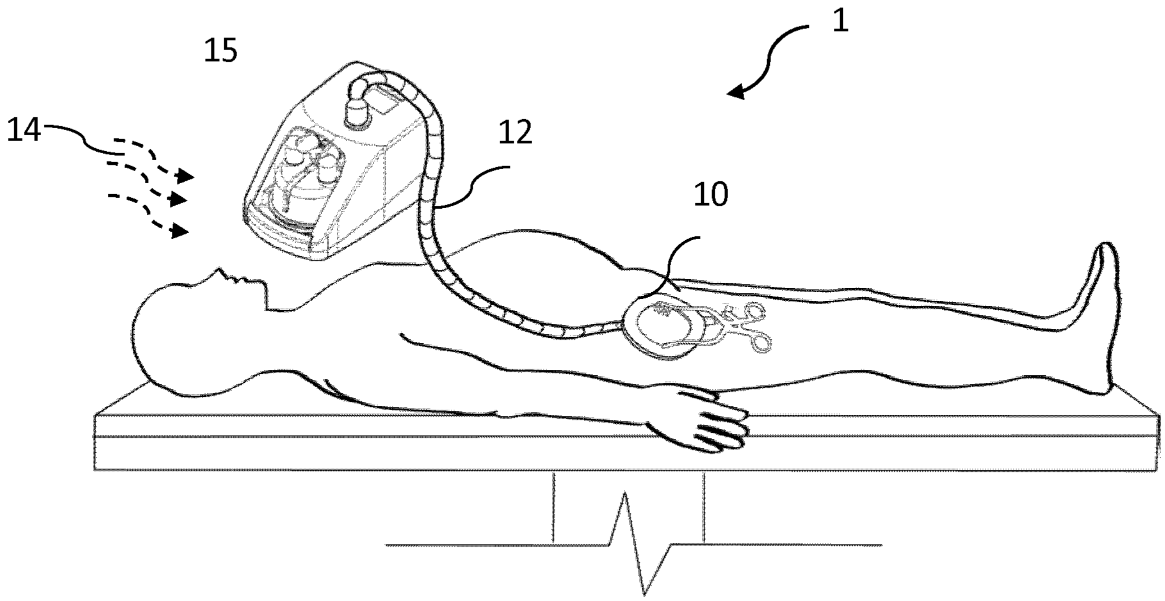
FIG. 1*a* is a view of a first embodiment of a system for wound management and/or treatment.
Figure 1B:
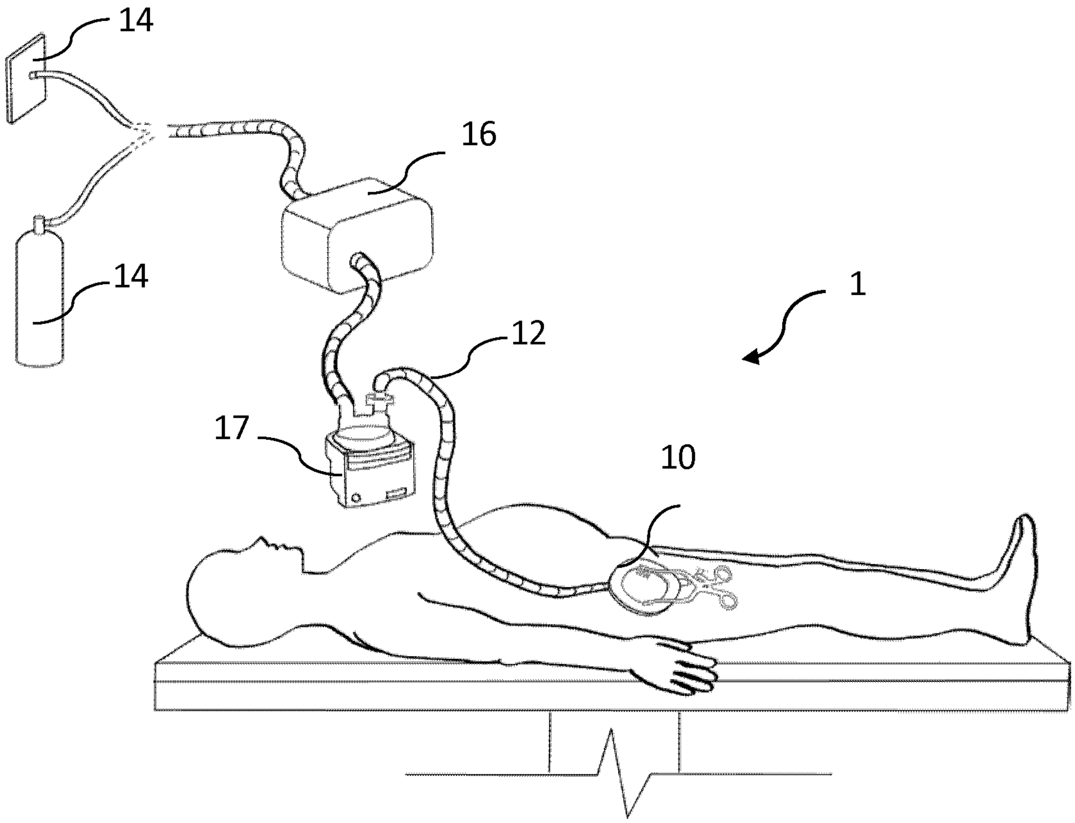
FIGS. 1*b* and 1*c* are views of further embodiments of a system for wound management and/or treatment.
Figure 1C:
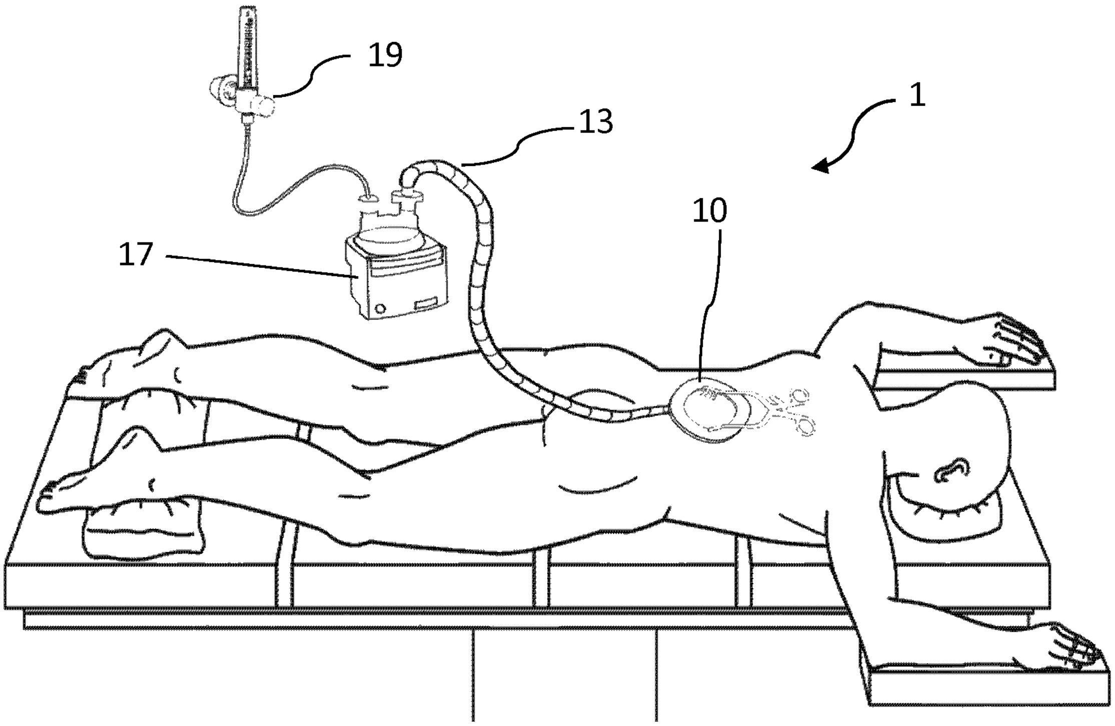

FIGS. 1*a*, 1*b* and 1*c* show embodiments of a system for treating and/or managing a wound. The system 1 of FIGS. 1*a* and 1*b* includes a patient interface 10 that is connected via a circuit 12 to a gas source 14. The gas source 14 provides a gas to the patient interface 10. The gas source 14 may take a number of different forms, including room air as shown in FIG. 1*a*, or a gas bottle or wall source as shown in FIG. 1*b*.

In the embodiment of FIG. 1*a*, the gas source in the form of room air 14 is entrained into a combined flow generator/humidifier unit 15. Such a combined flow generator/humidifier unit 15 entrains room air and may mix it with a secondary gas via a separate inlet port on the device. The flow generator/humidifier unit 15 may be generally similar in function to an Airvo™ device, as offered commercially by Fisher & Paykel Healthcare Limited. In FIG. 1*b*, a flow controller 16 and humidifier 17 are shown as separate units. As depicted, the flow controller 16, which may be an insufflator or similar device, can receive gases from a gas source 14 in the form of a bottle or wall source. However, it is also possible to entrain air into the flow controller 16 such that it also functions as a flow generator, and to mix the entrained air with other gases. In any of the embodiments of FIG. 1*a* or FIG. 1*b*, the gas may be conditioned if desired, for example heated and/or humidified, for delivery to the patient interface 10 and to the wound/wound edge.

In the embodiment of FIG. 1*c*, a gas source in the form of room air with a flow meter 19 is directed to humidifier 17. The gas may be conditioned by the humidifier 17, for example, heated and/or humidified, prior to delivery to the surgical site or wound. The gas may be delivered to the patient interface 10 via a suitable tube or conduit 13. The tube or conduit may be actively heated and/or thermally insulated, to maintain temperature and/or humidity of the gas until it is delivered to the patient interface 10. In the embodiment shown, the patient interface 10 is in use for an orthopaedic surgical procedure, namely a spinal surgical procedure.

The system 1 is shown in use in a surgical procedure on a patient in each of FIGS. 1*a*, 1*b* and 1*c*. In FIGS. 1*a* and 1*b*, the patient is lying in a supine position on an operating table for ease of illustration. In FIG. 1*c* the patient is lying in a face down position on an operating table. However, the position of the patient is, in practice, dependent on the procedure to be performed and in some orthopaedic procedures, for example, the limbs of a patient may even be moved during the procedure. The patient interface 10 is positioned on the patient at the site of the surgical operation such that, in use, it surrounds the surgical site at which an incision will be made to create an open wound. It will be understood, however, that in some instances of surgery, for example following a trauma, a wound may already exist. In this event, the patient interface 10 is positioned on the patient around the existing wound. Accordingly, whilst the patient interface 10 is shown placed on a substantially horizontal surface of the patient's body, it need not be in order to perform its function.

Figure 2:
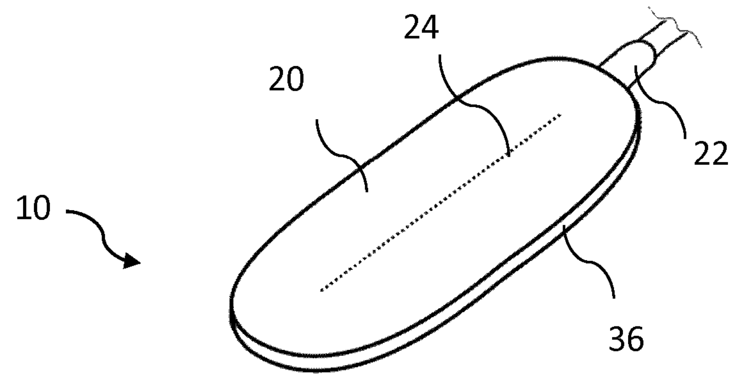
FIG. 2 is a perspective view of an embodiment of a patient interface.

The patient interface 10 may take various forms, described with reference to example embodiments shown in FIGS. 2 to 23 and FIGS. 25 to 50 below. In each of the embodiments, the patient interface 10 has an interface body 20, e.g. as seen in FIG. 2, that comprises a gas inlet 22 through which gases enter the interface body 20. The patient interface also includes a first gas flow path 100, seen in FIGS. 10-23, and a second gas flow path 102. The first gas flow path 100 is positioned in fluid communication with the gas inlet 22 and also with the second gas flow path 102.

The first gas flow path may have a first flow resistance and the second gas flow path may have a second flow resistance. The second flow resistance may be overall greater than the first flow resistance. The flow resistance need not be constant throughout the first gas flow path and the second gas flow path. For example, the flow resistance may not be uniform throughout the first gas flow path if the flow path itself is not constant throughout.

The flow resistance may not be uniform in cross-section throughout the second gas flow path if the flow path includes pockets or obstacles that might affect flow resistance, as discussed below. Overall, the second flow resistance is greater than the first resistance. In an embodiment, the second flow resistance is greater than the first resistance when taking a cross-sectional slice through the patient interface that is parallel to the direction that the gases exit the diffuser. In this manner, gases entering the gas inlet 22 flow easily through the first gas flow path 100 and then pass into the second gas flow path 102 where the gases meet with higher resistance as will be explained herein.

The interface body 20 includes a portion made from a porous or open cell material that acts to diffuse the gas, in use, around the periphery of a wound edge. The porous or open cell material may be stretchable. For example it may be conformable or pliant such that it may conform to the shape and/or contour of a patient's body. The porous or open cell material is referred to throughout the specification as the diffusing material portion. Suitable diffusing materials include open cell foam made from expanded polyethylene, polyurethane, silicone, rubber or the like, fabrics, weaves or cellular structures such as corn starch. The stretchable nature of the diffusing material allows it to conform to the contours of the patient's body and for it to be retracted, together with the wound itself, so as to deliver gas over the wound edge.

Figure 3A:
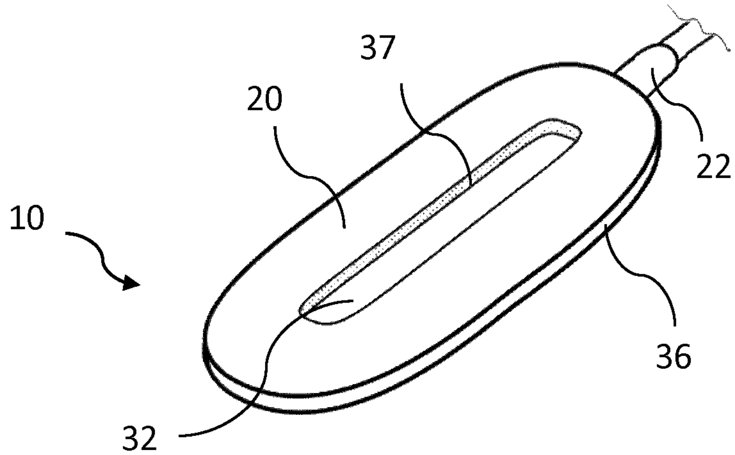
FIG. 3*a* is a perspective view of a further embodiment of a patient interface.
Figure 3B:
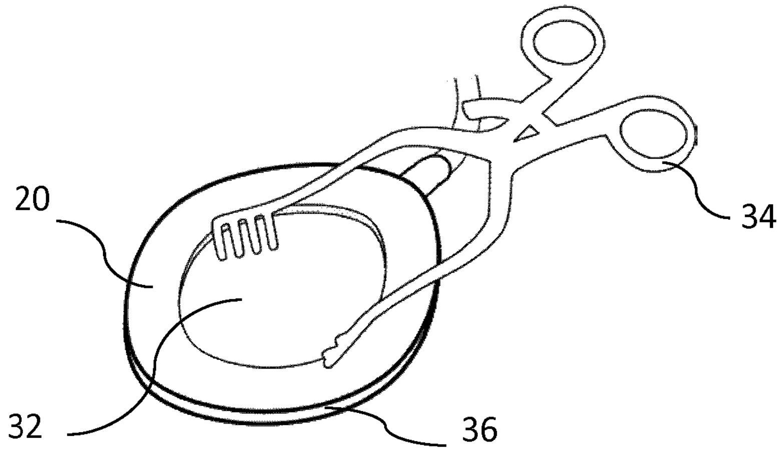
FIG. 3*b* is a perspective view of the patient interface of FIG. 3*a* in a retracted configuration.

The interface body 20 has a thickness that is significantly smaller in dimension than either its length or width dimension, as shown for example in FIG. 2 and FIG. 3*a* and FIG. 3*b*. In preferred embodiments the interface body 20 has a vertical height of not more than 30 mm, preferably not more than 20 mm, more preferably not more than 10 mm and even more preferably 6 mm, to reduce the potential for the interface body 20 to visually and/or physically interfere with the workflow of the surgeon. The patient interface 10 may be made in any suitable size and a footprint of the patient interface 10 is determined according to the expected required surgical incision length or to suit a particular type of surgery. For example, a patient interface at a large existing wound site or for a long surgical incision length must have a larger footprint than a patient interface intended for use in eye surgery. The patient interface 10 could be used on a very small incision (e.g. 1 cm) to a very large incision (e.g. in excess of 1 m from groin to ankle in a Femoral popliteal bypass) By way of further example, an incision for a total hip replacement surgery may be 12 cm long. For this size incision a slot length of approximately 16 cm would be preferable, providing 2 cm of space at each end of the wound should a larger incision need to be made for greater access.

The slot may be from 0 mm wide (where the incision is made through the diffusing material itself, exposing the diffusing edge) to 80 mm wide (providing up to 40 mm clearance from the edge of the diffusing medium to the wound edge). Preferably, where the slot is the pre-shaped slot 32, the slot may have a width dimension of from about 5 to 80 mm, or from about 5 to 60 mm, desirably 10 to 40 mm, more desirably 10 to 30 mm.

In some embodiments, the patient interface 10 includes a pre-marked visible incision guide line 24 on a top surface 26 thereof. The visible incision guide line 24 may be printed on the top surface 26 and/or it may be perforated to allow the guide line 24 corresponding to a desired wound length to be easily torn. Different sizes of interface body 20 intended for different surgical procedures may include different length visible incision guide lines 24.

In some embodiments, a pre-shaped slot 32 is cut into the interior of the interface body 20 as shown in FIG. 3*a* to allow unimpeded access to and vision of the incision site. This can be useful in surgical situations in which a surgeon wishes to pre-mark a surgical incision line. The slot 32 allows the interface body 20 to be applied to the patient prior to a surgical incision, without obscuring the marked incision line. The length dimension of the slot 32 is determined by the surgical procedure for which the particular size of interface body 20 is intended. Typically, the width of the slot 32 is small enough to maintain performance of the interface body 20 yet large enough for the interface body 20 to not impede, interfere or interact with the incision. For example, the width of the slot 32 may be sufficiently large so that the interface body 20 does not melt during an electrocautery procedure carried out via the slot 32. To assist a surgeon to make the correct or desired surgical incision at the wound site, the top surface of the interface body may have surgical incision length indicators 90 marked along at least one edge of the pre-shaped slot 32. An example embodiment of the surgical incision length indicators 90 marked either side of the pre-shaped slot 32 is shown in the patient interface 10 of FIG. 45. The surgical incision length indicators 90 may or may not be numbered and could be in any unit of measure, for example millimetres, centimetres or inches.

In use of the patient interface, the patient interface 10 is placed onto the patient, ideally before a surgical incision is made. The patient interface 10 can then be retracted along with the surgical site. FIG. 3*a* shows the slot 32 in an initial configuration or state. FIG. 3*b* shows the same patient interface 10 in which the slot 32 and the interface body 20 are in a retracted state, in which the slot 32 has been retracted into an expanded configuration with the use of a surgical retractor 34 or similar.

The porous stretchable material of the interface body 20 (e.g. the diffusing material), for example foam, is substantially elastic in some embodiments, such that it recoils or springs back into its initial shape once a force, for example the force applied by the surgical retractor 34, is removed. The diffusing material 104 is able to stretch or deform out with the wound retraction without significantly compromising the gas flow through the second gas flow path 102. Similarly, the diffusing material 104 can deform when forces are applied to it, such as from surgical instruments or surgeons hand during a surgical procedure.

Figure 46:
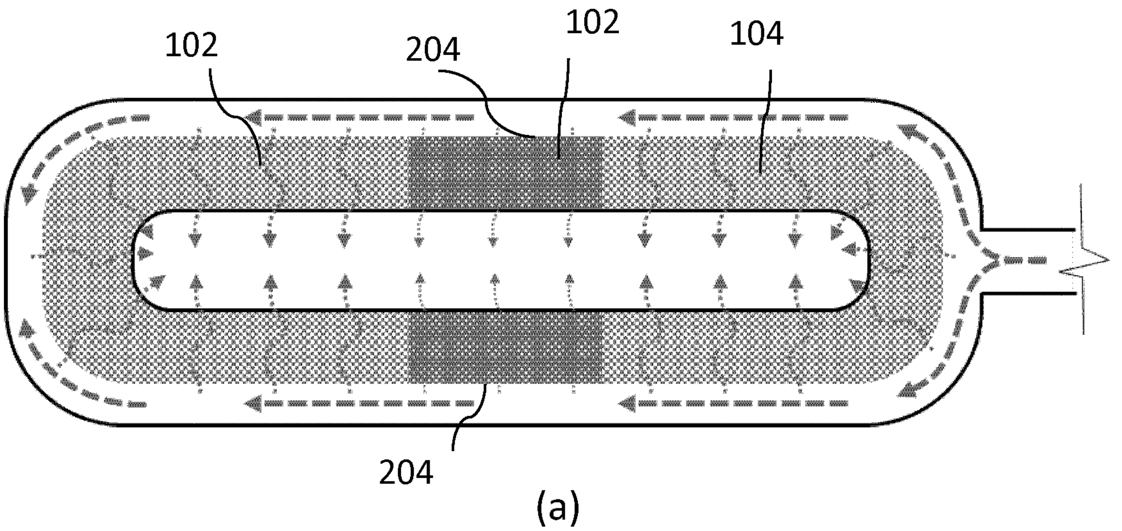
Figure 46:
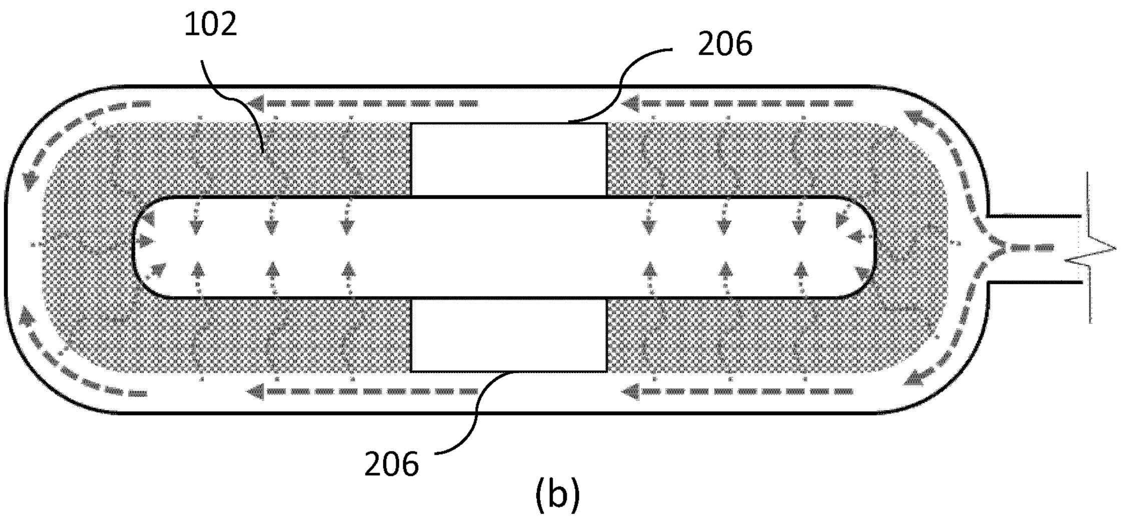
Figure 46:
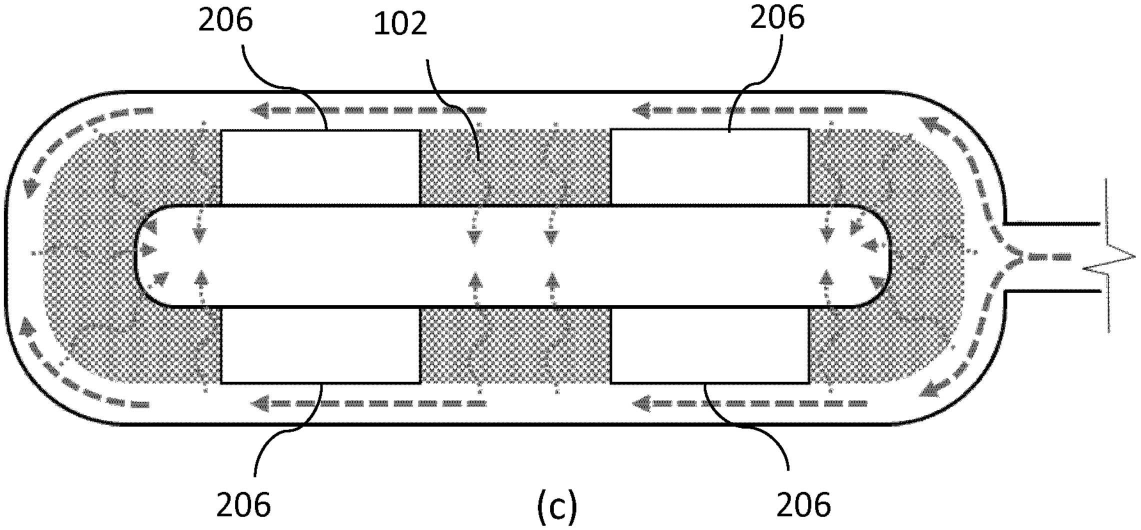

The porous or open cell diffusing material may have substantially uniform porosity or density along the length of the second gas flow path 102, or the porosity/density may vary. For example, the diffusing material 104 may include portions of denser foam material or a semi-impermeable or permeable foam portion or portions as seen in FIG. 46. FIG. 46*a* shows an embodiment of the patient interface 10 in which the interface body 20 includes a pair of generally opposing semi-impermeable portions 204 of the diffusing material 104. The semi-permeable portions 204 of the diffusing material 104 are located approximately mid-way along the length of the patient interface 10 and extend over a portion of the length of the slot 32 at which the retractor 34 is most likely to contact the patient interface 10. The portions of semi-impermeable or denser diffuser material 204 may prevent or mitigate disruption of flow path from compression by the retractor.

FIG. 46*b* illustrates an embodiment of the patient interface 10 in which the interface body 20 includes a pair of opposing substantially gas impermeable portions 206 of the diffusing material 104. The denser, substantially gas impermeable portions 206 may have an increased resistance to the force applied by the surgical retractor 34 as it presses against the sides of the slot 32, improving the robustness of the patient interface 10. The substantially gas impermeable portions 206 may occlude the gas flowing in the second gas flow path 102, however may assist in mitigating deformation of porous foam by the retractor 34. In this embodiment, the disruption of flow in the second gas flow path 102 is controlled rather than incidental from compression of the diffusing material 104 that may otherwise occur during use of the surgical retractor 34.

The interface body 20 may include multiple instances of the semi-impermeable portions 204 or substantially gas impermeable portions 206 along each side of the slot 32 to increase the robustness of the patient interface further. For example, the interface body 20 may include two spaced apart opposing pairs of substantially gas impermeable portions 206 along each side of the slot 32 as shown in FIG. 46*c*. This embodiment may be used where the surgery is expected to require the use of two or more surgical retractors 34 at different portions of the length of the patient interface 10. The semi-impermeable portions 204 or substantially gas impermeable portions 206 may be placed, for example, at several spaced locations along a 16 cm length slot required for hip surgery. Whilst FIGS. 46*a-c* show the semi-impermeable portions 204 and the substantially gas impermeable portions of the interface body as extending across the entire width of the second gas flow path 102, they may occupy only a portion of the second gas flow path 102 such that the density or porosity of the second gas flow path 102 varies between the first gas flow path 100 and the slot 32.

The semi-impermeable portions 204 and/or the substantially gas impermeable portions 206 of the interface body 20 may be made of a material other than the diffusing material 104, for example a separate foam component other material component that is suitable for resisting the force applied by the surgical retractor 34.

The support structure 112 is structured and/or configured to allow the patient interface 10 to bend or deform to take on a different shape but maintain an essentially constant cross section and flow resistance through the first gas flow path 100.

The first gas flow path 100 and the second gas flow path 102 have differing deformation properties. For example, the diffusing material portion 104 will deform in almost all directions when a force is applied to it. However, the support structure 112 will substantially resist or allow deformation in certain directions. For example, the support structure resists compression in a vertical direction but allows longitudinal compression. This allows the support structure 112 to maintain the first gas flow path 100 open. The first gas flow path 100 may be maintained open with a substantially constant cross section.

FIG. 4 shows an embodiment of the interface body 20 in which the pre-shaped slot 32 is adjustable in length by including perforations defining portions 42, 44 that can be optionally torn out to increase the length of the slot 32 according to the desired or intended wound size. The pre-shaped slot 32 may be similarly adjustable in width and/or diameter.

The interface body 20 shown in FIGS. 2, 3 and 4 is generally an elongate oval shape, with the inlet 22 positioned at one end thereof. However, embodiments of the interface body may be pre-shaped differently, e.g., in a round, oval or irregular configuration. The shape may be selected to fit a pre-existing chronic wound of any shape or size. In FIG. 5*a* the interface body 20 has a pre-shaped oval shape. FIG. 5*b* shows an embodiment of the interface body 20 which has a pre-shaped round or circular shape and a circular slot 32. Two concentric perforation lines surround the circular slot 32 so that the size of the circular slot 32 can be increased if desired by tearing out the portions 52, 54 defined by the perforations.

Figure 21:
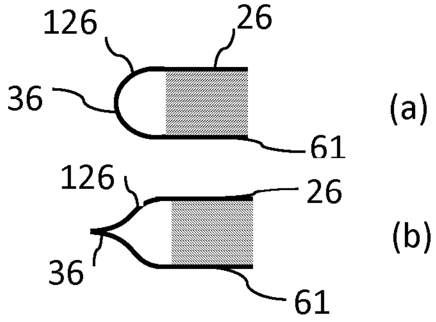
FIG. 21*a*-*b* are partial cross-sectional views of embodiments of a patient interface showing two options of a configuration of an outer membrane of the patient interface.
Figure 22:
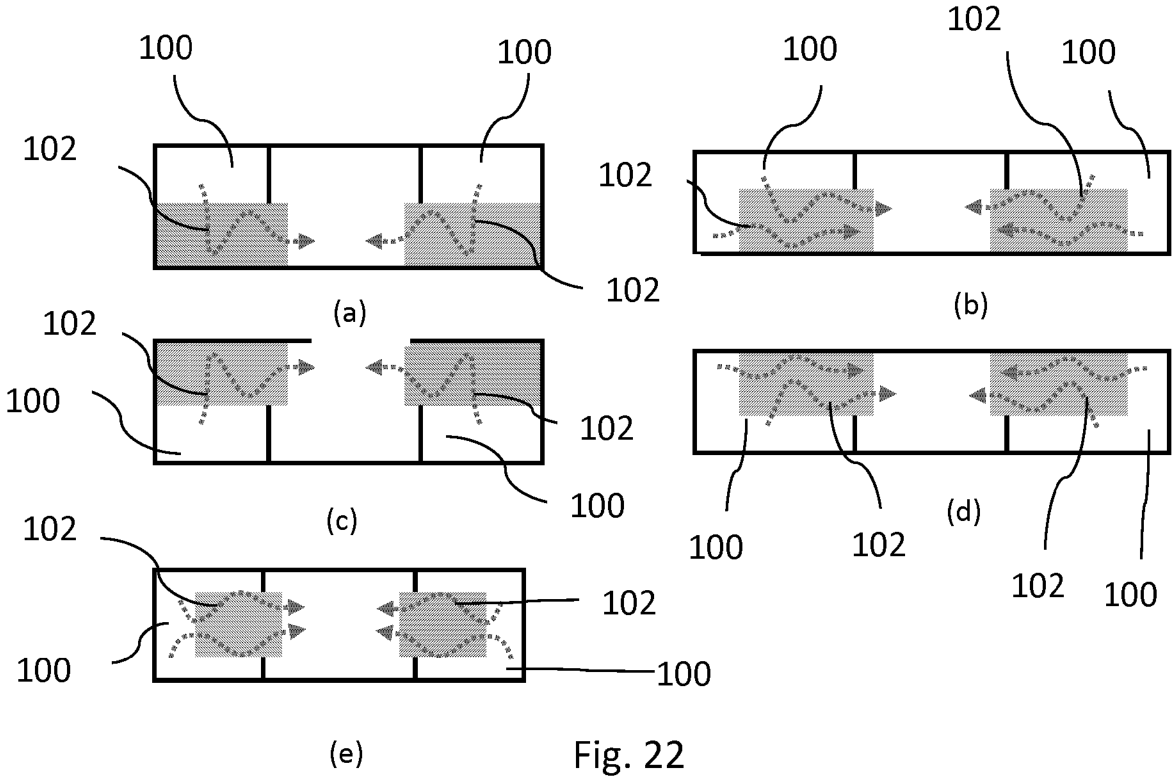
FIGS. 22*a*-22*e* are schematic cross-sectional views of an embodiment of a patient interface with different positional configurations of first gas flow path and diffusing material portion.

As best illustrated in FIG. 12*b* and in FIG. 21, the top surface 26, outer peripheral surface or surfaces 36 and optionally a bottom surface 61 of the interface body 20 are sealed by a skin or outer membrane 126 that may be produced inherently as a result of the moulding process of the foam body 20, or which may be formed by over moulding or by a film material that is adhered to the interface body 20. Alternatively, the outer membrane 126 can be adhered to or otherwise placed on to and around the diffusing material portion 104 after that part has been made. The outer membrane 126 of the interface body 20 may be translucent or transparent at least to allow visibility into the first gas flow path 102 and/or the diffusing material portion 104, as well as visibility of any condensate that may build up inside the patient interface 10 that may adversely affect its performance.

The wall, outer membrane or skin 126 may seal the open cell foam or other porous diffusing material portion 104 of the interface body 20 from the atmosphere such that gas cannot pass through those surfaces. Alternatively, the outer membrane 126 may be at least partially permeable to moisture, for example at least a portion of the outer membrane 126 defining the first gas flow path 100 may be permeable to moisture. That is, it may provide a liquid barrier yet be breathable/allow moisture vapour transmission. The outer membrane 126 may have a high moisture vapour transmission rate to allow water vapour in the patient interface 10 to diffuse out through the outer membrane 126 so as to prevent or at least mitigate the possibility of the water vapour condensing into liquid water within the first gas flow path 100. Accordingly, condensation within the device may be minimised. The outer membrane 126 may be made of a translucent or transparent film such as a polyurethane film. The outer membrane 126 may have a moisture vapour transmission rate that is at least a proportion of, or greater than, a rate of condensation build-up in the interface body 20 or first gas flow path 100.

In some embodiments, for example the embodiment of FIG. 3*a*, the only surface of the open cell foam or other diffusing material portion 104 that is open to the atmosphere is the inner surface 37 that defines the slot 32 or which is created by an incision cut through the interface body 20 by the surgeon if no pre-shaped slot 32 is present in the interface body 20. The inner surface 37 therefore defines an outlet of the interface body 20 and of the patient interface 10. However, in some other embodiments that are described later, other surfaces of the diffusing material portion 104 may be fully or partially exposed to the atmosphere such that those surfaces too form part of the outlet of the interface body 20.

Figure 6A:
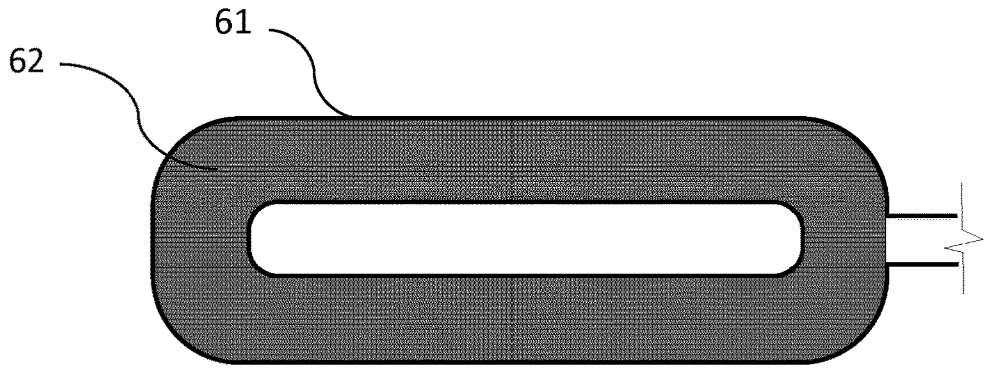
FIG. 6*a*-6*d* are schematic bottom views of embodiments of a patient interface having an adhesive backing.
Figure 6B:
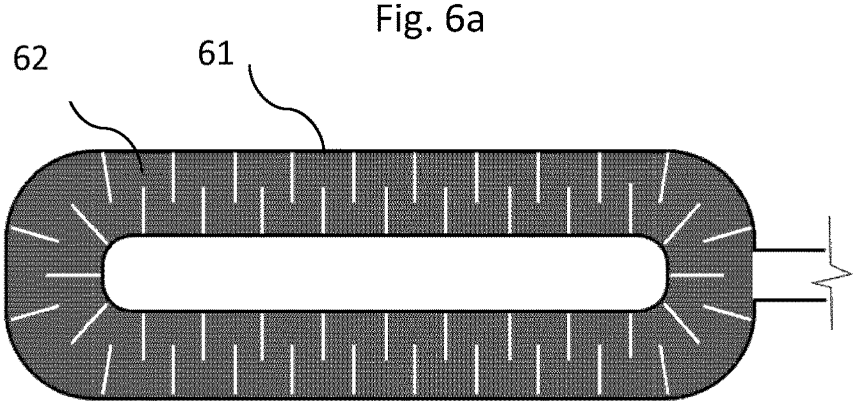
Figure 6C:
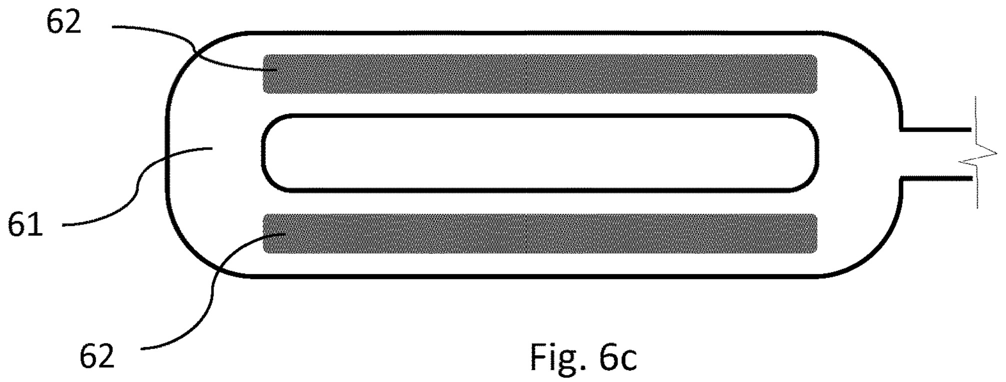

A biocompatible adhesive backing material 62 may be applied to a bottom surface 61 of the interface body 20 to affix the patient interface 10 to the skin of the patient or to a surgical dressing. FIGS. 6*a*-6*c* show three different adhesive configurations on the bottom surface 61 of the interface body 20 of the embodiment of FIG. 2. The adhesive material may be applied over the entire bottom surface 61 or over one or more portions of the bottom surface 61 of the interface body 20.

Figure 6D:
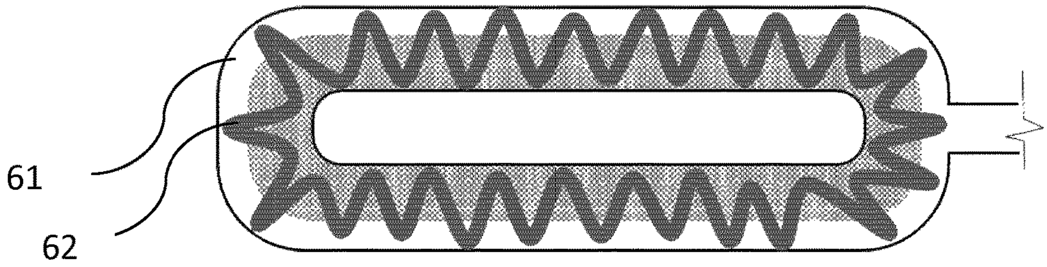

In FIG. 6*a*, the adhesive backing material 62 or layer is applied over the entire bottom surface 61 of the interface body 20. In FIG. 6*b*, the adhesive 62 is applied to a portion of the bottom surface 61 which is divided up into multiple areas by at least one slit or slot such that the bottom surface 61 may substantially conform to an underlying curved surface, e.g. the skin of a patient. This configuration can be advantageous in that the interface body 20 is not overly firmly adhered to the skin of the patient so as to avoid bunching of the interface body 20 or a compromised ability to conform to an irregular body or wound shape. In FIG. 6*d*, the adhesive backing material or layer 62 is applied on the bottom surface 61 in a regular or irregular winding or substantially wave shaped pattern. The width of the adhesive backing material or layer 62 may be decreased or increased according to the level of flexibility required to adhere to a particular part of the body that may have a greater or lesser degree of contouring. For similar reasons, the adhesive material 62 can be applied in discrete portions, for example the two strips shown in the embodiment of FIG. 6*c*.

The adhesive backing material 62 or layer may be provided as a separate layer, applied to the bottom surface 61 of the interface body 20. Alternatively, adhesive may be provided directly onto the bottom surface 61 of the interface body 20.

As an alternative to the adhesive material, the interface body 20 may be partially or substantially affixed to the patient by other non-adhesive mechanisms. Such mechanisms include applying a pad, for example but not limited to a silicone pad, to the bottom surface 61, which becomes sufficiently tacky or malleable to adhere to the patient via a suction effect. Other mechanisms include a gel fixing material that is tackified or other non-adhesive material having a physical and/or chemical structure that creates an adhesive effect.

Figure 7:
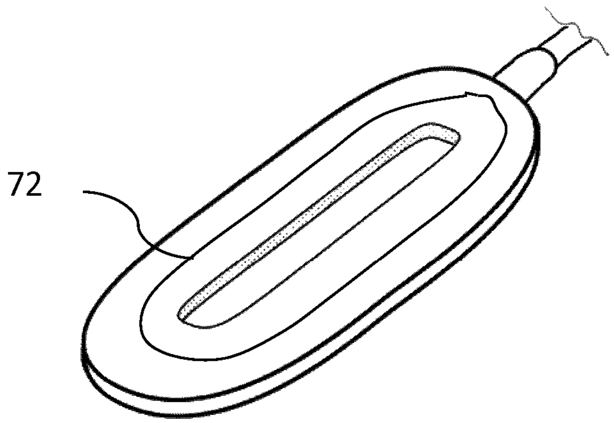
FIG. 7 is a perspective view of an embodiment of a patient interface having a support wire.

In some embodiments, for example the embodiment of FIG. 7, the patient interface 10 also includes a partially or fully circumferential malleable metal wire or strip 72 that can be bent or moulded or formed into a desired contour shape such that the interface body 20 retains this shape. Such a metal wire or strip can be integrally formed with the interface body 20.

Figure 8:
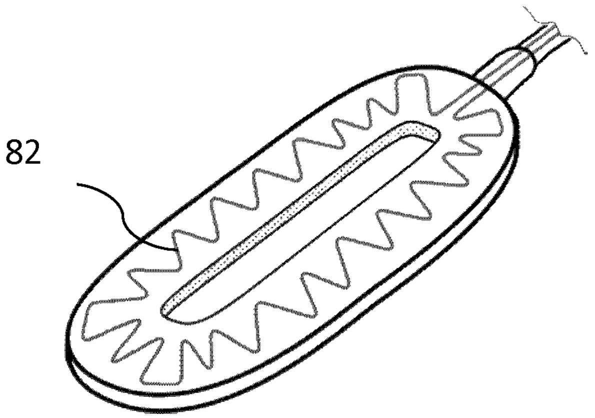
FIG. 8 is a perspective view of an embodiment of a patient interface having a heater element.
Figure 25A:
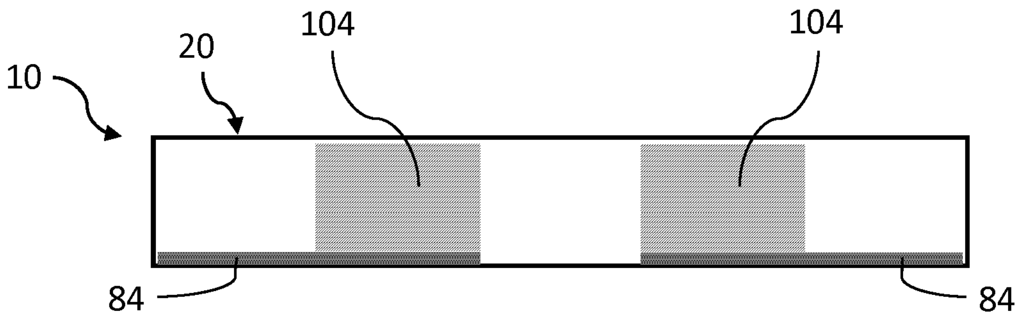
FIGS. 25*a*-25*c* are cross-sectional views of an embodiment of a patient interface including a heating pad or heated fabric surface.
Figure 25B:
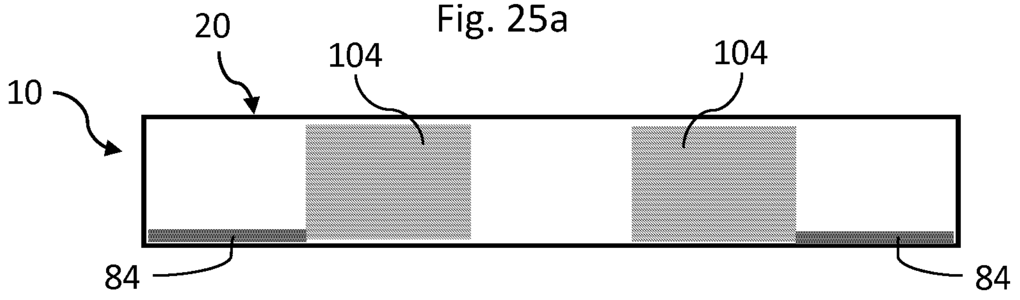
Figure 25C:
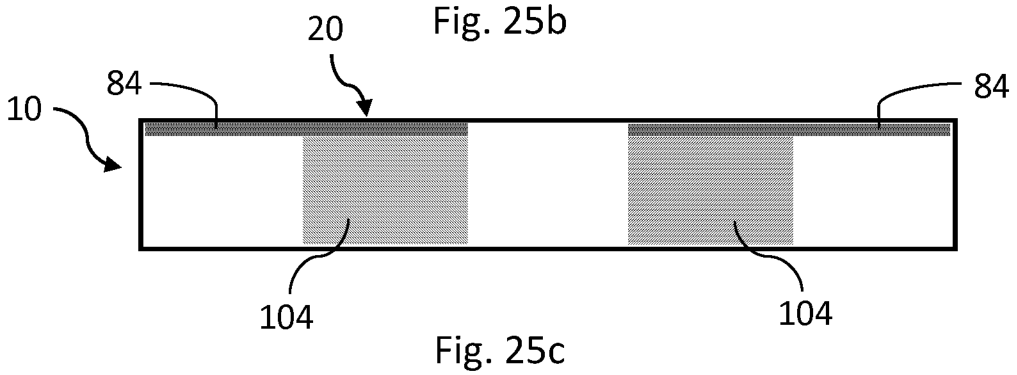

The patient interface 10 may include one or more heating elements, for example a heater wire loop 82 as shown in FIG. 8, or one or more pads or fabric surfaces 84 as seen in FIGS. 25*a*-25*c*. The use of heating elements and/or heating pads or fabric surfaces reduces condensation of water vapour in the patient interface 10. It also delivers additional warmth to the wound, for example to help maintain gas temperature and/or maximise humidity. The heating element 82 or heating pads/heated fabric surfaces 84 can be positioned on top of the interface body 20 as shown in FIG. 25*c*, on the bottom surface 61 as shown in FIG. 25*a*, or on both top of the interface body 20 and bottom surface 61, or sandwiched between layers of foam and/or membrane or film, or may be overmoulded onto one or more components of the patient interface 10. The heating elements 82 and/or heating pads or heated fabric surfaces 84 may be present in the first gas flow path 100 or, in the case of the heater wire loop 82, may pass within the diffusing material portion 104. With reference to the embodiment of FIG. 8, the heater wire loop 82 passes through the circuit 12 into the gas inlet 22 and into the interface body 20 where the loop surrounds the pre-shaped slot 32. The heating may be achieved with an electrically conductive housing, heating pads 84 positioned either side of the diffusing material portion 104 or with the use of electrically conductive foam in the interface body 20. In the latter example, the electrically conductive foam is isolated from the skin of the patient in use. In one embodiment, an electrical connection is made at a connection of the patient interface 10 to the circuit 12. The connection may facilitate an identification that a patient interface 10 has been connected with a circuit 12 and to identify the interface 10 using the known electrical resistance of a heater wire 82 used within a particular patient interface 10.

In FIG. 25*a*, the heating pad or pads 84 are positioned on a bottom surface 61 of the patient interface. The heating pads 84 extend over the first gas flow path 100 and also over the diffusing material portion 104. A single heating pad or surface 84 may cover this entire surface area, or alternatively a number of discrete heating pads 84 may be used. In FIG. 25*b*, the heating pad or pads 84 are positioned only at the portion of the bottom surface 61 that corresponds to the first gas flow path 100. In another embodiment (not shown), the heating pads may extend over the surface area corresponding only to the diffusing material portion 104. It is envisaged that any desired extent of the bottom surface 61 of the patient interface 10 may be covered with one or more of the heating pads 84. As mentioned above, positioning the one or more heating pads 84 on the bottom surface 61 of the patient interface conducts warmth to the patient during use and may actively warm the wound site. This may lead to increased perfusion, as warmer tissue results in vasodilation which results in more blood flow. This effect is believed to optimise surgical or post-surgical wound conditions and may also assist to mitigate surgical hypothermia, a drop in body temperature which can occur as an effect of surgery when anaesthetic drugs and/or exposure of the skin for long periods of time during surgery result in interference with normal temperature regulation before, during, and/or post-surgery.

In FIG. 25*c*, the at least one heating pad or fabric surface 84 extends over a top surface of the interface body 20. This configuration may be advantageous for minimising condensation in the patient interface 10. The bottom surface 61 is already somewhat insulated from heat loss by being in contact with the patient. Heating the top surface therefore eliminates the cold surface on the top on which condensate may form. This configuration furthermore allows for a higher heating element temperature as it is not in contact with the skin and is therefore less likely to burn the skin. However, any combination of the embodiments of FIGS. 25*a* to 25*c* may be implemented.

The heating pads 84 may be made of a padding in which a heated filament or wire is distributed through the padding underneath the surface. Alternatively, a conductive yarn may be knitted into a heated textile to provide a heated fabric surface 84. A known type of heated fabric material is the 'SEFAR PowerHeat NT™ fabric' made of polyethylene terephthalate (PET) monofilaments and conductive fibres. The heated fabric surface 84 may be similar in function to this fabric whilst being adapted as may be required to ensure it is suitable for and safe for use during surgery.

Figure 26:
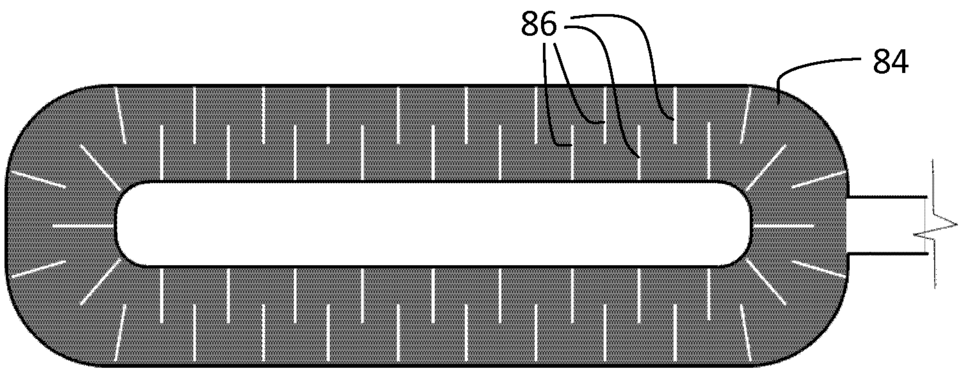
FIG. 26 is a top or bottom view of a heating pad or heated fabric surface applied to a patient interface.

In an embodiment, the one or more heating pads or heated fabric surfaces 84 is divided up into multiple areas by at least one slit or slot 86. As shown in FIG. 26, the one or more heating pads or heated fabric surfaces may be divided up into multiple areas by an alternating pattern of slots or slits 86, configured to allow or increase flexibility of the patient interface 10 so that it may conform to the contours of the body in use.

Figure 9:
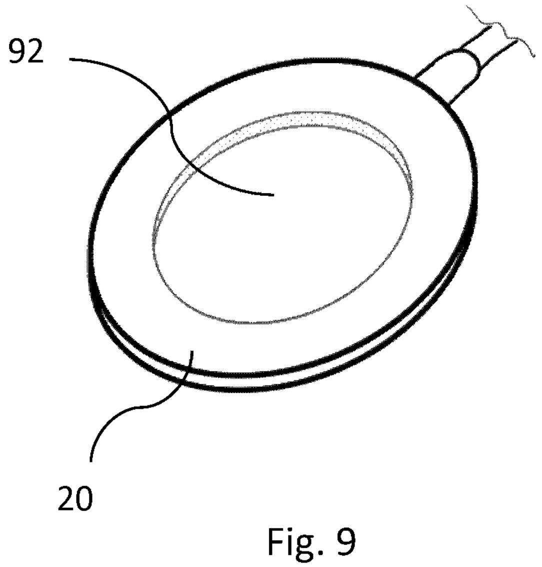
FIG. 9 is a perspective view of an embodiment of a patient interface including a transparent film.

FIG. 9 shows an embodiment in which a transparent film 92 is provided for application over the interface body 20, particularly but not exclusively during a post-operative wound management phase, to assist the healing process. The transparent film 92 seals in moisture to prevent desiccation of the wound and heat loss due to evaporative cooling. The transparency of the film 92 allows for the wound to be viewed and/or for its health to be visually monitored without needing to remove the film, which might disturb the healing process. In some embodiments, the transparent film 92 is removable if necessary so that the wound can be attended to without the need to remove the entire patient interface 10 from the wound site. In other embodiments, the transparent film 92 is not easily removable from the patient interface 10, which may have performance benefits in maintaining the gas flow near the wound during a surgical procedure. For example, the transparent film 92 may be non-removably attached to the top surface 26 of an embodiment of the patient interface 10 that includes the pre-shaped slot 32, such as in FIG. 9. An incision is then made through the transparent film 92 but not through the diffusing material portion 104. The transparent film 92 may then create an overhang that extends over the pre-shaped slot 32 beyond the diffusing material portion 104, which may assist in directing gas flow exiting the patient interface 10 downward toward the wound. An example of a patient interface 10 having an outlet configuration that produces a similar effect is shown schematically in FIG. 20*c*.

An important aspect of the patient interface 10 and system 1 of the present disclosure is that of aiming to deliver, as far as possible, an even distribution gas flow at the inner surface 37 of the patient interface 10. An even distribution of flow at the inner surface 37 may create a gas curtain or blanket around the wound site that forms a protective microenvironment over the wound site and may prevent it from drying out or cooling. FIGS. 10 to 23 illustrate various embodiments of configurations of the patient interface 10 that aim to deliver a more even flow.

FIG. 10 is a sectional view of an embodiment of the patient interface 10 in which the first gas path 100 is arranged peripherally around the diffusing material portion 104 (e.g. open cell foam) of the interface body 20 so as to substantially encompass it. The peripheral first gas path 100 allows a gas or gases entering the inlet 22 to pass freely around the diffusing material portion 104 providing for a more even distribution of the gas flow from the gas source 14 to an outer periphery 106 of the diffusing material portion 104 of the interface body 20. The gas flows through the second gas path 102 i.e. from the outer periphery 106 of the diffusing material portion 104, through the diffusing material, to be delivered in a more even distribution to the outlet at the inner surface 37 of the diffusing material portion 104. The second gas path 102 is formed through the porous, open structure of the foam or other open cell material, which presents a higher flow resistance to the gas flow than does the first gas flow path 100.

The first gas flow path 100 may be entirely vacant as seen in FIG. 10 or it may be filled with a stretchable porous material of substantially lower flow resistance than the diffusing material so as to have a substantially lower resistance to the gas flow than the diffusing material. In the embodiment of FIG. 11, a support structure or scaffold structure 112 is positioned throughout the first gas flow path 100. The support structure 112 is configured to deform upon retraction of the patient interface 10, yet maintain a substantially flat profile. The support structure 112 is configured to maintain a cross-section of the first gas flow path that is substantially unaffected by retraction. Retraction of the patient interface 10 occurs with the retraction of a surgical incision or wound as the incision or wound edges are separated and held apart so as to access underlying organs or tissues. As the wound or incision is retracted, so too is the patient interface 10, including the support structure 112. The support structure 112 is configured to resist forces, such as compressive forces, such as may be applied by the pushing of the surgical retractor 34 laterally against the perimeter of the slot 32 of the patient interface 10 or by surgical instruments generally.

In the embodiment of FIG. 12, the support structure is in the form of a helical spring 122 positioned in the first gas flow path 100 around substantially the entire periphery of the diffusing material portion 104 of the interface body 20. Other variations are described below. Each of the variations supports the outer membrane 126 of the interface body 20 as illustrated in FIG. 12*b* and helps to retain the shape of the first gas flow path 100. The support structures 112, 122 also provide a structure around which a sealing film can be wrapped to form the outer membrane 126.

The inclusion of the support structure 112 or spring 122 as a support structure has an additional benefit. In use, the retractor 34 often places a considerable force on the wound edge to pull apart the wound edges so as to create sufficient physical access for the surgeon and surgical instruments. The force on the retractor 34 may collapse and occlude the first gas flow path 100. The spring 122 may have a sufficient spring force to physically resist being crushed and/or kinked whilst remaining flexible. The spring 122 can therefore maintain gas flow through the first gas flow path 100 in such a situation. The spring 122 may be made from a metal that can provide sufficient reinforcement against crushing or deformation, for example spring steel, which may be stainless or coated. In some embodiments, the spring 122 is formed from a medical grade stainless steel, however non-medical grade materials can also be used with an encapsulating coating that presents a biocompatible layer or sterility and corrosion barrier. The spring 122 may alternatively be made of a plastic or a combination of metal and plastic. If made from thermally conductive material, the spring 122 may have an appropriate resistance that allows the spring 122 to itself be the heater wire. The spring 122 may be a helically wound metallic wire. Its diameter may be selected to provide the desired support to the outer membrane 126 and it may be coated with a coating that allows the spring 122 to also function as the heater wire 82.

The spring 122 may have too low a resistance to also function as the heater wire 82. In this case, the spring 122 may include or comprise a heating element. Alternatively, the spring 122 may have an insulative coating that allows a second wire that has a resistance appropriate for use as the heater wire 82 to be winded with the spring 122 or passed through its coils. An example of a suitable insulative coating or casing is a thermoplastic sheath, such as a low density polyethylene (LDPE) sheath.

The spring 122 may be positioned over the outer surface of or in an inner bore of a flow director insert 124. The spring 122 and the flow director insert 124 may be held together by the overmoulding of the encompassing outer membrane 126 or the spring itself may be overmoulded onto or into the flow regulator insert 124. Alternatively, the outer membrane 126 can be adhered to or otherwise placed on to and around the diffusing material portion 104 after that part has been made.

The support structure 112 is designed to prevent crushing from the force of wound retractors and other surgical instruments, yet having a flexible structure so as to be conformable to the contours of the body surrounding the wound site and to deform with the wound edge when retracted without substantially affecting the first gas flow path and/or its flow resistance. In preventing the crushing of the support structure 112, the integrity of the first gas flow path 100 is maintained. The shape and structure of the support structure 112 is deformable under the application of laterally applied force e.g. as the patient interface 10 is retracted with the wound. The support structure 112 may be made with a number of geometrical features or repeating patterns to allow flexibility in one or more directions and/or rigidity in one or more directions.

The support structure may be made from any number of suitable materials e.g. polymer (nylon, polyurethane, PTFE, polypropylene), carbon fibre, or plant based materials, for example sugar cane plastic. The support structure 112 may be made from or include a material that is compatible with intra-operative imaging techniques. For example, the material may be free of metallic components such that the support structure 112 does not impede imaging of the surgical site, such as intra-operative imaging. Alternatively, the support structure 112 may comprise a material or element that can be viewed by imaging techniques. In some embodiments, another component of the interface 10 may comprise a material or element that can be viewed by imaging techniques.

Whilst providing the required structural integrity, the material of the support structure 112 may include at least portions that can be cut through by a simple instrument, e.g. surgical scissors. This may be required, for example, at the conclusion of a surgical procedure for removal of the patient interface 10 from the patient. Accordingly, the support structure may include one or more frangible or weakened portions to allow ease of cutting. The weakened or frangible portions may be marked on the support structure 112 or elsewhere on the patient interface 10, e.g. at a suitable position on the outer membrane 126, or otherwise made visible to the surgeon for ease of cutting. The support structure 112 may be substantially rectangular, circular, rhombus (or any shape) in cross section. FIGS. 27 to 43 and FIG. 47 illustrate various embodiments of the support structure 112 as described below.

Figure 27:
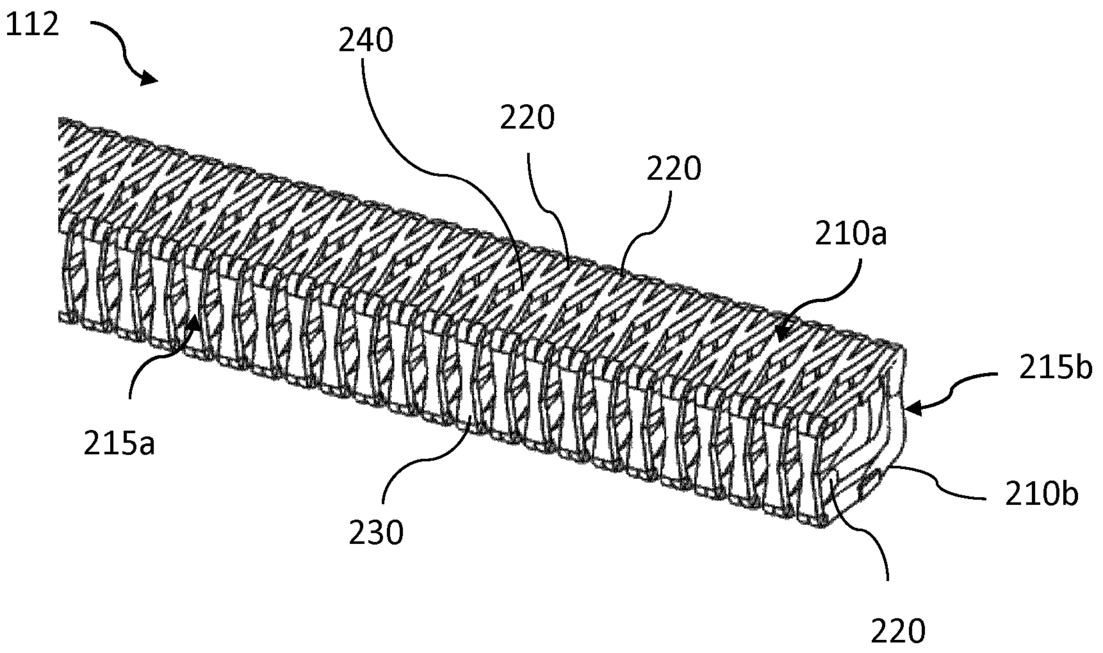
FIG. 27 is a perspective view of a support structure according to an embodiment of the patient interface.

In the embodiment of FIG. 27, the support structure 112 has a rectangular cross-section having a pair of opposing first sides 210*a*, 210*b* (the upper and lower sides as seen in FIG. 27) and a pair of opposing second sides 215*a*, 215*b* disposed substantially perpendicularly to the pair of opposing first sides (the vertical sides as seen in FIG. 27). The support structure 112 comprises a plurality of interconnected elements 220 arranged in a repeating pattern over a longitudinal axis of the support structure 112. The plurality of interconnected elements 220 includes a plurality of substantially X-shaped elements 220 extending in a repeating pattern along each of the pair of opposing first sides 210*a*, 210*b*. Adjacent X-shaped elements 220 share a vertically oriented connecting member 230 that extends substantially perpendicularly to the pair of opposing first sides 210*a*, 210*b* to connect the adjacent X-shaped elements 220 of an upper side 210*a* of the pair of opposing first sides to the corresponding adjacent X-shaped elements 220 of the lower side 210*b* of the pair of opposing first sides. The vertical connecting member 230 has a shape that tapers inwardly towards its mid-point from each of the upper side 210*a* and the lower side 210*b*. In the embodiment of FIG. 27, a point of intersection 240 of each of the plurality of substantially X-shaped elements 220 is substantially at a mid-point of each of the pair of opposing first sides 210*a*, 210*b*. The support structure 112 of this embodiment provides flexibility in three directions as the support structure 112 can be stretched longitudinally and bent laterally in both directions. Its structure also resists torsion. These properties of the support structure 112 allow a large conformability of the patient interface 10 to the retracted wound. In particular, the longitudinal stretch allows for the patient interface 10 to expand and conform with the wound as it is retracted.

Figure 28:
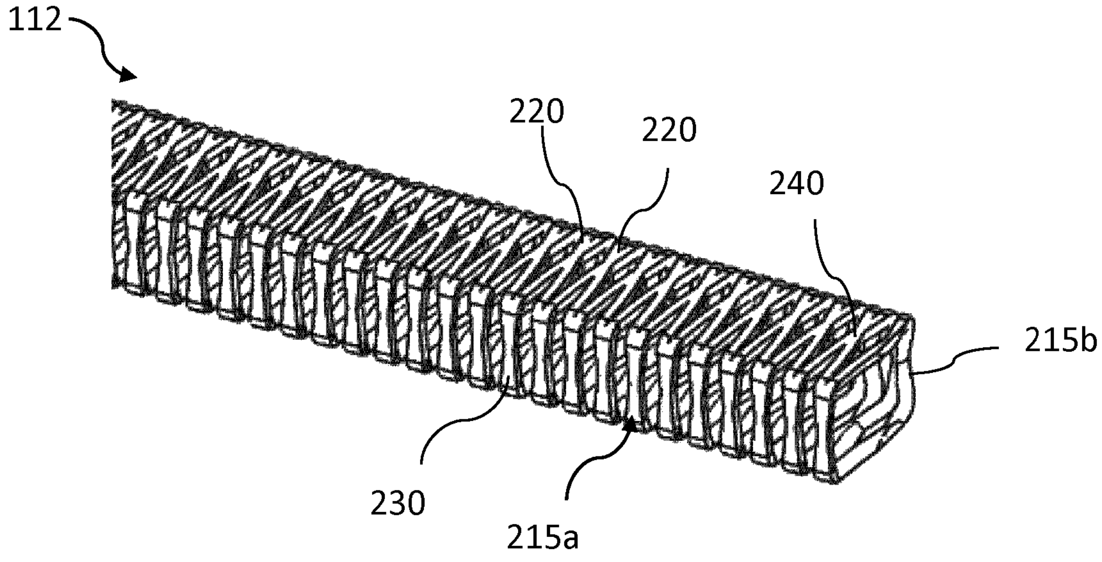
FIG. 28 is a perspective view of a support structure according to an embodiment of the patient interface.
Figure 29:
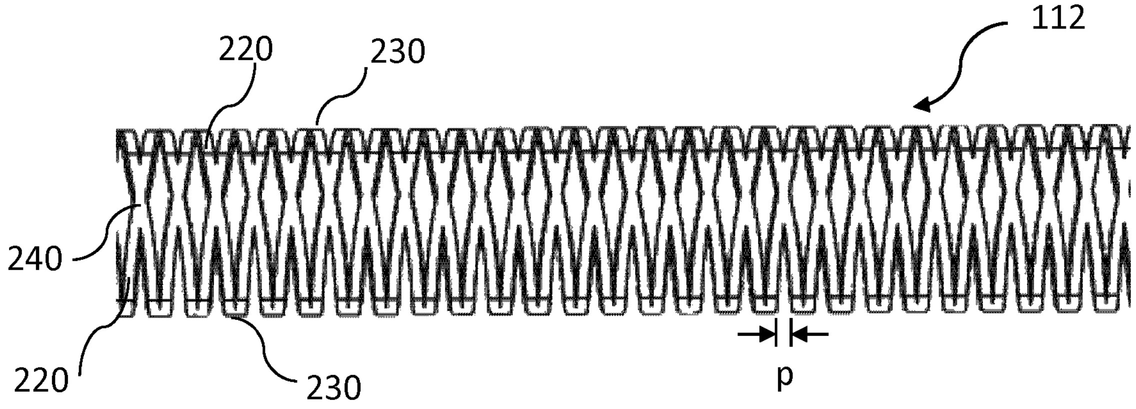
FIG. 29 is a plan view of the support structure of FIG. 28.

In a variation of this configuration shown in FIGS. 28 and 29, a point of intersection 240 of the plurality of substantially X-shaped elements 220 is offset from a mid-point of each of the pair of opposing first sides 210*a*, 210*b*. It is otherwise identical to the embodiment of FIG. 27. This configuration also has flexibility in three directions and resistance to torsion. However, this support structure 112 has more flexibility than that shown in FIG. 27 in bending in one horizontal plane direction, in which the connecting members 230 of the side 215*b* are bent towards one another, when viewed from above. This is due to the asymmetry of the X-shaped elements 220. This property of the support structure 112 may be advantageous as the support structure 112 will be bent around at least a partially circular shape at the distal end and/or proximal end of the patient interface 10 during use.

In the embodiments shown in FIGS. 27 to 29, a pitch (p) or distance between the connecting members 230 is shorter than or equal to the width of the connecting members 230. This configuration lends rigidity to the flexible structure for resisting lateral and vertical forces applied by the retractor 34 or other surgical instrument.

Figure 30:
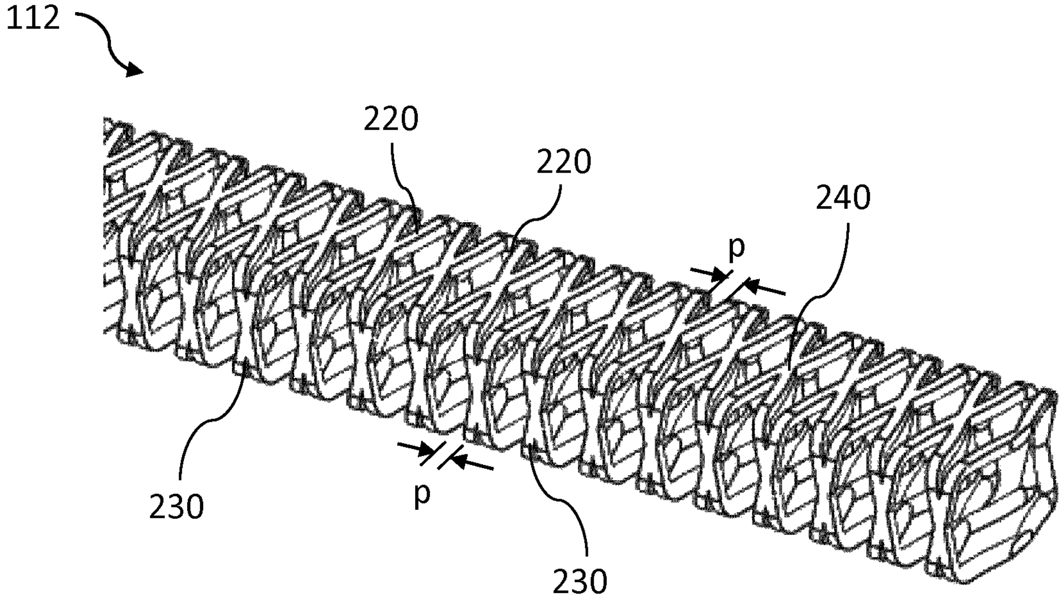
FIG. 30 is a perspective view of a support structure according to an embodiment of the patient interface.

FIG. 30 shows an embodiment of a support structure 112 having a wider pitch (p) between the connecting members 230 than that of the embodiment shown in FIG. 29. The connecting members 230 are also X-shaped. The X-shaped elements 220 of the upper side 210*a* and 210*b* have a larger angle of crossing than the X-shaped elements 220 of the embodiments of FIGS. 27 to 29. This embodiment provides a greater amount of flexibility to the support structure 112. This embodiment may have less crush resistance when compared with the support structures 112 of FIGS. 27 to 29. In each of the embodiments of FIGS. 27 to 30, the X-shaped elements 220 may have a thickness of about 1.5 mm. The connecting members 230 may be about 2.5 mm wide (i.e. extending longitudinally with respect to the longitudinal axis of the support structure 112) and may have a thickness of about 1.0-1.5 mm. The pitch between the connecting members 230 may be anywhere from 2 to 10 mm, or more preferably from 4 to 8 mm.

Figure 31:
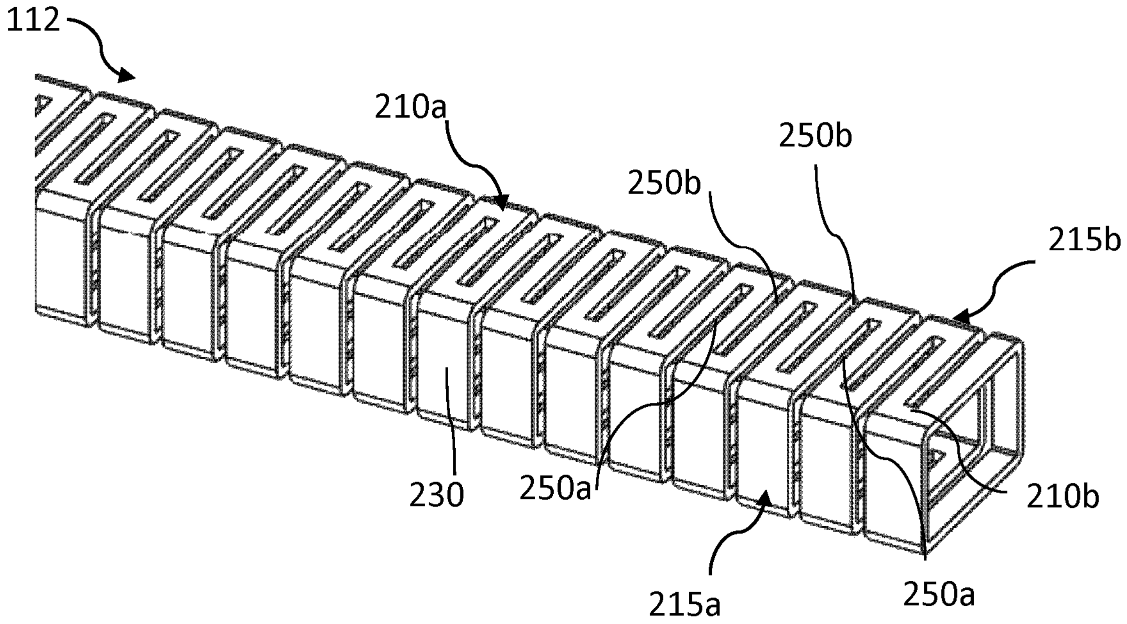
FIG. 31 a perspective view of a support structure according to an embodiment of the patient interface.
Figure 32:
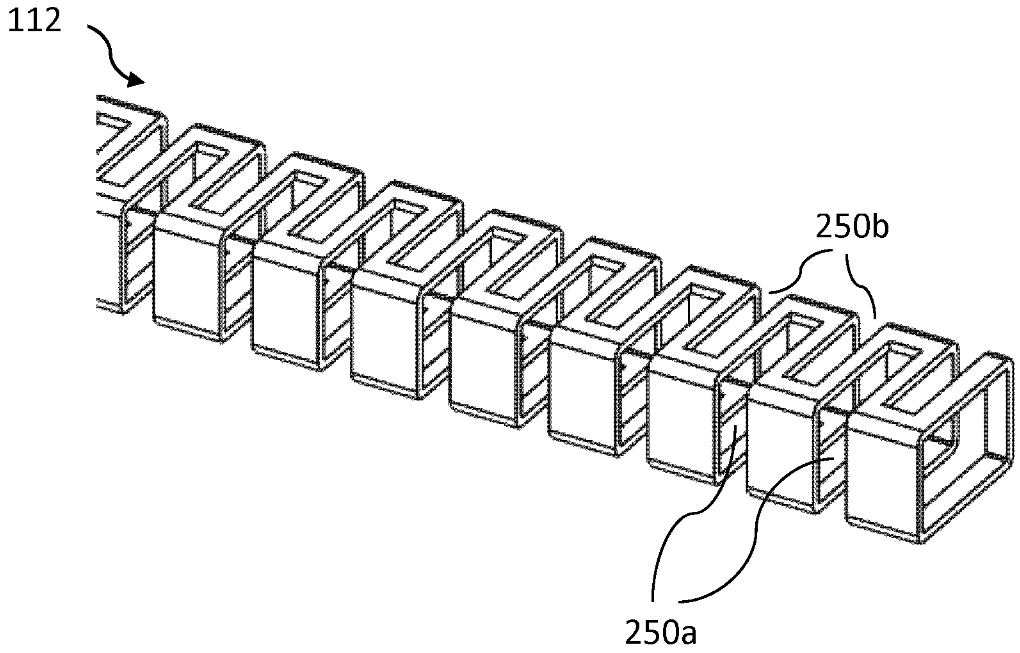
FIG. 32 is a perspective view of a support structure according to an embodiment of the patient interface.
Figure 33:
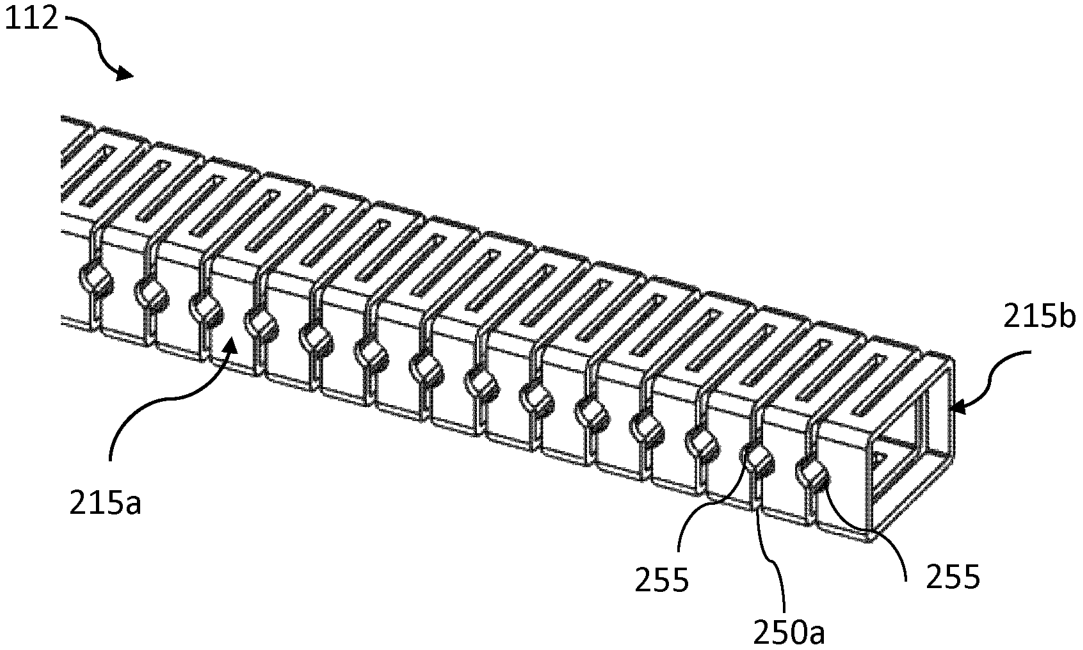
FIG. 33 is a perspective view of a support structure according to an embodiment of the patient interface.

FIGS. 31 to 33 show embodiments of a support structure 112 that utilise a repeating square wave pattern to achieve the desired rigidity of structure whilst providing a flexible structure. Each of the pair of opposing first sides 210*a*, 210*b* comprises structural portions 211 defining a repeating alternating square wave pattern, whereby each repeat of the square wave pattern includes a first slot 250*a* extending from one of the pair of opposing second sides 215*a* towards the other of the pair of opposing second sides 215*b* and an adjacent second slot 250*b* extending from the other of the pair of opposing second sides 215*b* towards the one of the pair of opposing second sides 215*a*. The degree of flexibility and crush resistance can be tailored by varying the width and/or pitch of the structural portions 211 of the sides 210*a*, 210*b* that define the slots 250*a*, 250*b* and effectively modifying the pitch of the repeating square wave pattern. For example, in the support structure 112 of FIG. 32, the structural portions 211 of the pair of opposing first sides 210*a*, 210*b* has a square wave pattern with a greater pitch than is shown in the support structure 112 of FIG. 31, as the longitudinal distance between the structural portions is increased. The increased pitch of the structural portions 211 results in wider slots 250*a*, 250*b*. The pitch of the square wave pattern may additionally or alternatively be varied by implementing a greater or lesser width of the structural portions 211 in the longitudinal direction of the support structure 112. Furthermore, the pitch of the square wave pattern may vary across the first opposing sides 210*a*, 210*b*.

FIG. 33 shows another embodiment of the support structure 112 that is identical to the embodiment of FIG. 31, with the addition of a notch or cutaway 255 in portions of the vertical second sides 215*a*, 215*b* either side of a slot 250*a*, 250*b*. The notch or cutaway 255 is circular in this embodiment. However, it may also be a diamond shape or other suitable shape. The cutaways 255 may be made in either or both of the vertical second sides 215*a*, 215*b*, however it is preferred to include the cutaways 255 on one of the second sides only to maintain the crush resistance of the support structure 112. The cutaways 255 function to maintain an open gas flow path through the patient interface 10 when the support structure 112 is in a bent configuration. For example, in FIG. 33 the cutaways 55 are shown in the second side 215*a*. When the supporting structure 112 is bent laterally to its full extent towards the second side 215*a*, the vertical slots 250*a* may be substantially or completely occluded when the vertical sections of the second side 215*a* abut, however the cutaways 255 function to maintain an open gas path from the first gas flow path 100 to the second gas flow path 102 through the diffusing material that lies adjacent to the supporting structure 112 when it is in situ in the patient interface 10. This embodiment may be used to particularly good effect at the inner side or second side 215*a* of the support structure 112 as it is bent around the distal end of the patient interface 10, as in FIG. 43. The support structure 112 may be fully bent around the radius, however gas will still pass through the inner side 215*a* of the support structure 112 to supply the diffusing material.

Figure 34:
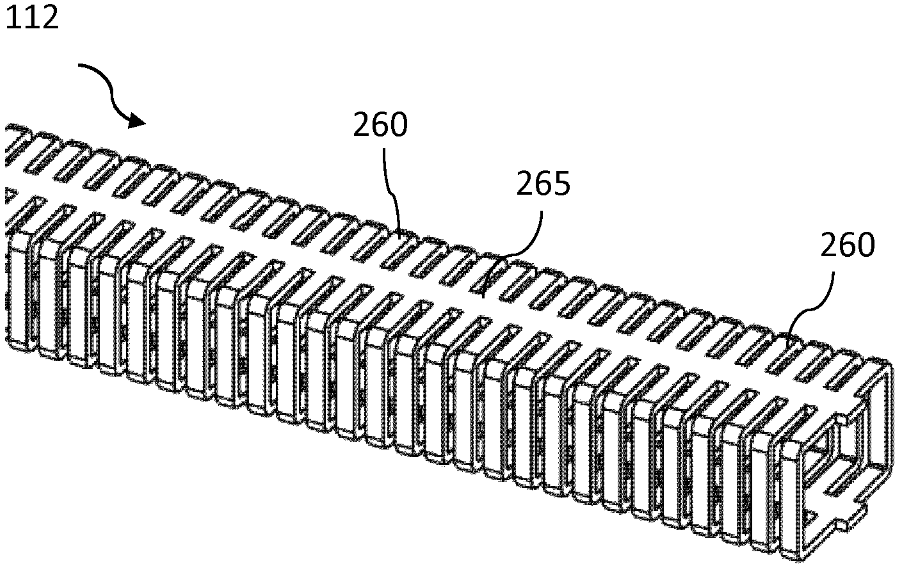
FIG. 34 is a perspective view of a support structure according to an embodiment of the patient interface.

The support structure of FIG. 34 comprises a repeating series of bands 260 of rectangular cross-section, that are interconnected by a central longitudinal spine 265 extending the length of the support structure 112 at a mid-point of each of upper and lower sides 210*a*, 210*b* of the support structure 112. The bands 260 are longitudinally separated from one another at a pitch that is narrower than the width of the bands 260, so as to form narrow slots between the bands 260.

The above configuration has a repeating pattern that provides flexibility in all planes whilst resisting both tension and compression and vertical bending. The spine 265 running down the centre of the upper side 210*a* and the lower side 210*b* may be made of the same material as the bands 260 of the support structure 112 or it may be made from an appreciably softer or more compliant material such as silicone, rubber or thermoplastic elastomer, to allow some vertical flexibility. A balance of vertical flexibility and resistance may be desired to allow the patient interface 10 to be conformed to the contours of the body yet resist crushing forces due to the retractor and/or other surgical instruments.

Figure 35:
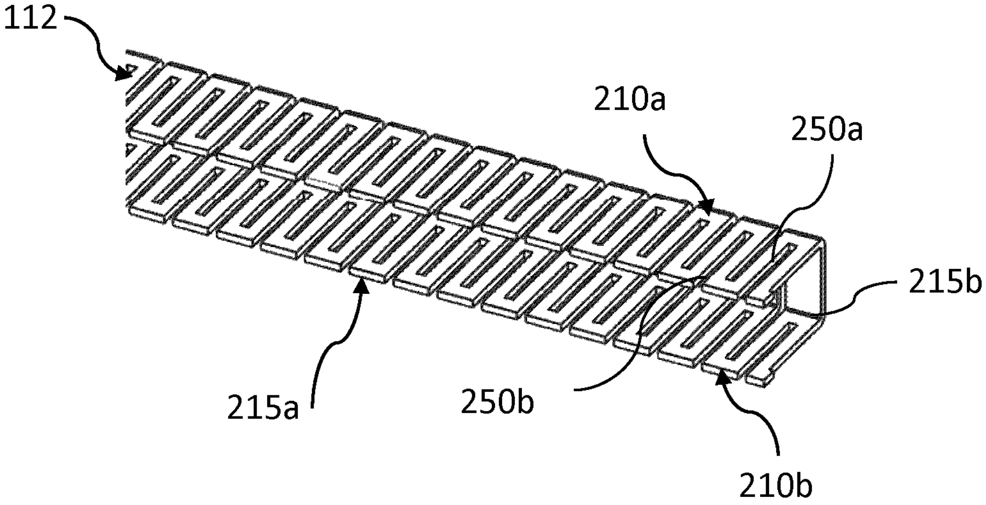
FIG. 35 is a perspective view of a C-shaped a perspective view of a support structure according to an embodiment of the patient interface.
Figure 36:
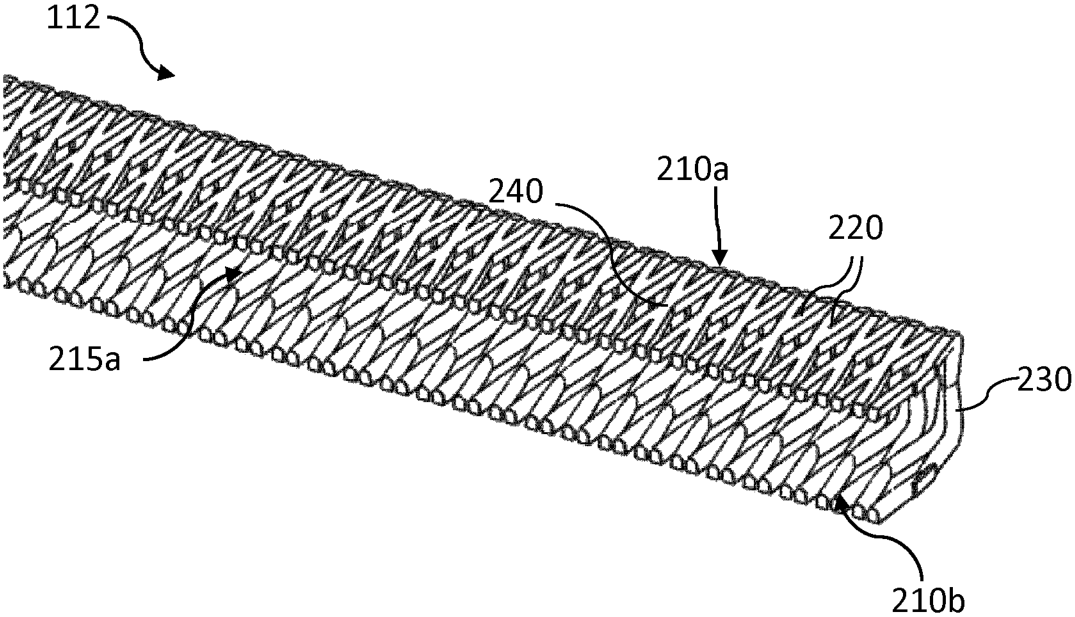
FIG. 36 is a perspective view of a further embodiment of a C-shaped support structure according to an embodiment of the patient interface.

FIGS. 35 and 36 each show examples of the support structure 112 having a substantially C-shaped cross-sectional shape. The remaining side of the structure remains open. The embodiment of FIG. 35 is otherwise identical to the embodiment of FIG. 31. Each of the pair of opposing first sides 210*a*, 210*b* comprises a repeating alternating slot pattern, whereby each repeat of the pattern comprises a first slot 250*a* extending from the only second side 215*b* towards the open side 215*a* and an adjacent second slot 250*b* extending from the open side 215*a* towards the single second side 215*a*. The embodiment of FIG. 36 is very similar to the support structure of FIG. 27, but the second side 215*a* remains open, having no support structure. A plurality of substantially X-shaped elements 220 extends in a repeating pattern along each of the pair of opposing first sides 210*a*, 210*b*. Adjacent X-shaped elements 220 share a vertically oriented connecting member 230 that extends substantially perpendicularly to the pair of opposing first sides 210*a*, 210*b* to connect the adjacent X-shaped elements 220 of an upper side 210*a* of the pair of opposing first sides to the corresponding adjacent X-shaped elements 220 of the lower side 210*b* of the pair of opposing first sides. The vertical connecting member 230 has a shape that tapers inwardly towards its mid-point from each of the upper side 210*a* and the lower side 210*b*. In the embodiment of FIG. 27, a point of intersection 240 of each of the plurality of substantially X-shaped elements 220 is substantially at a mid-point of each of the pair of opposing first sides 210*a*, 210*b*.

Figure 37:
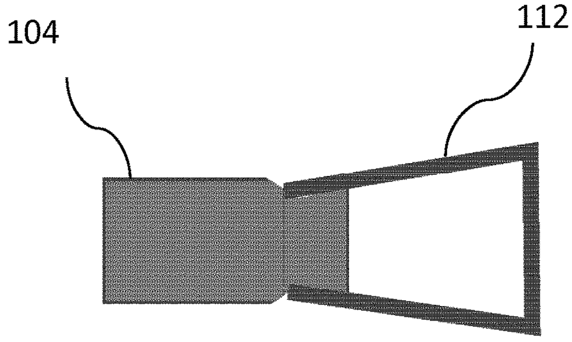
FIG. 37 is a partial cross-sectional view of a patient interface having a support structure with a C-shaped cross section, partially encapsulating the diffusing material.
Figure 38:
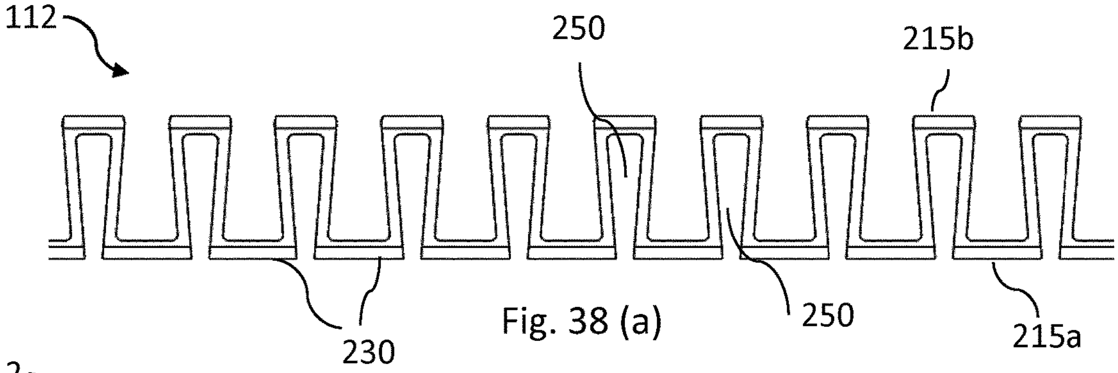
FIGS. 38*a* and 38*b* are a plan view and a perspective view respectively of a further embodiment of a support structure of the patient interface.
Figure 38:
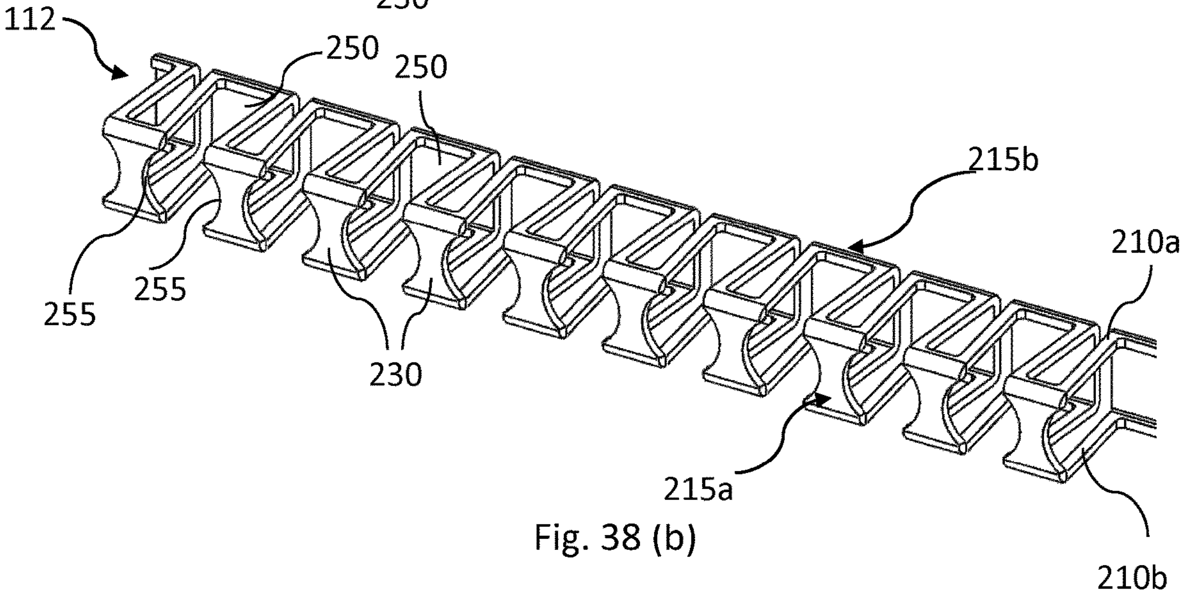

The 'C' shaped cross-section of each of the embodiments of FIG. 35 and FIG. 36 functions to maintain an open gas flow path from the first gas flow path 100 to the second gas flow path 102 defined in the diffusing material 104. It may allow the support structure 112 to cup, pinch, and/or partially encapsulate or hold onto the periphery of the diffusing material of the patient interface 10. To assist this functionality, the support structure 112 may partially pinch the diffusing material and/or be adhered to the diffusing as represented in FIG. 37.

FIGS. 38*a* and 38*b* show another embodiment of the support structure 112 that is similar to the embodiment of FIG. 32. However, in this embodiment the slots 250 are generally trapezoidally shaped when viewed in plan view and adjacent slots 250 have differing widths. The differing width slots repeat along the length of the support structure 112. The connecting members 230 each have an hourglass shape that effectively forms a notch or cutaway 255 between two adjacent connecting members 230 so as to maintain an open gas path through the side 215*a* of the support structure 112 when the support structure is fully bent towards the side 215*a*, as in the embodiment of FIG. 33. Alternatively, the connecting members may include a notch 255 as in the embodiment of FIG. 33.

Figure 39A:
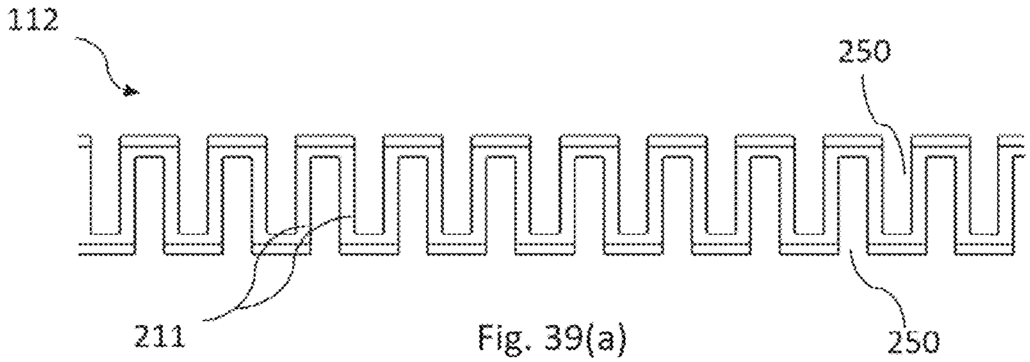
FIGS. 39*a* and 39*b* are a plan view and a perspective view respectively of a further embodiment of a support structure of the patient interface.
Figure 39:
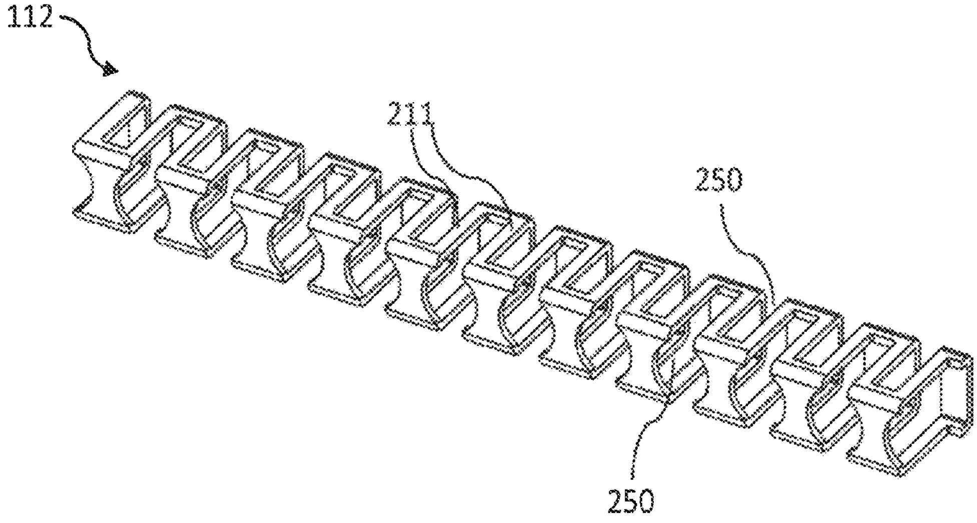
Figure 40A:
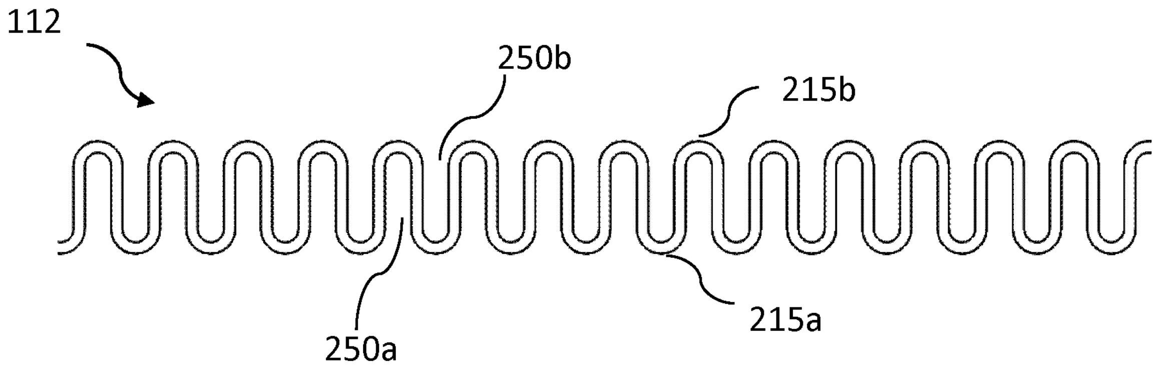
FIGS. 40*a* and 40*b* are a plan view and a perspective view respectively of a further embodiment of a support structure of the patient interface.
Figure 40B:
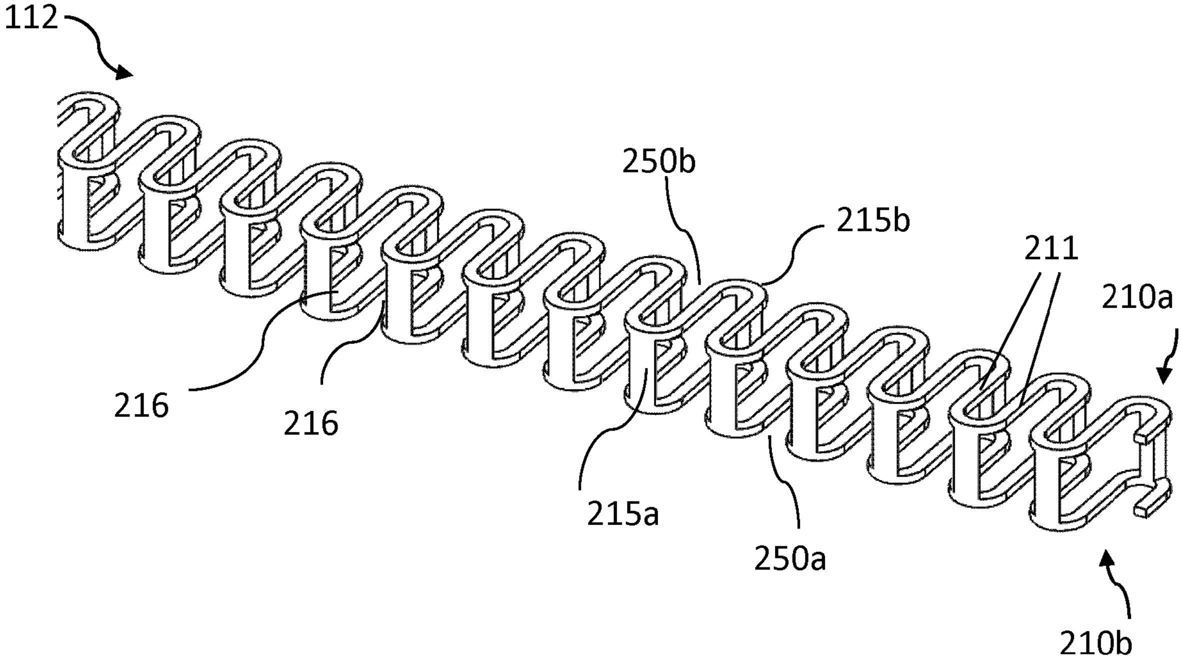

FIGS. 39*a* and 39*b* shown another embodiment of a support structure 112 that is very similar to the embodiment of FIG. 32 but having rounded cutaways 255 in the opposing second sides. Adjacent slots 250 are arranged substantially perpendicularly to the longitudinal axis of the support structure 112 in this embodiment. FIGS. 40*a* and 40*b* are another variation of the embodiment of FIG. 32. In this embodiment, the structural portions 211 are shaped such that the slots 250 each have a rounded distal end. The second sides 215*a*, 215*b* have a corresponding rounded curvature adjacent the slot 250 distal end. The rounded curvature reduces stress concentrations and minimises the use of sharp edges in the support structure that may harm the patient or user of the patient interface 10.

This embodiment utilises a repeating round wave pattern to achieve the desired rigidity of structure whilst providing a flexible structure. Each of the pair of opposing first sides 210*a*, 210*b* comprises structural portions 211 defining a repeating alternating rounded wave pattern. Each repeat of the rounded wave pattern includes a first slot 250*a* extending from one of the pair of opposing second sides 215*a* towards the other of the pair of opposing second sides 215*b*. An adjacent second slot 250*b* extends from the other of the pair of opposing second sides 215*b* towards the one of the pair of opposing second sides 215*a*.

The degree of flexibility and crush resistance can be tailored at least in part by varying the width and/or pitch and/or radius of curvature of the structural portions 211 of the sides 210*a*, 210*b* that define the slots 250*a*, 250*b* and effectively modifying the pitch of the repeating rounded wave pattern. For example, a smaller pitch between repeating structural portions 211 will result in an increased number of vertical structural portions at the opposing second sides 215*a*, 215*b*, providing increased vertical strength. As with the other embodiments of the support structure 112, a balance of vertical flexibility and resistance to vertical forces may be desired to allow the patient interface 10 to be conformed to the contours of the body before, during and after a surgical procedure, yet resist crushing forces due to the retractor and/or other surgical instruments.

In some embodiments, the pitch between the structural portions 211, i.e. a distance between structural portions 211 may be uniform along the length of the support structure 112, however in other embodiments the pitch between structural portions 211 may vary along the length of the support structure 112.

Each of the slots 250*a*, 250*b* comprises a wall at the respective opposing second side 215*a*, 215*b*, forming a vertical structural portion between the opposing first sides. In the embodiment of FIGS. 40*a*, 40*b*, the structural portions are rounded, however in other embodiments they need not be. For example the structural portions may be squared. The structural portions 215*a*, 215*b* are narrow, occupying only a portion of the rounded end of the wave pattern portions of the opposing first sides 210*a*, 210*b*. The narrow structural portions 215*a*, 215*b* provide gaps 216, seen in FIG. 40*b*, either side of the structural portions 215*a*, 215*b* that function in the same way as the notches or cutaways 255 of the embodiment of e.g. FIG. 33, allowing gas flow in the gas flow path 100 to pass through the support structure 112 under bending load. The narrow structural portions 215*a*, 215*b* of the embodiment of FIGS. 40*a* and 40*b* furthermore provide sufficient structural strength against vertical compressive forces that may act on the patient interface 10.

The support structures 112 are elongate flexible structures having a longitudinal axis, and are configured to be elastically deformable under application of a laterally and/or vertically and/or longitudinally applied force, such as may be applied during retraction of the patient interface 10 from a first, rest position to a retracted position. For example, the support structure is configured to be bendable in a lateral direction relative to the longitudinal axis. It may therefore accommodate retraction of the patient interface 10, so as to maintain the first gas flow path 100 substantially unaffected by the changing configuration of the patient interface 10 as it is retracted.

Under a bending load, some of the structural portions of the opposing second sides 215*a*, 215*b* move closer together at one of the opposing second sides 215*a*, 215*b* and some of the structural portions of the other of the opposing second sides 215*a*, 215*b* will move further away from each other, allowing the structural support 112 and the first gas flow path 100 to accommodate the retraction. Gas flow in the gas flow path 100 may still pass through the gaps between the structural portions 215*a*, 215*b* even when they are moved closer together during bending, so as to then pass through the diffusing material portion 104. In some instances of retraction of the patient interface 10, the support structure may be subject to longitudinal extension and compression. The square or rounded wave shape of the embodiments of FIGS. 31-33, 35 and 38-43 in particular (some of which are discussed below) is able to accommodate this extension and compression whilst substantially maintaining the structural integrity of the first gas flow path 100.

The support structure is configured to be bendable to conform to contours of a body of a patient surrounding the wound. The support structure an also allow the patient interface 10 to accommodate bunching up of skin or flesh at the edges of a wound as it is retracted. The support structure 112 has a cross-sectional shape configured to substantially resist compressive force applied in a vertical direction i.e. substantially perpendicularly to the plane of the opposing first sides, which also assists in maintaining the first gas flow path 100 as the patient interface is retracted and whilst it is in the retracted position. The support structure 112 permits torsional movement that may be applied to it during retraction of the patient interface. The support structures 112 may be made of a non-metallic material that provides the required mechanical and structural properties whilst also providing compatibility of the patient interface 10 with imaging devices that may be used during surgical procedures. For example, the support structure may be made of high density polyethylene (HDPE).

Figure 42A:
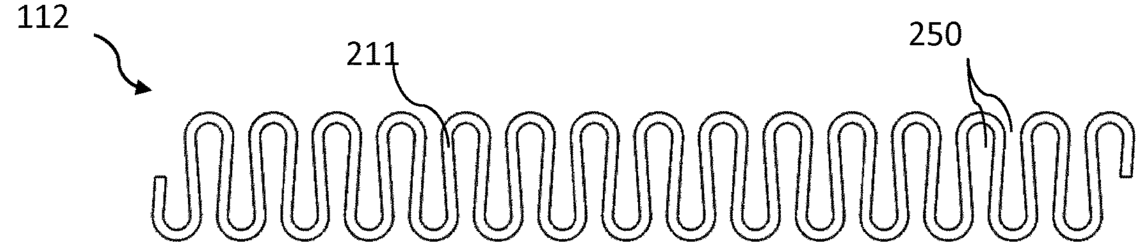
FIGS. 42*a* and 42*b* are a plan view and a perspective view respectively of a further embodiment of a support structure of the patient interface.
Figure 42B:
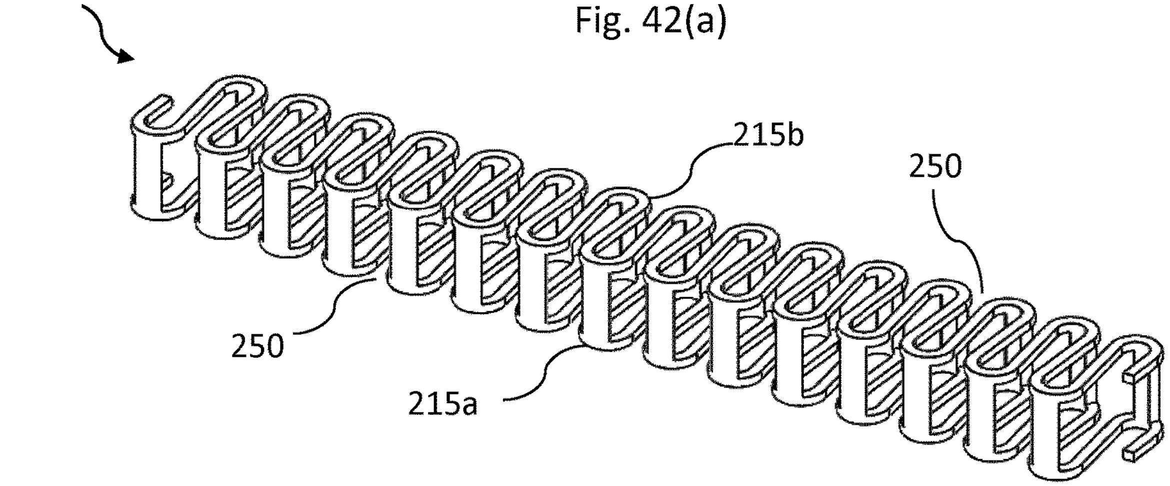
Figure 43:
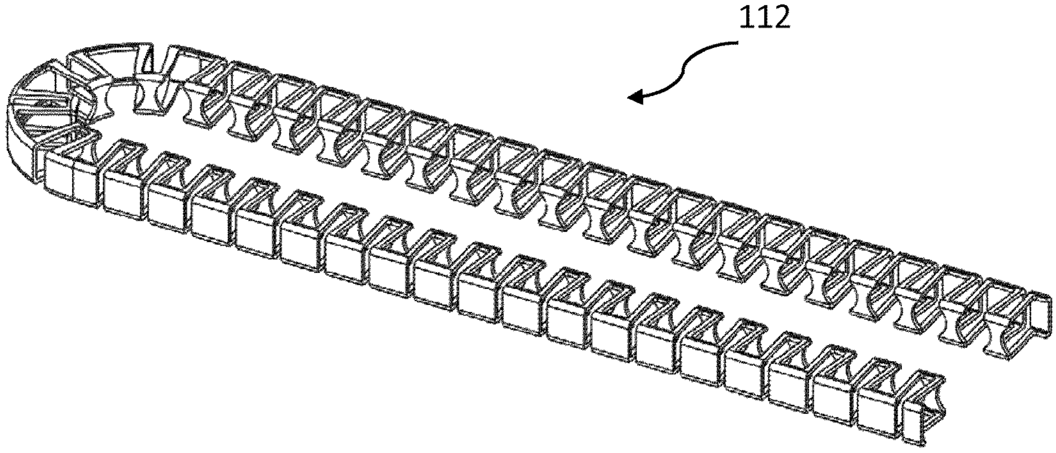
FIG. 43 is a perspective view of the support structure of the embodiment of FIGS. 38*a* and 38*b* in a bent configuration.

FIGS. 42*a* and 42*b* show an embodiment of the support structure 112 that is very similar to the embodiment of FIGS. 40*a* and 40*b*, however in this embodiment the structural portions 211 are shaped such that the slots 250 taper in width from one second side 215*a* or 215*b* towards the other of the second sides 215*a*, 215*b* to reduce the width at the slot opening.

Figure 41A:
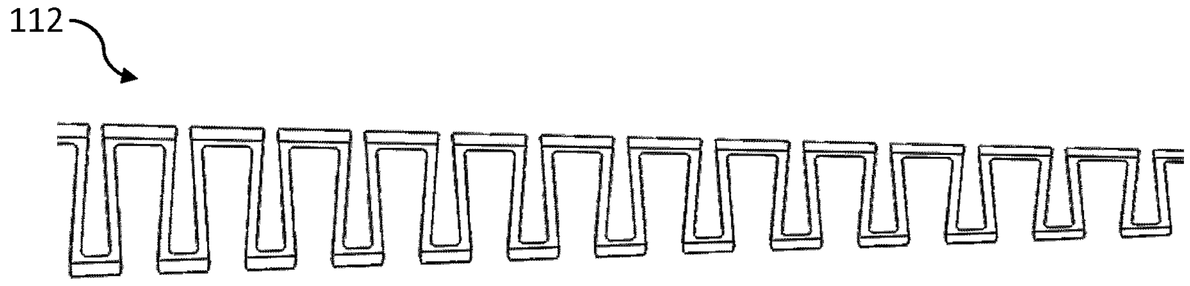
FIGS. 41*a* and 41*b* are a plan view and a perspective view respectively of a further embodiment of a support structure of the patient interface.
Figure 41B:
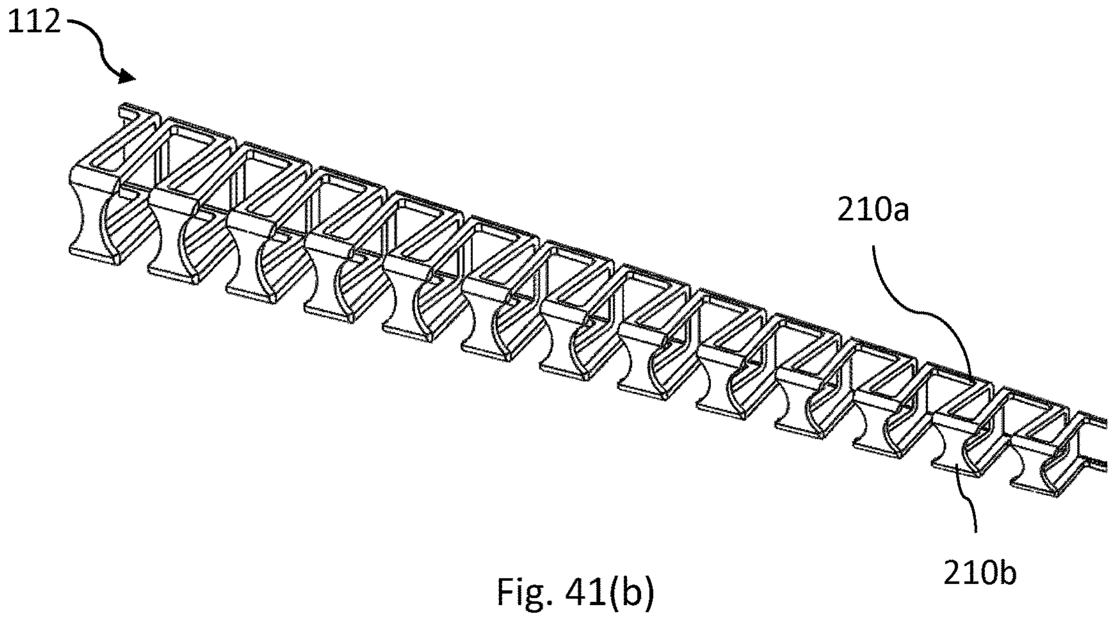

The embodiment shown in FIGS. 41*a* and 41*b* is very similar to the embodiment of FIGS. 38*a* and 38*b*. However, in this embodiment, the support structure 112 tapers when viewed in plan view along the longitudinal axis of the support structure 112. The support structure 112 also progressively tapers in height along the length thereof such that an upper surface or side 210*a* is not parallel with a lower surface 210*b* of the support structure. This embodiment may be useful in embodiments of the patient interface 10 that are similarly tapered in length and/or height as is desired to produce desired gas flow characteristics through the first gas flow path 100.

Figure 47:
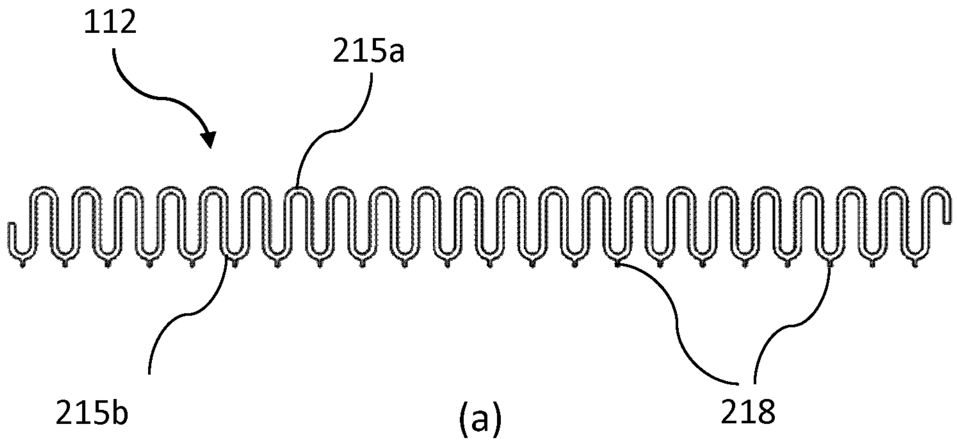
FIGS. 47*a* and 47*b* are a plan view and a perspective view of a support structure of the patient interface having grip portions.
Figure 47:
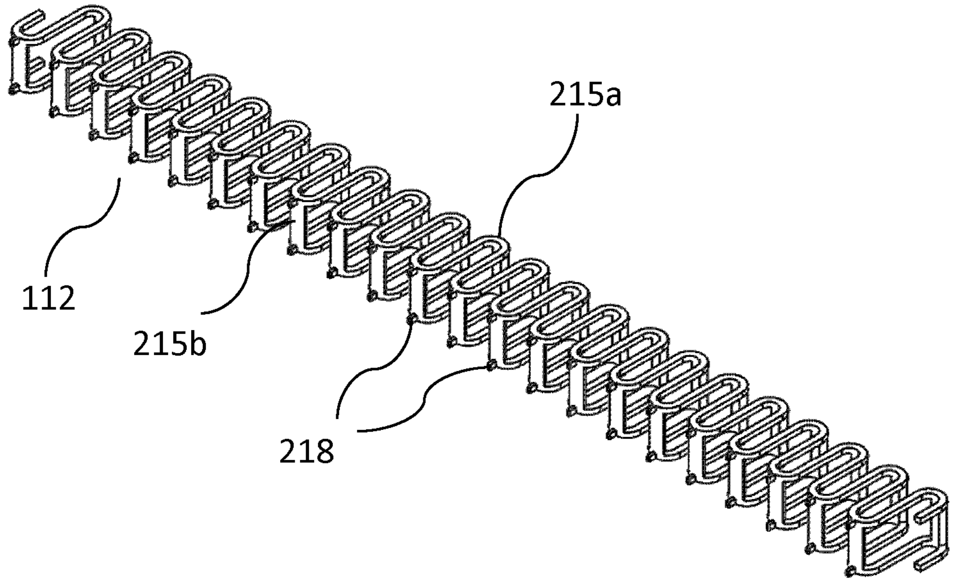

Each of the embodiments of the support structure 112 described herein may include one or more grip portions on surfaces thereof that come into contact with or is adjacent to the diffusing material 104. For example, as seen in FIG. 47, grip portions 218 extend laterally from the second side 215*b* of the support structure 112. In this embodiment, each element of the second side 215*b* has upper and lower grip portions 218 extending laterally from it. In other embodiments, each element may include only a single grip portion 218, or only some of the elements of the second side may include grip portions 218. The grip portions 218 may assist the support structure 112 to engage with the foam or other diffusing material portion 104 of the interface body 20 and retain the support structure 112 in position in the first gas flow path 100.

The support structure 112 may be provided in the first gas flow path 100 as a continuous single structure. Alternatively, it may include at least two or more separate repeating lengths. The separate lengths may be positioned end to end to create the support structure 112 and/or may be assembled together. For example, an embodiment of the support structure has three separate lengths, positioned end to end through substantially the entirety of the first gas flow path 100.

FIGS. 13*a*-13*f* illustrate various configurations of the first gas flow path 100 and the second gas flow path 102. The peripheral first gas flow path 100 may have a constant cross-sectional area as seen in FIGS. 10 to 12 or it may have a variable cross-sectional area. The variable cross-sectional area may be created by an eccentricity, a different outer boundary shape, different shape of diffusing material portion 104, or any combination thereof. A first gas flow path 100 having a variable cross-sectional area may assist with creating an evenly distributed flow from the inner surface 37 over the wound.

Figure 13A:
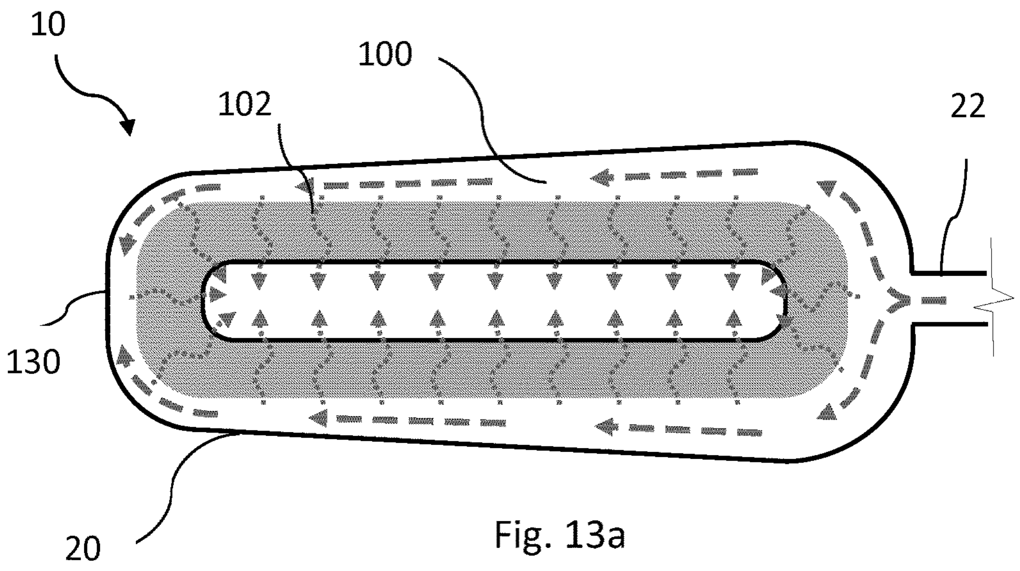
FIG. 13*a*-13*f* are schematic cross-sectional views of a embodiments of a patient interface having various configurations of first gas flow path and diffusing material portion.

FIGS. 13*a*-13*d* show embodiments of a patient interface 10 in which the interface body 20 has an elongate asymmetric shape. In the embodiment of FIG. 13*a*, the interface body 20 is wider closer to the gas inlet 22 than it is towards a distal end or portion 130 of the interface body 20 opposite the gas inlet 22. A cross-sectional area of the first gas flow path 100 is larger closer to the gas inlet 22 and decreases toward the distal portion 130 of the interface body opposite the gas inlet 22. This configuration is intended to supply sufficient gas flow to ensure continuous supply through the porous diffusing material portion 104 both close to the gas inlet 22 and distally from the gas inlet 22.

Figure 13B:
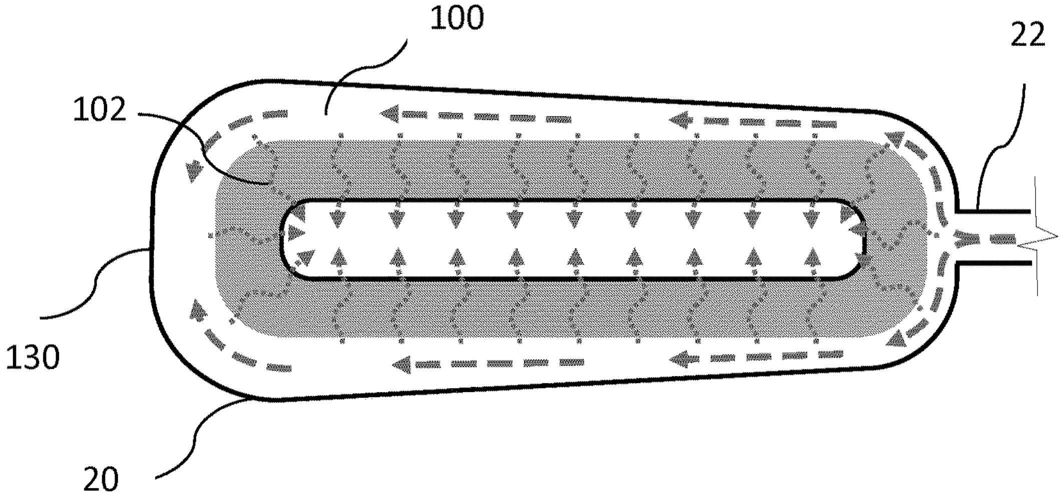

According to Bernoulli's equation, for a given flow rate, a lower pressure exists where flow velocity is faster through a narrow flow channel. However, fluid flow is perturbed by viscosity and friction such that pressure is always relatively higher at the source of the flow compared to downstream. To create an even flow around the outer periphery of the diffusing material portion 104 it is advantageous for these two effects to compensate each other where possible. This may be achieved by having a narrow first gas flow path 100 proximal to the gas inlet 22 and widening distally from the gas inlet 22. In the embodiment of FIG. 13*b*, the cross-sectional area of the first gas flow path 100 is narrower closer to the gas inlet 22 and increases toward a distal portion 130 of the interface body 20. The result is a more even pressure distribution around the external periphery of the diffusing material portion 104 and therefore a spatially more even flow rate through the diffusing material portion 104.

Figure 13C:
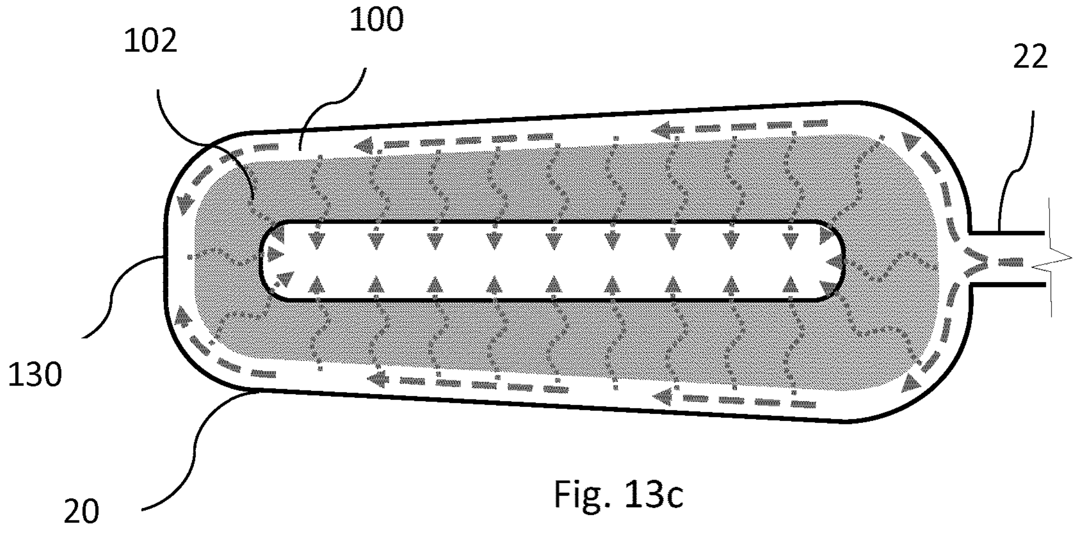

Alternative configurations for the relative cross-sectional areas of the first gas flow path 100 and the second gas flow path 102 are shown in FIGS. 13*c*-13*f*. In FIG. 13*c*, the first gas flow path 100 has a constant cross-sectional area from the gas inlet 22 towards the distal portion 130 of the interface body 20. However the diffusing material portion 104 through which the second gas flow path 102 is formed is thicker towards the inlet 22 than it is towards the distal portion 130 of the interface body 20. The gases entering the second gas flow path 102 closer to the gas inlet 22 therefore meet with a higher resistance through the second gas flow path 102 than do gases entering the second gas flow path 102 towards the distal portion 130 of the interface body 20, at least partially offsetting the increased resistance met by the gases during the time taken for the gases to travel through the first gas flow path 100 to reach the distal portion 130 of the interface body 20.

Figure 13D:
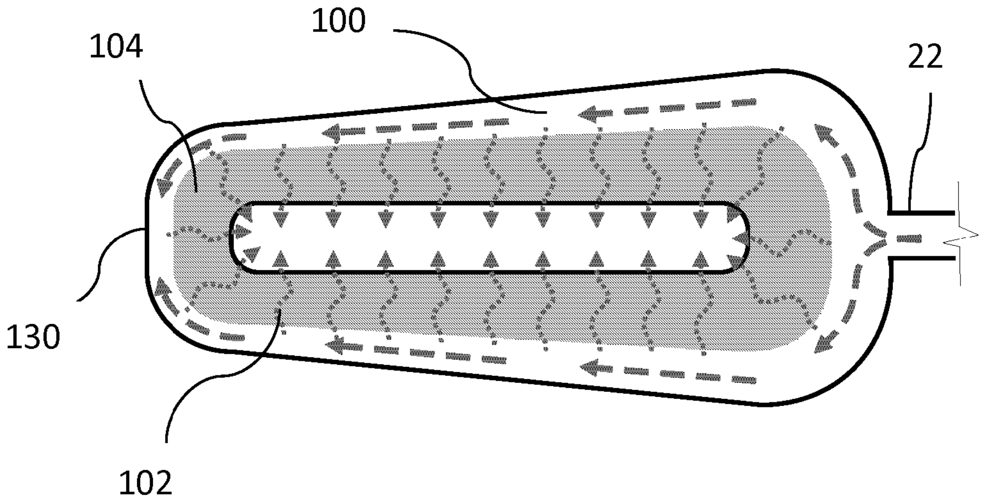

FIG. 13*d* shows an embodiment in which the cross-sectional area of the first gas flow path 100 is wider closer to the gas inlet 22 and decreases towards a distal portion 130 of the interface body 20 as in FIG. 13*a*. In addition, the diffusing material portion 104 through which the second gas flow path 102 is formed is thicker towards the gas inlet 22 than it is at the distal portion 130 of the interface body 20, as in FIG. 13*c*. The diffusing material portion 104 therefore imposes a higher resistance to gas flow closer to the inlet 22, which can offset the preferential imbalance of gas flow exiting the first gas flow path 100 closer to the gas inlet 22.

Figure 13E:
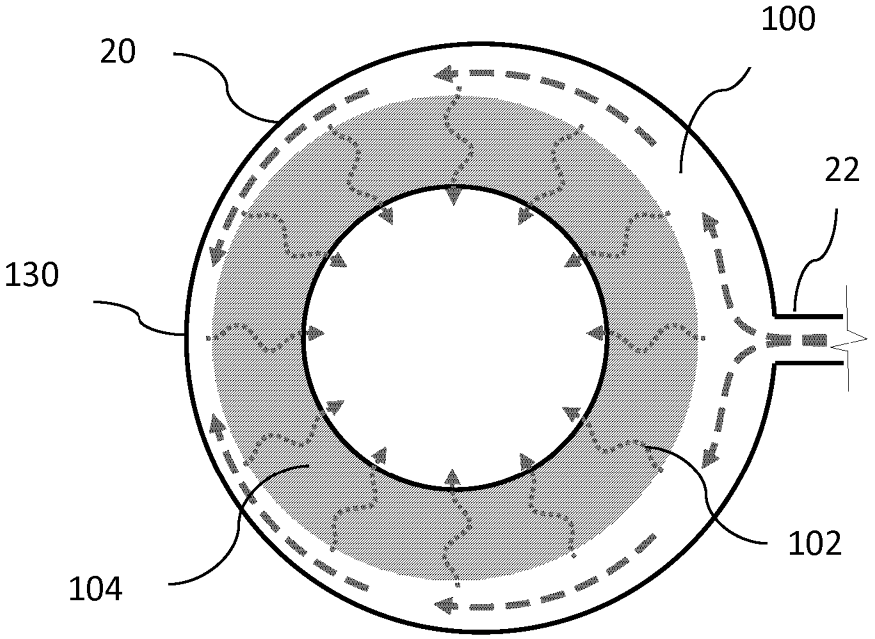
Figure 13F:
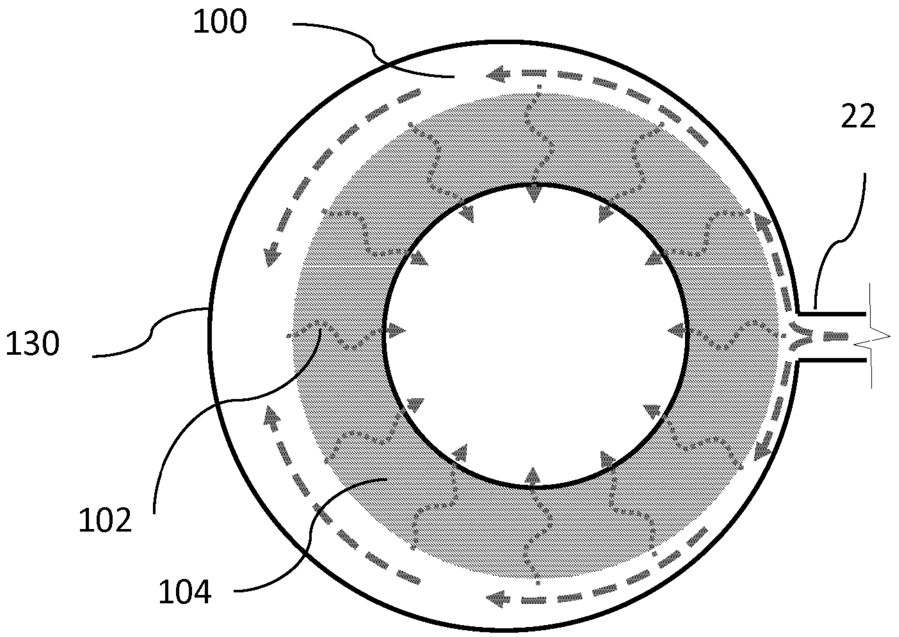

FIGS. 13*e* and 13*f* are examples of embodiments of circular shaped interface bodies 20 in which the configuration of the first gas flow path 100 can be achieved by positioning the diffusing material portion 104 eccentrically from the centre of the circular shaped interface body 20. In FIG. 13*e*, the diffusing material portion 104 is located eccentrically away from the gas inlet 22, creating a first gas flow path 100 having a larger cross-sectional area closer to the gas inlet 22, the cross-sectional area decreasing towards the distal portion 130 of the interface body 20. The embodiment of FIG. 13*f* has the opposite configuration to FIG. 13*e*, whilst aiming to achieve the same effect. The diffusing material portion 104 is located closer to the gas inlet 22, creating a narrow first gas flow path 100 towards the gas inlet 22, widening to a larger cross-sectional area towards the distal portion 130 of the interface body 20. The thickness of the diffusing material portion 104 is constant in each of FIG. 13*e* and FIG. 13*f*. Whilst the embodiments of FIGS. 13*e* and 13*f* are illustrated and described as being circular in shape, they need not be circular and other shapes, for example ovoid or similar, may be utilised to similar effect.

Figure 14:
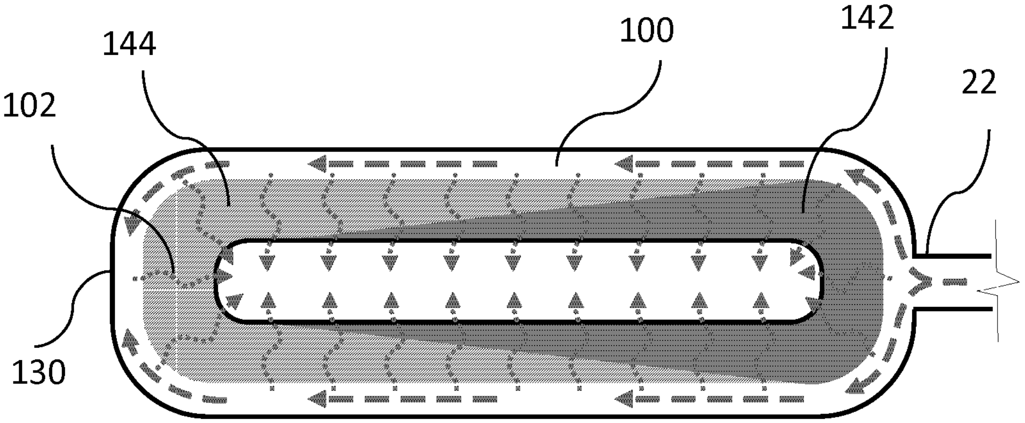
FIG. 14 is a schematic cross-sectional view of an embodiment of a patient interface having two stages of diffusing material of different densities.

In another embodiment shown in FIG. 14, rather than increase the thickness of the diffusing material portion 104 to create a higher flow resistance to flow entering the second gas flow path 102, the diffusing material portion 104 is comprised of stages of different flow resistance foam or other diffusing material. A higher resistance diffusing material portion 142 is positioned closer to the gas inlet 22 and the gas source 14. The higher resistance diffusing material portion 142 decreases in cross-sectional area towards the distal portion 130 of the interface body 20. A lower resistance diffusing material portion 144 correspondingly increases in cross section towards the distal portion 130 of the interface body 20. The total cross-sectional area of the diffusing material portions 142, 144 is constant along the length of the interface body 20. Any number of stages of different resistance diffusing materials can be used to form the graduation in the resistance of the diffusing material portions. Alternatively, a foam or other diffusing material having a continuous gradient of flow resistance that reduces away from the gas inlet 22 can be used to achieve the same effect.

Figure 15:
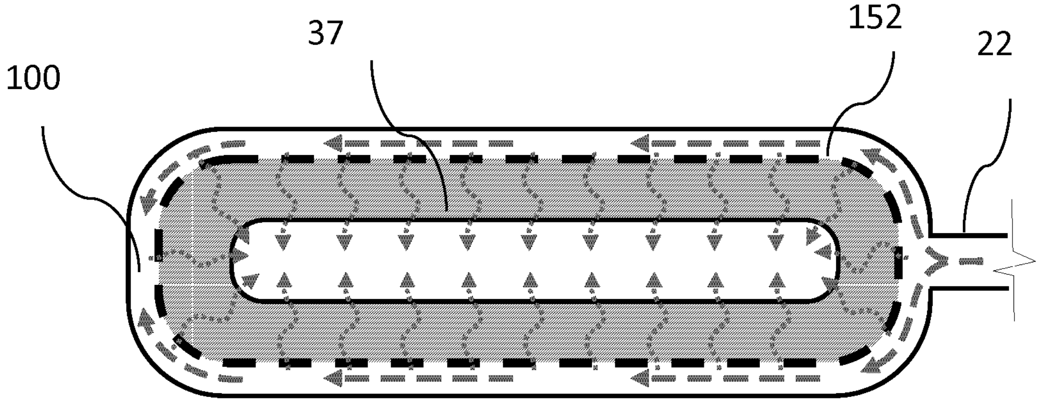
FIG. 15 is a schematic cross-sectional view of an embodiment of a patient interface having one or more flow regulators.

One or more flow restrictions 152 may be arranged between the first gas flow path 100 and the second gas flow path 102, as schematically shown in FIG. 15. The flow restrictions 152 facilitate a more even distribution of flow delivery to the outlet at the inner surface 37 of the diffusing material portion 104. Such flow restrictions 152 include one or more of a baffle, a series of orifices, slits, slots or any variety or combination of such flow restrictions 152 positioned between the peripheral first gas flow path 100 and the diffusing material portion 104.

In some embodiments, the flow restrictions may be more restrictive closer to the gas inlet 22 and less restrictive distally from the gas inlet 22. For example, in one embodiment the flow restrictions 152 may include orifices. The orifices may be larger in diameter and/or more closely spaced towards the distal portion 130 of the interface body 20 and smaller in diameter and/or more widely spaced towards the gas inlet 22.

In another embodiment, the flow restrictions 152 may include a slot extending partially, or in segments, or continuously around the diffusing material portion 104. At the inlet 22, the slot may reduce to a solid wall such that a jet of gas emanating from a curved neck of the gas inlet 22 is completely deflected radially around the first gas flow path 100. Alternatively, the slot may remain partially open such that a small portion of the jet and delivered gas can pass. In another embodiment, the flow restriction 152 includes a baffle. The baffle may be wider distally from the gas inlet 22 so as to impose a larger impediment to the gas flow entering the second gas flow path 102 closer to the gas inlet 22.

Figure 16:
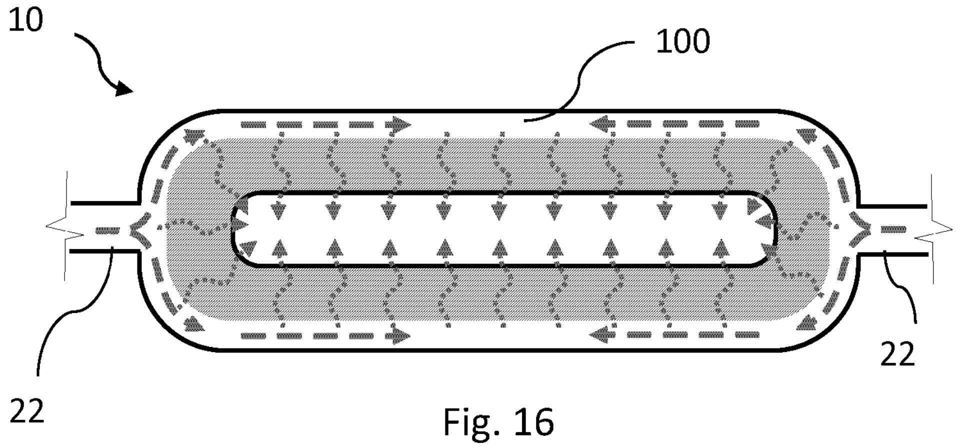
FIG. 16 is a schematic cross-sectional view of an embodiment of a patient interface having more than one inlet.
Figure 17:
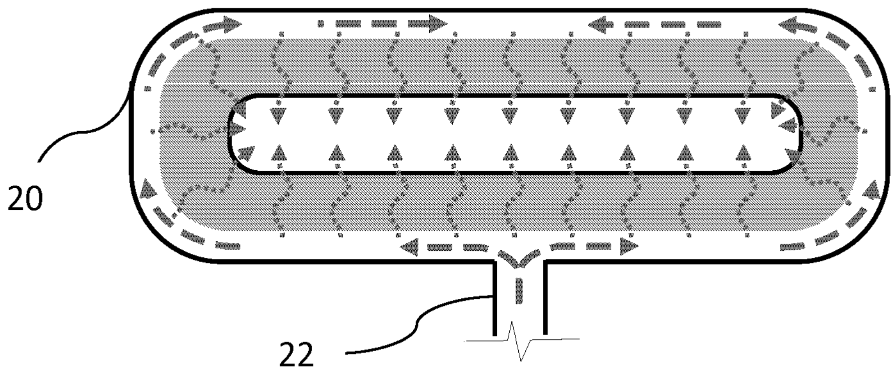
FIG. 17 is a schematic cross-sectional view of an embodiment of a patient interface having an alternative inlet position.

In the embodiment of FIG. 16, the patient interface 10 has two gas inlets 22, with the second gas inlet 22 positioned opposite the first gas inlet 22 at the distal portion 130 of the interface body. Any number of gas inlets 22 of the same or different sizes can be used to provide flow to the first gas flow path 100 to distribute the flow more evenly along the first gas flow path 100. In FIG. 17, a single gas inlet 22 is provided as in previous embodiments, however the gas inlet 22 is positioned mid-way along an outer peripheral wall of the interface body 20. The gas inlet 22 or plurality of gas inlets 22 may be positioned anywhere around the patient interface.

FIGS. 18*a* to 18*e* show embodiments of the patient interface 10 that include a flow splitter 182 or a flow director 184 that encourage the gas flow entering the patient interface 10 to travel around the peripheral first gas flow path. The flow splitter 182 and the flow director 184 reduce flow turbulence and separated flow caused by an abrupt change in direction in the geometry of the flow path. In the embodiments of FIGS. 18*a* to 18*e*, the patient interface has an elongate interface body 20 of constant width. The first gas flow path 100 peripherally surrounds the diffusing material portion 104. The second gas flow path 102 exits the diffusing material portion 104 at the outlet defined by the inner surface 37.

Figure 18A:
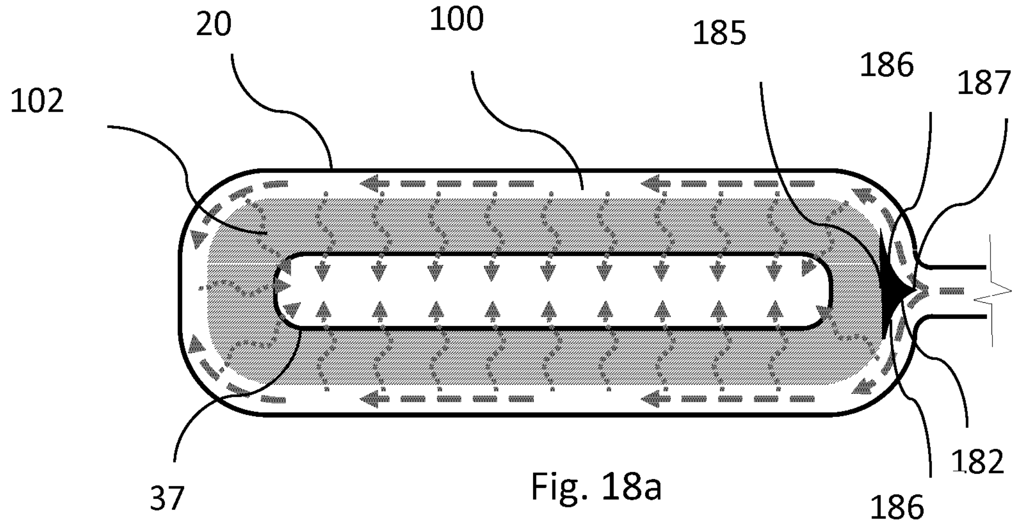
FIGS. 18*a*-18*b* are schematic cross-sectional views of embodiments of a patient interface including a flow splitter.

In FIG. 18*a*, a flow splitter 182 is installed at a juncture of the gas inlet 22 and the first gas flow path 100. The flow splitter 182 is a generally triangular shaped device in plan view, having a flat surface 185 facing the diffusing material portion 104 and lying flat against it, and two concave curved surfaces 186 facing the gas inlet 22, meeting at an apex 187 directly adjacent the gas inlet 22. Gas flow entering the patient interface 10 at the gas inlet 22 is split into two flow streams at the apex 187, with approximately 50% of the gas flow being directed to the left of the apex 187 and the other approximately 50% being directed to the right of the apex 187. The concave curved surfaces 186 guide the gas flow around the sharp corners at the juncture of the gas inlet 22 and the first gas flow path 100 and into the first gas flow path 100.

Figure 18B:
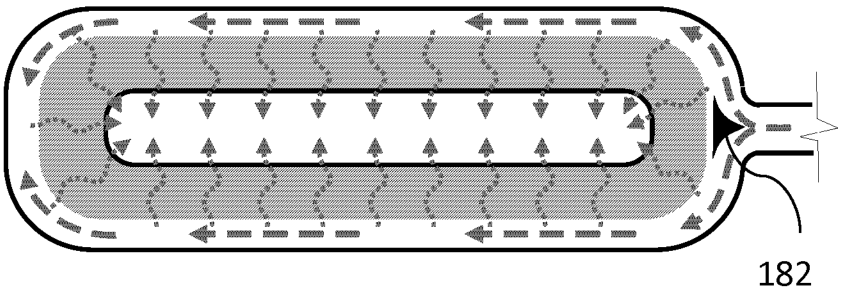

In FIG. 18*b*, a smaller version of the flow splitter 182 is installed at a juncture of the gas inlet 22 and the first gas flow path 100. In this embodiment, the flow splitter 182 is positioned in the first gas flow path 100 such that a gap is present between its flat surface 185 and the diffusing material portion 104. An offset gap has the effect of allowing a proportion of gas flow to pass through the diffusing material directly behind the flow splitter 182. In some embodiments, the splitter 182 may split the gas flow into two flow streams having a flow ratio other than 50:50. For example, the splitter 182 may be configured to split the gas flow into two streams having a flow ratio of 70:30 or 30:70 or 60:40 or 40:60 or other desired flow ratio. In an embodiment, the flow splitter 182 may be adjustable or moveable within the interface body 20 to achieve a desired flow ratio.

Figure 18C:
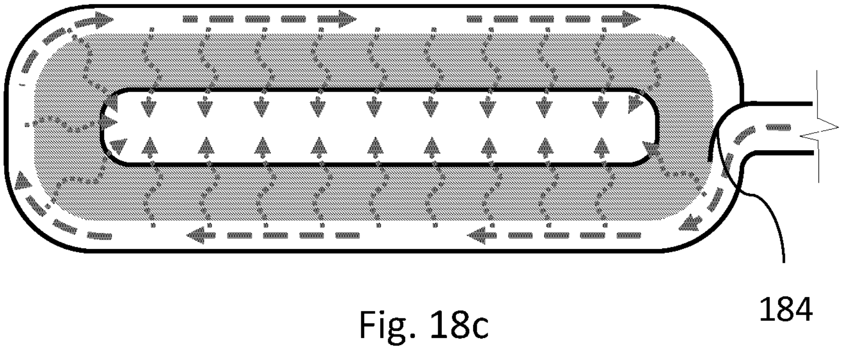
FIGS. 18*c*-18*d* are schematic cross-sectional views of embodiments of a patient interface including a flow director.
Figure 18D:
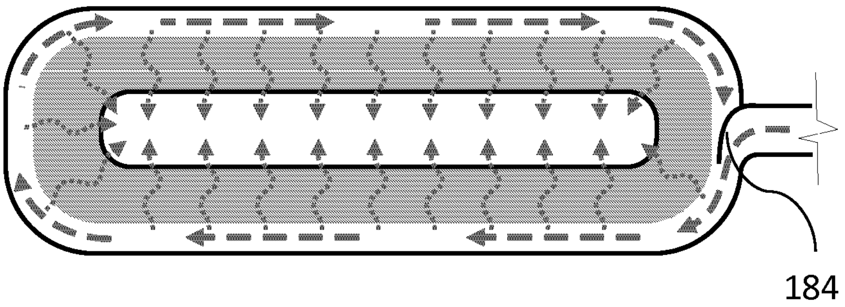

In FIG. 18*c*, a flow director 184 comprises a curved wall installed at the juncture of the inlet 22 and the first gas flow path 100 and oriented to guide the entire gas entering the gas inlet 22 in a clockwise direction around the first gas flow path 100. In this embodiment the flow director bridges the first gas flow path 100 such that all gas entering the patient interface 10 is directed to follow this path. In the embodiment of FIG. 18*d*, the flow director 184 is offset from the diffusing material portion 104 to allow gas flow to pass behind the flow director 184 to the diffusing material portion 104 behind it.

Figure 18E:
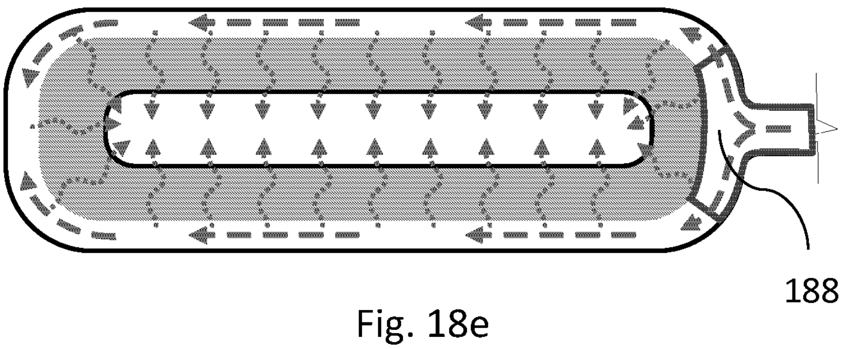
FIG. 18*e* is a schematic cross-sectional view of an embodiment of a patient interface having a flow splitter.
Figure 19:
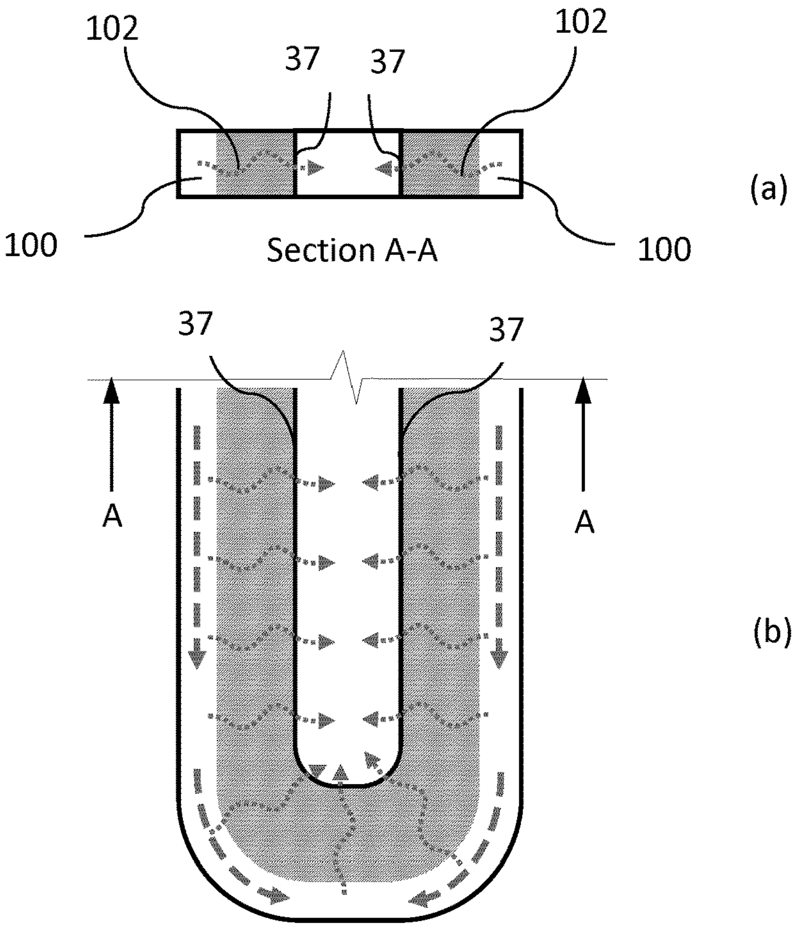
FIG. 19*a* is a schematic view of a vertical cross-section A-A of the patient interface of FIG. 19*b;*
FIG. 19*b* is a partial schematic cross-sectional view of an embodiment of a patient interface.
Figure 20:
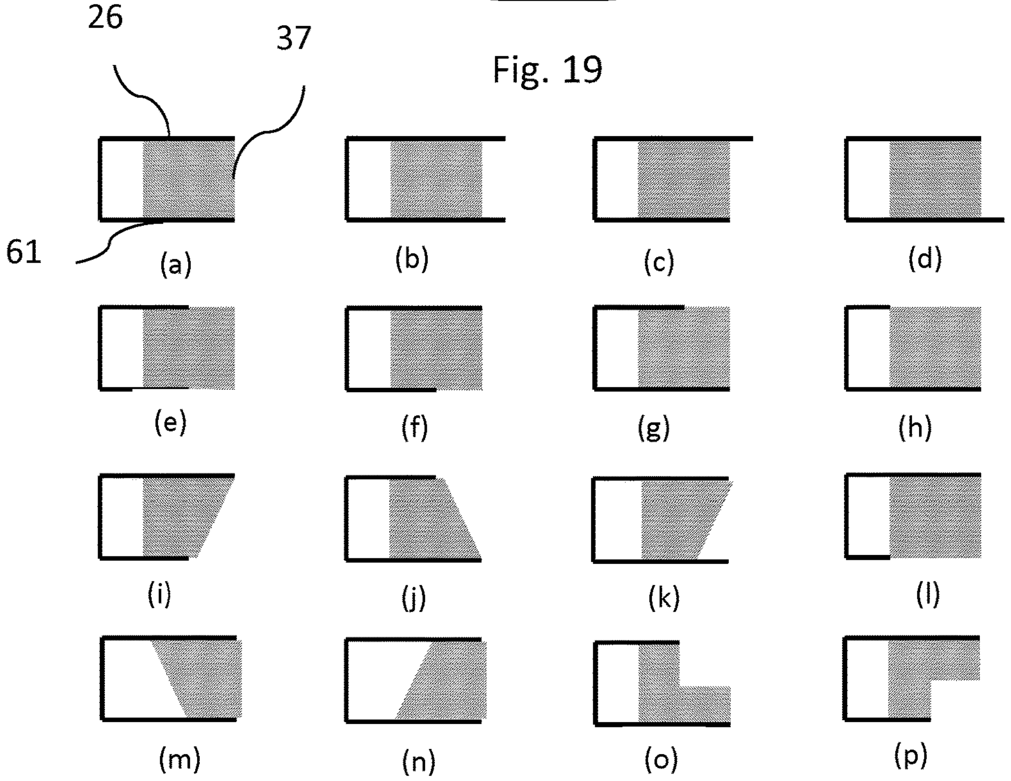
FIGS. 20*a*-20*p* are schematic partial cross-sectional views at Section A-A of the patient interface of FIG. 19*a* showing different outlet configurations.

The flow splitter 182 and the flow director 184 can be constructed into the shape of the diffusing material portion 104 or it can be formed integrally with the outer membrane 126 or skin where this is a separate component. Alternatively, the flow splitter can also be a separate component itself that is overmoulded by the outer membrane 126 or skin of the interface body 20. The embodiment of FIG. 18*e* shows a further example of a flow splitter 188 that comprises a separate component that is integrated into the patient interface 10, for example by overmoulding. The flow splitter 188 comprises of a tubular T-piece that is installed at the junction of the gas inlet 22 and the first gas flow path 100. All gas flow entering the gas inlet 22 passes through the flow splitter 188 and is split into two streams passing into the first gas flow path 100.

Figure 48:
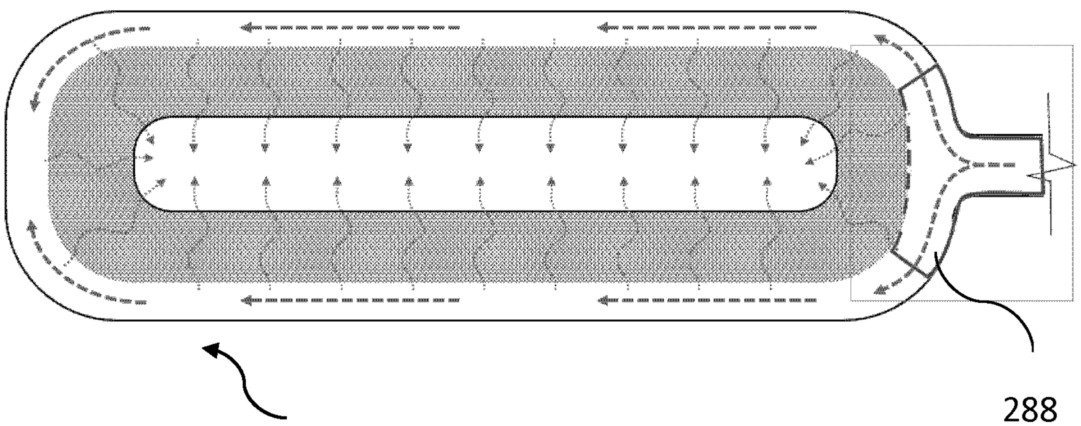
FIGS. 48*a* and 48*b* are a cross-sectional schematic view of a patient interface having a flow splitter and a perspective view of the flow splitter.
Figure 48:
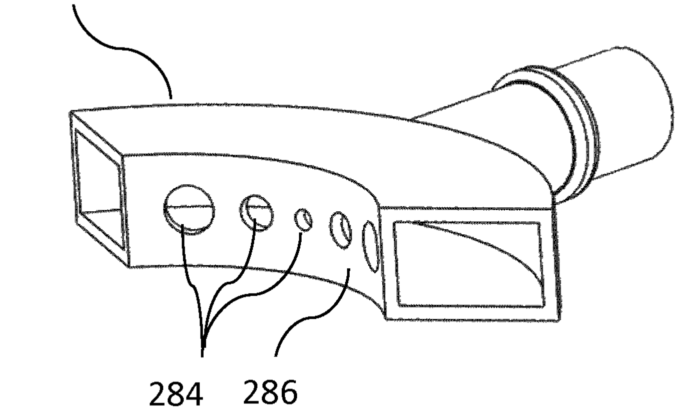

A variation of the flow splitter 188 is shown in FIG. 48. The flow splitter 288 has the same features as the flow splitter 188 and comprises of a tubular T-piece that is installed at the junction of the gas inlet 22 and the first gas flow path 100. All gas flow entering the gas inlet 22 passes through the flow splitter 188 and is split into two streams passing into the first gas flow path 100 around the diffusing material portion 104. The flow splitter 288 also includes at least one aperture 284 in a downstream surface 286 of the flow splitter 288 that lies adjacent to an upstream surface of the diffusing material portion 104.

The embodiment of FIG. 48 shows five apertures 284 arranged in a horizontal line across the downstream surface 286. The apertures 286 may be of the same size or different sizes, and need not be arranged in a line. Where a plurality of the apertures 284 are of different size, one or more smaller apertures are located in a mid-section of the flow splitter surface. Larger apertures may be located at or towards opposing ends of the flow splitter surface, adjacent the respective openings of the flow splitter 288 into the first gas flow path 100. Medium sized apertures may be between the smaller and larger apertures. The at least one aperture 284 allows a portion of the gas passing through the flow splitter

188 to pass through the aperture 284 and into the diffusing material portion 104. The at least one aperture 284 may prevent or at least mitigate pooling of gas in or behind (i.e. on the second gas flow path side) the flow splitter 288 as it attempts to flow around the corner of the T-piece. It may also increase gas flow coverage around the surgical site or wound site in the vicinity of the gas inlet 22.

In embodiments of the patient interface in which the outer membrane 126 is translucent or transparent, the flow director 184 or flow splitter 182, 188, 288 may be visible through the outer membrane 126. The flow director 184 or flow splitter 182, 188, 288 may comprise or contain a thermochromic material or other material that changes colour in response to variation in temperature and/or humidity.

The gas flow exiting the patient interface 10 at the outlet of the diffusing material portion 104 of the interface body 20 can be influenced by different outlet configurations to achieve a desired flow pattern and performance. For example, the outer membrane 126, skin or film at the outlet, i.e. at the inner surface 37 of the diffusing material portion 104 of the interface body 20 may terminate flush with the diffusing material inner surface 37 or it may overhang the inner surface 37 or it may terminate prior to the inner surface 37, leaving an exposed portion of the diffusing material at the top surface 26 and/or bottom surface 61 of the interface body 20. An overhanging top surface 26 as shown in FIGS. 20*b* and 20*c* has the effect of preventing the conditioned gas from flowing upwards and away from the wound site, keeping the microenvironment close to the wound and improving the performance of the patient interface 10. A similar effect may be achieved with an inwardly angled inner surface 37 as shown in FIG. 20*i* and FIG. 20*k*. However, having a section of the top surface 26 exposed to the atmosphere as shown in FIG. 20*g* and FIG. 20*h* may assist to direct flow upwards to deflect airborne particles away from the wound. The outlet configuration may therefore be chosen to achieve a desired gas flow characteristic adjacent the wound site.

A schematic view of a vertical cross-section A-A of the interface body 20 of FIG. 19*b* is shown in FIG. 19*a*. In the embodiments shown, the patient interface 10 has an essentially flat and low profile i.e. it is significantly wider than it is tall when in use. The low profile provides the required functionality without being obtrusive to the surgeon in use at a surgical wound site. In an alternative embodiment, the patient interface 10 has a raised profile such that it is taller than the low profile embodiments. For example, its height may be 50% or more of its width. The raised profile of the patient interface may create a wall around the surgical wound site. Delivery of the warm/humid gas into the walled area may create an additional micro-environment above and/or at a distance from the surgical wound site, which may provide increased protection of the surgical site against loss of temperature and moisture. An embodiment of such a raised profile patient interface 10 may include more than one gas inlet 22 for multiple levels of gas delivery i.e. stacked gas delivery into the patient interface 10.

Examples of different outlet configurations are shown schematically in FIGS. 20*a* to 20*p*. In the embodiment of FIG. 20*a*, the outer membrane 126, skin or film at the outlet, i.e. at the inner surface 37 of the diffusing material portion 104 of the interface body 20 terminates flush with the diffusing material inner surface 37. However, in FIG. 20*b*, the outer membrane 126 or skin overhangs the inner surface 37 at both the top surface 26 and the bottom surface 61. In FIG. 20*c* the top surface overhangs the inner surface 37 whilst the bottom surface 61 remains flush with the inner surface 37, whilst in FIG. 20*d* the bottom surface 61 extends beyond the inner surface 37 whilst the top surface 26 remains flush with the inner surface 37. In FIG. 20*e*, both the top surface 26 and the bottom surface 61 are partially exposed to the atmosphere adjacent the inner surface 37, whilst in FIG. 20*f*, the bottom surface 61 only is partially exposed to the atmosphere adjacent the inner surface 37 whilst the top surface 26 remain flush with the inner surface 37. In FIG. 20*g* the top surface 26 only is partially exposed to the atmosphere adjacent the inner surface 37 whilst the bottom surface 61 remains flush with the inner surface 37. In FIG. 20*h*, a larger portion of the top surface 26 is exposed to the atmosphere adjacent the inner surface 37.

FIG. 20*i* shows an embodiment in which the inner surface 37 is formed at an angle to the vertical, specifically angled inwardly such that the top surface 26 extends further into the pre-shaped slot 32 than does the bottom surface 61. This inwardly angled surface has the effect of encouraging the exiting gas to remain close to the wound edge. Conversely, in FIG. 20*j* the inner surface 37 is angled outwardly such that bottom surface 61 extends beyond the top surface 26. This configuration has the effect of encouraging the gases to flow upwardly to deflect airborne particles. In FIG. 20*k*, the inner surface 37 is angled inwardly as in FIG. 20*i*, however the bottom surface 61 is extended to terminate flush with the top surface 61. In FIG. 20*l*, the inner surface 37 terminates flush with the top surface 26, whilst at least a portion of the bottom surface 61 is exposed to the atmosphere.

FIG. 20*m* shows an embodiment in which an outer surface of the diffusing material portion 104 is flat, however the inner surface 37 is angled inwardly to promote a greater proportion of flow exiting the inner surface 37 to exit towards a lower portion thereof. FIG. 20*n* also shows a flat outer surface of the diffusing material portion 104 However, in this embodiment the inner surface 37 is angled outwardly. In FIG. 20*o*, the inner surface 37 of the diffusing material portion 104 is formed with a stepped profile such that a lower portion of the inner wall 37 extends further into the slot 32 than does an upper half of the inner surface 37. This configuration also deflects airborne particles upwards. In the embodiment of FIG. 20*p*, the inner surface 37 of the diffusing material portion 104 is formed with a stepped profile such that a lower portion of the inner wall 37 is recessed relative to an upper half of the inner surface 37. This configuration encourages the gas flow to flow downwardly towards the wound edge.

The foam diffusing material may be slightly compressed within a housing (not seen the Figs.) to assist retention and location of the foam and/or manipulate the pore size of the foam. The application of varying amounts of compression along the length of the interface body 20 can vary the pore size to promote even flow delivery at the inner surface 37.

The first gas flow path 100 is part of the outer membrane 126 and as such may be made from a thin film material such that when gas passes into the gas inlet 22 of the patient interface 10, the first gas flow path 100 is self-inflated. In the embodiments of FIG. 21, the thin film is adhered to the surface of the diffusing material portion 104 by an adhesive, or through an overmoulding process, or a heat treating process that, for example, laminates a polyurethane film onto a polyurethane foam. In the embodiment of FIG. 21*a*, the thin film material is formed by adhering or overmoulding or laminating the film over the diffusing material portion to create the first gas flow path 100. Similarly if a top and bottom film are to be joined and sealed to create the first gas flow path 100 as seen in FIG. 21*b*, an adhesive or heat treating process can be used.

Figure 23:
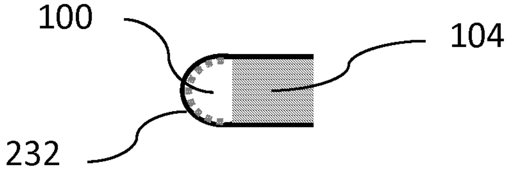
FIG. 23 is a partial cross-sectional view of an embodiment of a patient interface including a liner in the first gas flow path.

As seen schematically in FIG. 23, the first gas flow path can be lined with a lining 232 to prevent tackiness of an inner surface of the thin film material 92, to prevent the inner surfaces from sticking together and occluding the first gas flow path. The lining 232 may be a powder and/or other material that has low adherence properties. In some embodiments, the powder may include an anti-biotic.

The embodiments of the present disclosure are thus far described as having a peripheral first gas flow path 100. In practice, the first gas flow path may be on the top, underneath, and/or around the circumference of the diffusing material, as seen in the cross-sectional views of the interface body in FIGS. 22*a-e*. In FIG. 22*a*, the first gas flow path 100 is positioned above the diffusing material such that gases enter the second gas path 102 from above. In FIG. 22*b*, the first gas path 100 extends over the top and the periphery of the diffusing material, therefore the gases can enter the second gas path 102 from above the diffusing material or from its periphery. In FIG. 22*c*, the first gas flow path 100 is underneath the diffusing material. Gases in the first gas flow path 100 accordingly enter the second gas flow path 102 from underneath the diffusing material. In FIG. 22*d*, the first gas path 100 extends underneath and around the periphery of the diffusing material, therefore the gases can enter the second gas path 102 from underneath the diffusing material or from its periphery. In FIG. 22*e*, the first gas flow path 100 substantially surrounds the diffusing material except for the inner surface 37, as it extends over the top, underneath and around the periphery of the diffusing material. The gases in the first gas flow path may access the second gas flow path 102 from above, below or around the periphery of the diffusing material.

Figure 49:
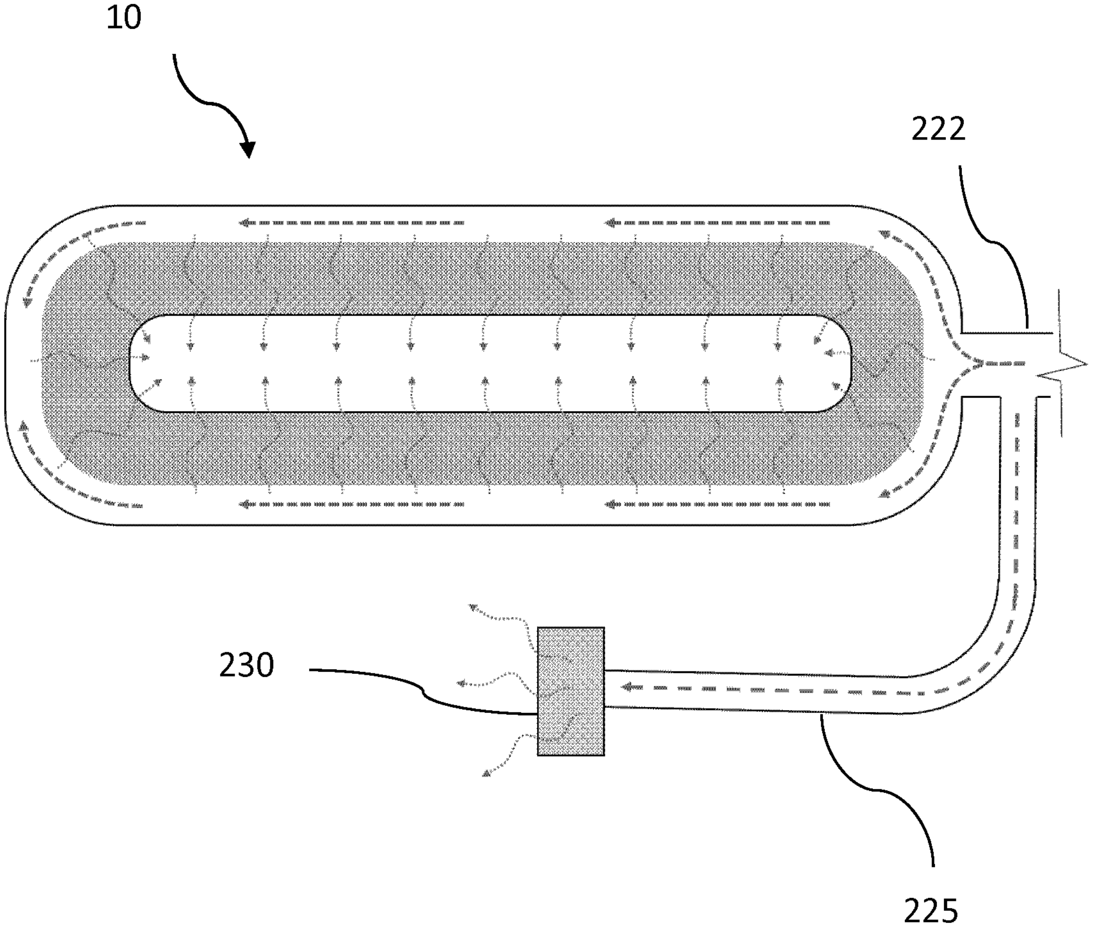
FIG. 49 is a cross-sectional schematic view of a patient interface having a further gas flow path to a secondary device.

The gas inlet through which gases enter the interface body 20 of the patient interface 10 may be configured for diverting a portion of gas flow into a further flow path. FIG. 49 shows a patient interface 10 having a gas inlet 222 that admits gas flow into the first gas flow path 100 but which also has an aperture into a tube 225 defining a further flow path upstream of the first gas flow path 100 for diverting a portion of the gas in the gas inlet 222 towards a secondary device 230. The secondary device 230 may be, for example, a second patient interface 10 or a diffuser such as a Vita-Diffuser™ manufactured by Cardia Innovation™ or other surgical wound protecting diffuser. The secondary device 230 may be integrated with or operable in communication with the primary patient interface 10 to provide a second stream of conditioned gas to the wound site. For example, the secondary device 230 maybe operably connected to the primary patient interface 10 via a Luer lock connection. The patient interface 10 may be advantageously used for large, deep and/or difficult to reach wound sites where additional humidity may be required from a secondary device 30.

Figure 50:
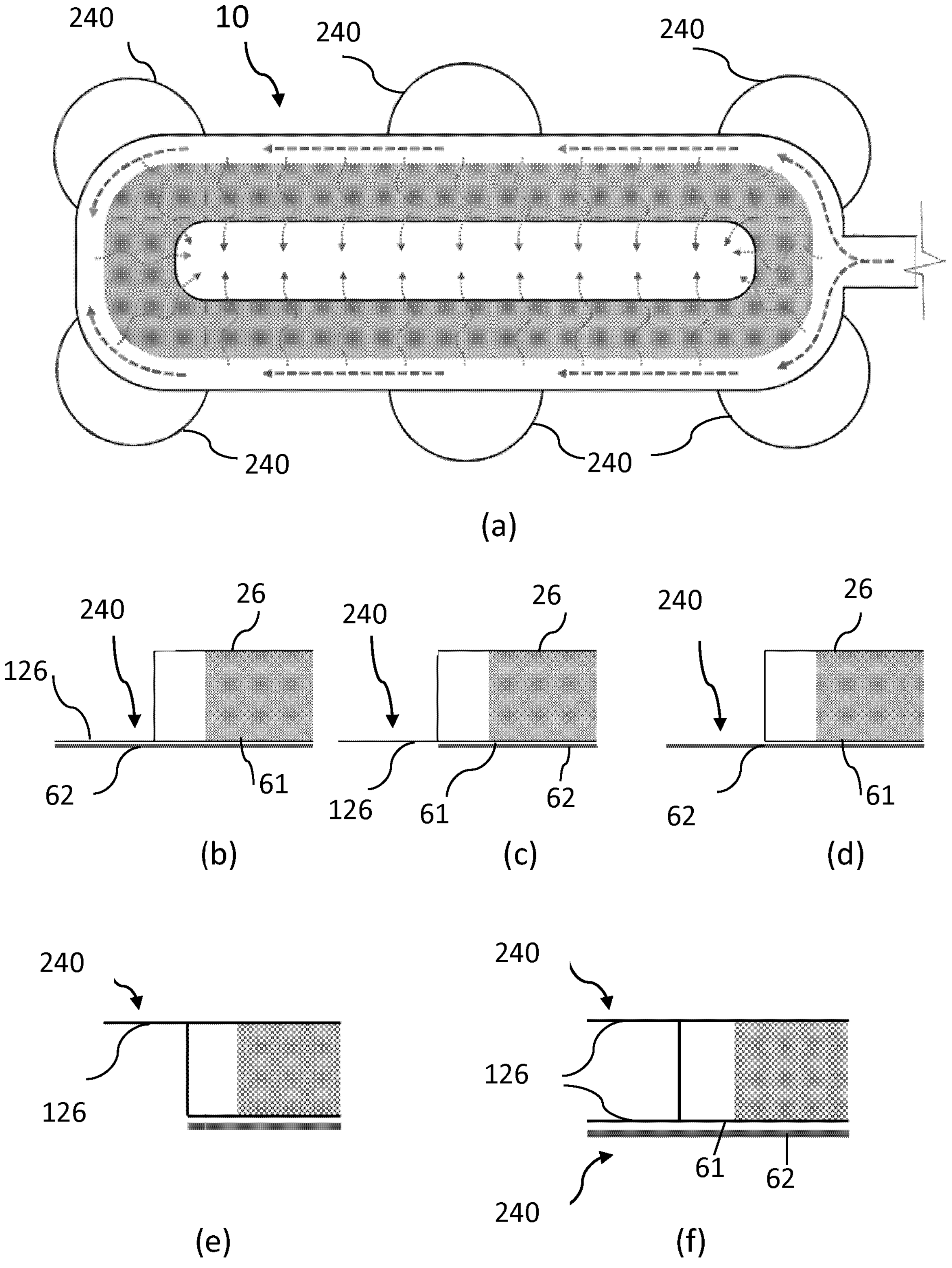
FIGS. 50*a*-*f* are a cross-sectional schematic view of a patient interface having fixing flanges and schematic partial side views of embodiments of the fixing tabs.

The patient interface 10 may include one or more flanges 240 extending laterally from the patient interface 10. FIG. 50 shows an embodiment of the patient interface 10 that includes a plurality of the flanges 240 spaced around the periphery of the patient interface 10.

The flange(s) 240, may be an extension of the adhesive layer 62 and/or outer membrane/enclosing wall/thin film 126 on the top surface 26 and/or bottom surface 61 of the patient interface 10 as shown in FIGS. 50*b-f*.

In FIG. 50*b*, the flange tab 240 comprises an extension of both the thin film 126 and the adhesive layer 62 at a bottom surface 61 of the patient interface 10. In FIG. 50*c*, the flange tab 240 comprises an extension of only the thin film 126 at the bottom surface 61. In FIG. 50*d*, the flange tab 240 comprises an extension of only the adhesive layer 62 at the bottom surface 61. In FIG. 50*e*, the flange tab 240 comprises an extension of the thin film 240 at the top surface 26 of the patient interface. In FIG. 50*f*, the flange tab 240 comprises an extension of the thin film 240 at the top surface 26 of the patient interface and also an extension of the thin film 126 and the adhesive layer 62 at the bottom surface 61. The flange tab(s) may be used in lifting the patient interface 10 off the patient after use and/or as a surface area for attachment to the skin of the patient by staples, screws, or similar. This may have particular application in types of surgery where the attachment surface is highly contoured. Whilst six of the flange tabs 240 are shown in FIG. 50, any suitable number may be used as required or as necessary.

Further characteristics of embodiments of the patient interface 10 are described below.

Components of the patient interface 10, such as the diffusing material portion 104 and outer membrane 126 may include bacteriostatic or bactericidal additives to reduce the risk of infection. Materials that naturally inhibit growth of microorganisms may also be used e.g. Ether based polyurethane materials. The patient interface 10 may also be pre-charged with antibiotics e.g. the diffusing material portion 104 may be pre-wetted with an aqueous antibiotics solution. Alternatively, powdered antibiotics may be pre-loaded into the patient interface 10.

Components of the patient interface 10, such as the diffusing material portion 104 and the outer membrane 126 may also include fire retardant additives to reduce risk of fire and burning during, for example, electrocautery procedures.

The patient interface 10 may be made entirely of the same material to assist with its recycling and/or disposal after use. For example, a polyurethane diffusing material portion 104 and outer membrane film 126 may dictate that a flow splitter 182, 188, 288 may also be constructed from polyurethane. All components being made from the same material aids end of life disposal of the patient interface 10.

When retracting the patient interface 10 from its initial state, as shown in FIG. 3*b*, some areas of the diffusing material portion 104 can be compressed more than other areas. To offset this, the diffusing material portion 104 may be cut in a shape that partially or fully represents the retracted state of FIG. 3*b* in which it is intended to be used. The diffusing material portion 104 is therefore in its compressed, stretched, or otherwise deformed state prior to retraction and in its more natural state when retracted. Performance of the patient interface 10 may therefore be sacrificed initially prior to incision such that the pore size and performance is optimized when the patient interface 10 is retracted and the wound the largest. The removable film 92 can be placed over the top of the wound to hold the diffusing material in its initial state under tension, such that the diffusing portion 104 doesn't spring open. Once the patient interface 10 is adhered to the patient, the removable film 92 can be cut along with the incision.

Figure 44:
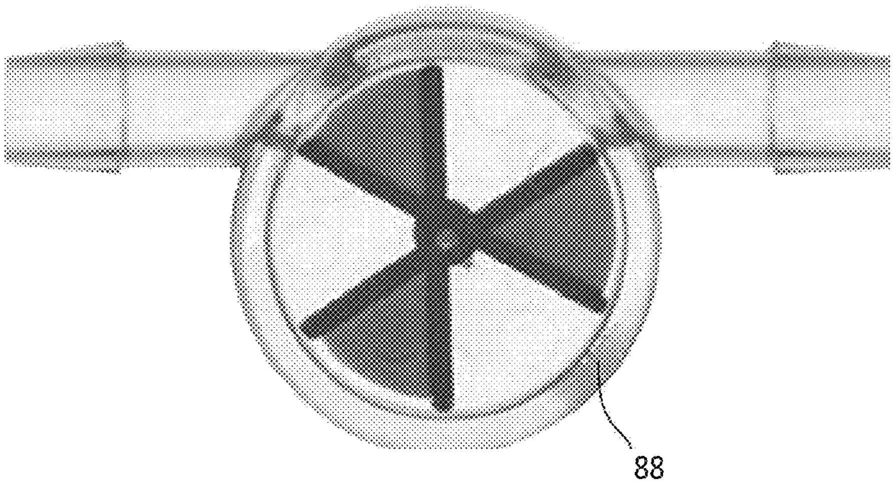
FIG. 44 is a plan view of an in-line function indicator.
Figure 45:
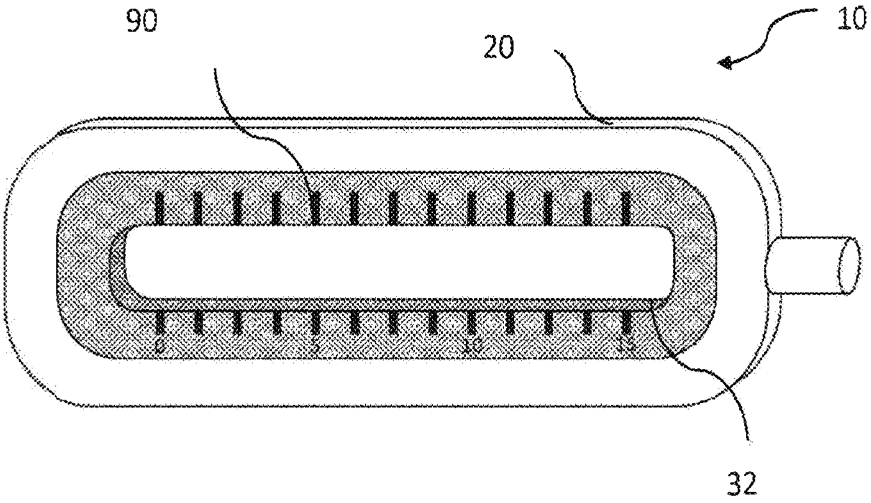
FIG. 45 is a perspective view of a patient interface including surgical incision length indicators.

The patient interface 10 and/or system 1 may incorporate a visual indication of when the gas flow is on and/or the system 1 is on and functioning correctly, for example that the gas is warmed and/or humidified, to assist the surgeon during a surgical operation. For example, a component of the patient interface 10 may change colour due to a detected change in temperature, flow, pH, humidity, gas concentration, pressure. For example, the patient interface 10 may include a $CO_2$ indicator, pressure sensitive paint or heat sensitive material. The indication may also be mechanical as well as visual e.g. a wind vane or propeller which spins in the presence of flow. An in-line flow indicator may be connected between the patient interface and a gas source to indicate when the gas flow is on. An example of such an in-line flow indicator 88 is the vane or propeller sealed within a housing, as shown in FIG. 44.

The component of the patient interface referred to above may be the flow director 184 or flow splitter 182, 188, 288 and/or the support structure 112, for embodiments in which the outer membrane 126 is translucent or transparent. Other components of the patient interface 10 are also possible as long as they are in direct, indirect and/or thermal communication with the gas flow. The flow director 184 or splitter 182, 188, 288 and/or the support structure 112 may be made from a thermochromic, and/or hydrochromic material. The thermochromic material changes colour when it changes from room temperature to an elevated temperature in the presence of warmed delivery gas. Similarly, a hydrochromic material may change colour when the material is exposed to elevated levels of moisture due to the presence of humidified delivery gas. It is possible to make the flow director 184 or flow splitter 182, 188, 288 or the support structure 112 or other component from a material that is both thermochromic and hydrochromic. In such an embodiment, the particular colour of the gas may provide an indication of the condition of the gas being delivered. For example, a colour 'A' may indicate that the gas is off, a colour 'B' may indicate that the gas heating is functioning, a colour 'C' may indicate that the humidification is working, and a colour 'D' may indicate that both the heating and humidification are working. A colour 'B' may for example serve as a warning indicator such that heated gas without humidification can pose a risk of wound tissue desiccation. Whilst the above example provides four options for recognising gas condition or properties, the gas colour may be used to provide any combination of the indicators, for example a greater or fewer number of indicators as desired. Other indicators of the gas condition than those described may be derived from different or further colours as applicable.

The component of the interface referred to above may similarly change colour in the presence of the delivery gas type e.g. it may change colour in the presence of $CO_2$ gas if $CO_2$ gas is used as the delivery gas. The component of the interface may similarly change colour in the presence of a certain drug or medicament.

The patient interface 10 may include one or more sensors (not shown). A temperature sensor, humidity sensor, stretch or strain sensor, or colour detector may be incorporated into the patient interface 10. For example, a stretch sensor may detect, monitor, and report on swelling. It may also indicate safe or damaging/harmful retraction forces. A colour temperature may detect, monitor, and report on reddening/inflammation at the wound edge. A humidity sensor may detect, monitor, and report on moisture levels and extent of wound exudate. A temperature sensor or sensors may be used as an indicator of temperature condition and used in the control of temperature at the patient interface 10 and/or in delivered gas conditions. The temperature sensor may include any suitable type of sensor such as a thermocouple, thermistor or infrared sensor/camera/detector. A motion sensor (e.g. accelerometer) can detect, monitor, and report on patient movement quantity and quality. Patient mobilisation is important in the recovery of orthopaedic patients.

Further details of the system 1 are described as follows. With further reference to FIGS. 1*a* and 1*b*, the system 1 includes the patient interface 10, gas source 14, combined flow generator and humidifier unit 15, or separate flow generator or flow controller 16, flow humidifier 17, and circuit 12. The flow controller 16 or a flow controller (not shown) that may typically be incorporated into the flow generator/humidifier unit 15 and/or humidifier 17 may be utilised for the control of gas flow and characteristics into the circuit 12 and/or patient interface 10. The gas source 14 may be bottled or operating theatre wall supply air, $CO_2$, nitrogen, or nitric oxide or any other suitable gas or mixture thereof. The circuit 12 is insulated, heated, flexible and of a small diameter e.g. >15 mm.

Where the flow generator 15,16 is a unit having for example a blower, pump or fan that entrains air in from the theatre environment, a suitable filter is included through which the air must pass. It may be advantageous to add a supplemental flow of a therapeutic gas to the entrained air flow e.g. add $CO_2$ through an inlet valve. The added $CO_2$ gas can improve oxygenation of the tissue to which the gases are applied via the patient interface.

In some embodiments, nebulised drugs may be added to the gases entering the patient interface 10. These drugs may for example assist with pain management (pain relievers), bleeding, and/or infection control (antibiotics). The patient interface 10, circuit 12, humidifier 17 and/or flow generator 15, 16 may facilitate the connection of or have an in-built nebuliser to deliver the aerosolised drugs and/or fluids such as topical anaesthetics, pain relief, warmed saline. Warmed saline can increase the capability of the system 1 to deliver warmth to the patient and reduce intraoperative hypothermia.

It will be appreciated by the skilled person that features of the various embodiments of the patient interface 10 described herein can be used in combination with one another where possible. As one non-limiting example, the features of FIGS. 18*a*-18*e* may be used in combination with the features of FIGS. 13*a*-13*f* and/or FIGS. 20*a*-20*p*.

Figure 24:
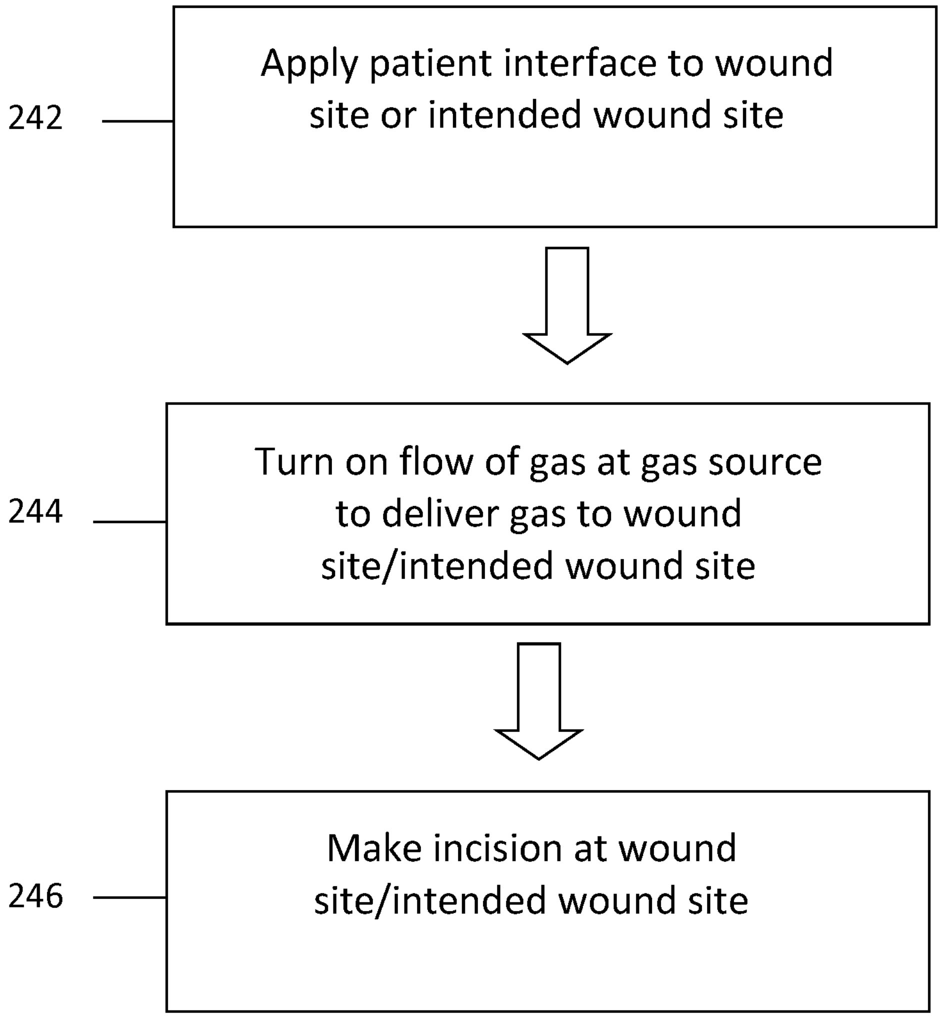
FIG. 24 is a schematic of method steps of a method of treatment of a wound.

The patient interfaces 10 described herein may be used in relation to any number or type of surgical procedures such as, but not limited to, orthopaedic, neuro surgery, vascular, plasticsor any other type of 'open' surgery. With reference to FIG. 24, the patient interface 10 and system 1 are used as follows. Prior to an incision being made at the wound site or intended wound site, at step 242 the patient interface 10 is applied to the wound site or intended wound site, by positioning it around the wound site or intended wound site. At step 244 the gas source 14 is turned on and a flow of gas is supplied from the gas source 14 to the patient interface 10 via the circuit 12 connected to the flow generator and/or humidifier 15, 16, 17. The gas or liquid may be conditioned at the flow generator/humidifier 15 or 16, 17. Specifically, the gas may be warmed to a physiological temperature (nominally 37° C.) and humidified to above about 80% relative humidity. Once the system 1 delivers conditioned or unconditioned gas to surround or at least partially surround the wound and create a protective microenvironment over it, an incision can be made at step 246. In some embodiments, a feedback loop may relay detected conditions back to a controller for the adjustment and/or maintenance of conditions such as but not limited to gas temperature and/or humidity.

In this manner, the wound site or intended wound site is protected immediately by the conditioned gas exiting the patient interface around the wound site, prior to an incision being made. However, it is also envisaged that steps 244 and 246 may be reversed in some instances.

Figure 51:
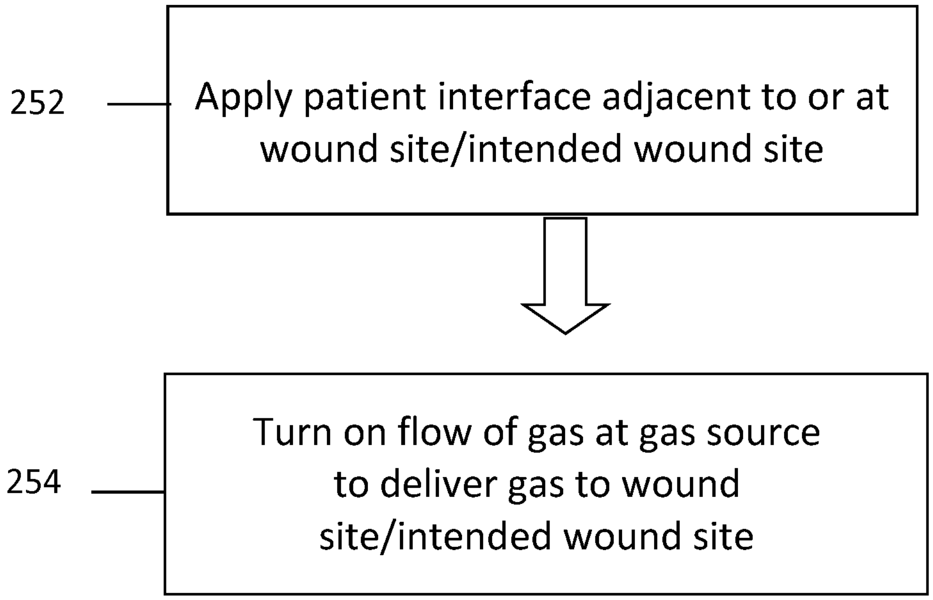
FIG. 51 is a schematic of method steps of a method of protecting a wound

With reference to FIG. 51, the patient interface 10 and system 1 may be used to protect a patient from surgical site infection, and/or loss of moisture and/or loss of heat. The method comprises, at step 252, applying the patient interface adjacent or at a wound site or intended wound site; and, at step 254, turning on a flow of gas from the gas source to the patient interface. The method may include conditioning the gas prior to its entry into the patient interface, where conditioning the gas may include one or more of conditioning the temperature, humidity level or oxygen level of the gas. Applying the patient interface adjacent or at a wound site or intended wound site may include applying multiple patient interfaces at or adjacent the wound site or intended wound site in order to adequately surround the wound site or intended wound site.

Table 1 below shows performance test results for a patient interface made in accordance with embodiments of the disclosure measured against a commercially available diffuser product. The gas was, in each test, humidified with a commercially available humidifier platform, such as those commercially available from Fisher & Paykel Healthcare Limited. Performance is measured by the reduction in heat and moisture loss from a model of an open surgical wound.

The commercially available diffuser resulted in 7.7 W of heat loss and 5.4 ml/hr of moisture loss from the wound. The patient interface made in accordance with embodiments of the present disclosure had an improved performance over the commercially available diffuser in tests in which the gas is $CO_2$ or air. By increasing a temperature of the humidifier heater plate and heater wire duty cycle it is possible to eliminate heat and moisture loss from the wound.

TABLE 1

| Patient Interface | Gas | Wound Heat loss (W) | Wound Moisture loss (ml/hr) |
|---|---|---|---|
| Commercially available diffuser | $CO_2$ | 7.7 | 5.4 |
| Patient interface in accordance with present disclosure | $CO_2$ | 4.1 | 0.8 |
| | Air | 7.5 | 1.9 |
| | $CO_2$ | 0 | 0 |
| | Air | 3.8 | TBD |

Embodiments of a patient interface 10 and a system 1 for treating and/or managing a wound have been described herein. It will be appreciated by the skilled person that embodiments of the patient interface 10, system 1 and its use in a method of management and/or treatment of a wound can produce an even distribution of flow of conditioned gases to the edge of a wound site, and/or to create a protective microenvironment over the wound that has an improved performance over known diffusers. Whilst features of the various embodiments have been described, it will be apparent to the skilled person that a feature or features from one embodiment may be used in conjunction with features from another embodiment without departing from the scope of the disclosure.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A patient interface for wound treatment or management, the patient interface comprising:

an interface body configured to substantially or at least partially surround a wound, the interface body comprising:

a gas inlet;

a first gas flow path;

a support structure, wherein the support structure at least partially defines the first gas flow path;

a second gas flow path; and a gas outlet configured to be at or adjacent to the wound;

wherein the first gas flow path is arranged in fluid communication with the gas inlet and the second gas flow path;

wherein the interface body is configured to be retractable between a first position and a second retracted position at which the interface body is in an expanded configuration whilst substantially maintaining at least the first gas flow path in an open position, wherein the support structure is configured to maintain the first gas flow path in the open position during retraction between the first position and the second retracted position, wherein the support structure is configured to allow the interface body to bend while maintaining a substantially constant cross-section along the first gas flow path during retraction from the first position to the second retracted position.

2. The patient interface of claim 1, wherein the wound comprises a surgical incision, and:

the first position comprises a first configuration of the interface body configured to substantially or at least partially surround the surgical incision prior to retraction of the surgical incision; and the second retracted position comprises a second configuration of the interface body configured to at least partially surround the surgical incision subsequent to retraction of the surgical incision.

3. The patient interface of claim 2, wherein:

a bottom surface of the interface body includes an adhesive material configured to adhere the interface body to a patient prior to formation of the surgical incision, and retraction of the surgical incision causes the interface body to transition from the first position to the second retracted position.

4. The patient interface of claim 1, wherein the interface body further comprises:

a diffusing material portion, wherein the second gas flow path and the gas outlet are defined at least partially through the diffusing material portion.

5. The patient interface of claim 4, wherein the interface body further comprises an outer membrane and wherein the first gas flow path is at least partially defined between the outer membrane and the diffusing material portion.

6. The patient interface of claim 4, wherein:

the support structure is arranged along an outer side of the interface body configured to face away from the wound; and the diffusing material portion is arranged along an inner side of the interface body configured to face toward the wound.

7. The patient interface of claim 4, wherein the diffusing material portion comprises a stretchable porous material.

8. The patient interface of claim 7, wherein the stretchable porous material comprises an open cell foam.

9. The patient interface of claim 4, wherein the diffusing material portion defining the second gas flow path increases in thickness from the gas inlet to a distal portion.

10. The patient interface of claim 1, wherein the support structure comprises a flexible structure configurable to conform to contours of a body of a patient surrounding a wound site.

11. The patient interface of claim 1, wherein the support structure is configured to be elastically deformable under application of at least one of a laterally, vertically, and longitudinally applied force.

12. The patient interface of claim 1, wherein the support structure comprises a plurality of interconnected elements arranged in a repeating pattern over a longitudinal axis of the support structure.

13. The patient interface of claim 1, wherein the support structure comprises a scaffold or a spring.

14. The patient interface of claim 1, wherein a bottom surface of the interface body includes an adhesive material.

15. A patient interface for wound treatment or management, the patient interface comprising:

an interface body configured to substantially or at least partially surround a surgical incision, the interface body comprising:

a gas inlet;

a support structure positioned along an outside edge of the interface body configured to face away from the surgical incision; and a diffusing material portion positioned along an inside edge of the interface body configured to face toward the surgical incision;

wherein the interface body is configured to receive a gas from the gas inlet and deliver the gas through the diffusing material portion toward the surgical incision;

wherein the interface body is configured to deform between a first position prior to retraction of the surgical incision and a second position subsequent to retraction of the surgical incision, wherein the support structure is configured to maintain a gas flow path defined by the support structure in an open position in the first position and the second position, wherein the support structure is configured to allow the interface body to bend while maintaining a substantially constant cross-section along the gas flow path during deformation from the first position to the second position.

16. The patient interface of claim 15, wherein the support structure comprises a flexible structure configurable to conform to contours of a body of a patient surrounding a wound site.

17. The patient interface of claim 15, wherein the support structure is configured to be elastically deformable under application of at least one of a laterally, vertically, and longitudinally applied force.

18. The patient interface of claim 15, wherein the support structure comprises a plurality of interconnected elements arranged in a repeating pattern over a longitudinal axis of the support structure.

19. The patient interface of claim 15, wherein the interface body further comprises an adhesive material on a bottom surface of the interface body configured to adhere the interface body to a patient.

20. A method, comprising:

positioning a patient interface on a patient such that the patient interface at least partially surrounds a location at which a surgical incision is to be made during a medical procedure, wherein the patient interface comprises a gas inlet and is configured to deliver gases to the location;

delivering a flow of gas to the location via the patient interface before the surgical incision is made;

continuing to deliver the flow of gas to the patient interface after the surgical incision is made; and retracting the surgical incision, wherein retraction of the surgical incision causes a change in shape of the patient interface between a first position and a second retracted position at which a body of the patient interface is in an expanded configuration whilst substantially maintaining at least a first gas flow path in an open position, wherein the body of the patient interface comprises a support structure at least partially defining the first gas flow path, the support structure configured to maintain the first gas flow path in the open position during retraction between the first position and the second retracted position, wherein the support structure is configured to allow the body of the patient interface to bend while maintaining a substantially constant cross-section along the first gas flow path during retraction from the first position to the second retracted position, and wherein the flow of gases is delivered to the surgical incision while the surgical incision is in a retracted state.

* * * * *